US009217161B2

(12) United States Patent
Kohn

(10) Patent No.: US 9,217,161 B2
(45) Date of Patent: Dec. 22, 2015

(54) PROCESS FOR PRODUCING FERMENTATION PRODUCTS AND FERMENTATION MEDIUM COMPOSITIONS THEREFOR

(76) Inventor: Richard Allen Kohn, Columbia, MD (US)

( * ) Notice: Subject to any disclaimer, the term of this patent is extended or adjusted under 35 U.S.C. 154(b) by 197 days.

(21) Appl. No.: 13/381,127

(22) PCT Filed: Dec. 3, 2010

(86) PCT No.: PCT/US2010/058959
§ 371 (c)(1),
(2), (4) Date: Dec. 28, 2011

(87) PCT Pub. No.: WO2011/069105
PCT Pub. Date: Jun. 9, 2011

(65) Prior Publication Data
US 2012/0100591 A1    Apr. 26, 2012

Related U.S. Application Data

(60) Provisional application No. 61/266,610, filed on Dec. 4, 2009, provisional application No. 61/328,368, filed on Apr. 27, 2010.

(51) Int. Cl.
*C12P 5/02* (2006.01)

(52) U.S. Cl.
CPC ........................................ *C12P 5/02* (2013.01)

(58) Field of Classification Search
None
See application file for complete search history.

(56) References Cited

U.S. PATENT DOCUMENTS

| | | |
|---|---|---|
| 2008/0187975 A1 | 8/2008 | Kohn |
| 2009/0006280 A1 | 1/2009 | David |
| 2010/0221798 A1 | 9/2010 | Schirmer et al. |
| 2010/0242345 A1 | 9/2010 | Keasling et al. |
| 2010/0249470 A1 | 9/2010 | Schirmer et al. |
| 2010/0251601 A1 | 10/2010 | Hu et al. |
| 2011/0111475 A1 | 5/2011 | Kuhry et al. |
| 2011/0124071 A1 | 5/2011 | Schirmer |

FOREIGN PATENT DOCUMENTS

| | | | |
|---|---|---|---|
| WO | 2007/095215 A2 | 8/2007 | |
| WO | 2008/103480 A2 | 8/2008 | |
| WO | WO 2008/103480 A2 * | 8/2008 | ............... C10G 1/00 |

OTHER PUBLICATIONS

Strobel G. et al.,"The production of myco-diesel hydrocarbons and their derivatives by the endophytic fungus Gliocladium roseum (NRRL 50072)", Microbiology 154: 3319-3328 (2008).*
Ladygina et al., Process Biochemistry "A review on microbial synthesis of hydrocarbons" (May 2006) vol. 41: pp. 1001-1016.
Strobel, G. A., B. Knighton, K.Klluck, Y. Ren, T. Livinghouse, M. Griffin, D. Spakowicz, andJ. Sears. "The production of myco-diesel hydrocarbons and their derivatives by the endophytic fungus Gliocladium roseum (NRRL 50072)" Microbiology. (Nov. 2008) vol. 154 (11): pp. 3319-3328.
Strobel, G. A. E. Dirkse, J. Sears, and C. Markworth. "Volatile antimicrrobials from Muscodor albus, a novel endophytic fungus" (Nov. 2001) Microbiology. vol. 147: pp. 2943-2950.
Sunesson, A. L., W. H. J. Vaes, C. A. Nilsson, G. Blomquist, B. Anderssson, and R. Carlson. "Identification of volatiel metabolites from five fungal species cultivaed on two media" (1995) Applied Environmental Microbiology vol. 61: pp. 2911-2918.
McAfee, B. J., and A. Taylor. "A review of the volatile metabolites of fungi found on wood substrates" Natural Toxins (1999) vol. 7: pp. 283-303.
Stinson, M., E. Ezra, G. Strobel, "An endophytic *Gliocladium* sp. of *Eucryphia cordifolia* producing selective volatile antimicrobial compounds." Plant Science (2003) vol. 165: pp. 913-922.
Wackett, L. P., J. A. Frias, J. L. Seffernick, D. J. Sukovich, and S. M. Cameron. "Genomic and biochemical studies demonstrating the absence of an alkane-producing phenotype in Vibrio furnissii M1", Applied Environmental Microbiology (Nov. 2007) vol. 73: pp. 7192-7198.
Park M. O. "New pathway for long-chain n-alkane synthesis via 1-alcohol in Vibrio furnissii M1" Journal of Bacteriology (2005) vol. 187: pp. 1426-1492.
Park, M. O., K. Heguri, K. Hirata, and K. Miyamoto. "Production of alternatives to fuel oil from organic waste by the alkane-producing bacterium Vibrio furnissii M1" Journal of Applied Microbiology (2005) Journal of Applied Microbiology vol. 98: pp. 324-331.
Park, M. O., M. Tanabe, K. Hirata, and K. Miyamoto, "Isolaton ad characterization of a bacterium that produces hydrocarbons extracellularly which are equivalent to light oil." Applied Microbiology Biotechnology (2001) vol. 56: pp. 448-452.
Withers, S. T., and J. D. Keasing. "Biosynthesis and engineering of isoprenoid small molecules", Applied Environmental Microbiology (2007) vol. 73: pp. 6277-6283.
Alper, H. and G. Stephanopoulos, "Engineering for biofuels: exploiting innate microbial capacity or importing biosynthetic potential?" Nature Reviews Microbiology (Oct. 2009) vol. 7: pp. 715-723.
Kalscheur, R., T. Stoveken, H. Luftmann, U. Malkus, R. Reichelt and A. Stenbuchel, "Neutral lipid biosynthesis in engineered *Escherichia coli*: jojoba oil-like wax esters and fatty acid butyl esters" Microbology (2006) vol. 152: pp. 2529-2536.
Wackett "Biomass to fuels via microbial transformations" Current Opinion in Chemical Biology [online] (Apr. 2008) 12:187-193. pp. 187, 191.
Pind,P. "Dynamics of the anaerobic process: effects of volatile fatty acids", Biotechnology and Bioengineering. (Jun. 30, 2003). vol. 82: (7) pp. 791-801.

(Continued)

*Primary Examiner* — Anand Desai

(57) ABSTRACT

Fermentation products (e.g., bioproducts such as hydrocarbons and other organic compounds) are produced from biomass or gases through digestion and fermentation under conditions that thermodynamically favor production of the fermentation products.

19 Claims, 3 Drawing Sheets

(56) References Cited

Figure 1:
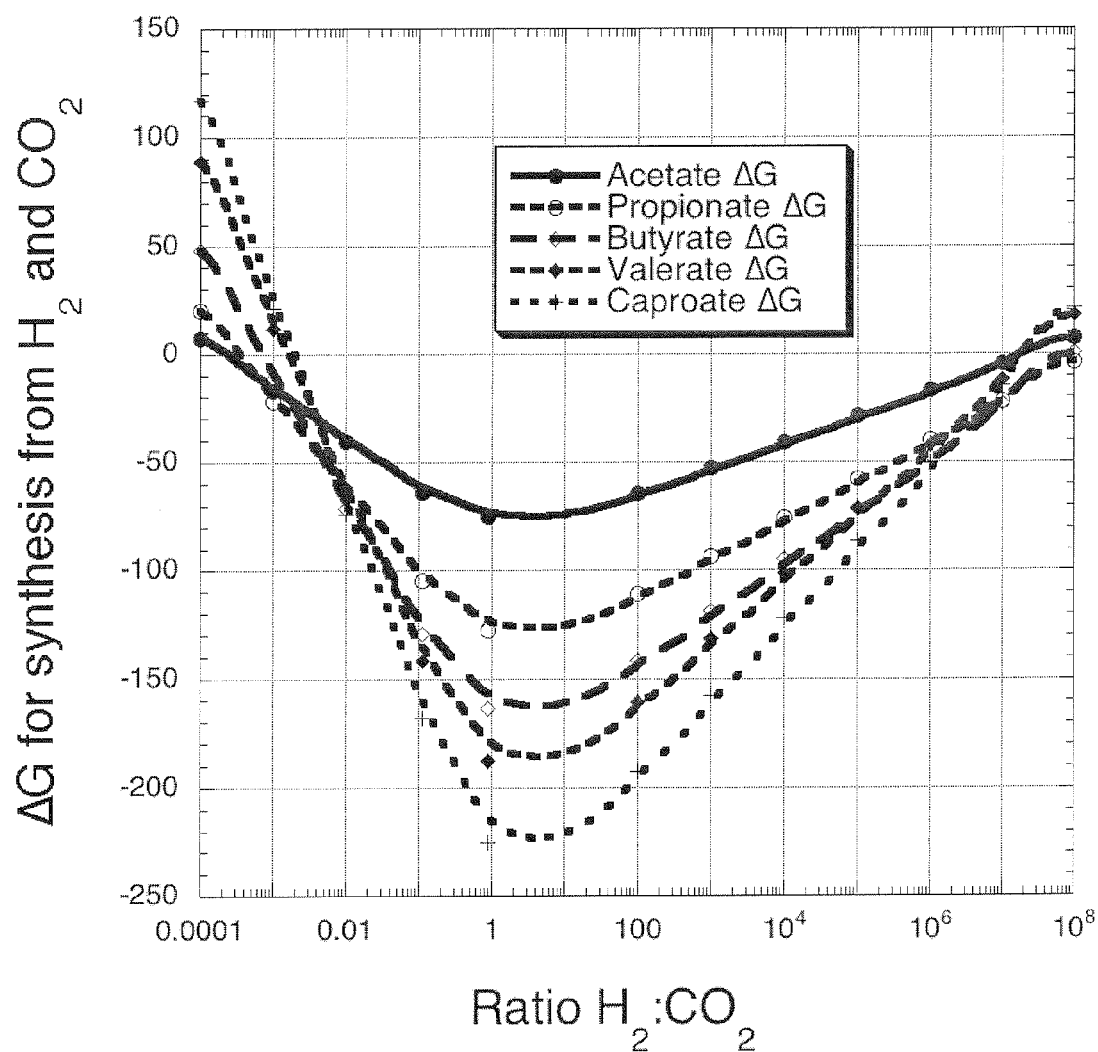

OTHER PUBLICATIONS (Published after priority date) Weimmer, P. "End product yields from the extraruminal fermentation of various polysaccaride, proein and nucleic acid components of biofuels feedstocks" Bioresource Technology. (Feb. 2011) vol. 102: pp. 3254-3255.

Chan, W. N., M. T. Holtzapple, 2003. Conversion of municipal solid wastes to carboxylic acids by thermophilic fermentation. , Applied Biochemistry and Biotechnology. (Nov. 2003) vol. 111: pp. 93-112.

Henstra, A. M., J. Sipma, A. Rinzema, A. J. M. Stams. "Microbiology of synthesis gas fermentation for biofuel production." Current Opinion in Biotechnology, Jun. 2007, vol. 18 (3) pp. 200-206.

* cited by examiner

PROCESS FOR PRODUCING FERMENTATION PRODUCTS AND FERMENTATION MEDIUM COMPOSITIONS THEREFOR

RELATED APPLICATIONS

This application claims priority to PCT Application No. PCT/US2010/058959 filed on Dec. 4,2009, which claims priority to U.S. Provisional Patent Application No. 61/266, 610 Filed on Dec. 4,2009 and U.S. Provisional Patent Application No. 61/328,368 filed on Apr. 27,2010.

BACKGROUND OF THE INVENTION

1. Field of the Invention

The present invention relates to fermentation processes and fermentation medium compositions, and in particular to processes for producing fermentation products under conditions that thermodynamically favor production of the fermentation products.

2. Background

Bioproducts and biofuels are organic compounds made from recently living organic matter. Biofuels present the possibility of capturing and storing solar energy in a cost effective and environmentally sustainable manner. In addition, waste biomass that would otherwise be stored in landfills can be converted to biofuels. Bioproducts can also displace the need for fossil fuels to produce such products as plastics.

Currently ethanol made from corn grain is the main biofuel produced in the U.S. Alternatively, methane is made from animal manure and burned for heat or electricity. Methane is a one-carbon alkane. These two options currently provide a limited amount of fuel at a low level of efficiency. Acetic acid used in many industrial applications is made from fossil fuel or from the ethanol in wine or cider. Carboxylic acids like acetic acid, propionic acid, butyric acid and others could be used to make alcohols, alkanes, or polymers if the cost of their production could be kept low enough. Currently, lactic acid is made from sugar or starch, and it is used to produce a bioplastic. Wherein many of these organic compounds are produced from fossil fuels, or from expensive sources of biomass like sugar or starch, a means to make various bio-products from inexpensive sources of biomass like plant fiber is needed.

If bioproducts and biofuels could be inexpensively produced from plant fiber, waste biomass like leaves, paper, manure, wood byproducts, and others could offset fuel shortages. Plant fiber, also called cellulosic biomass because it contains cellulose, can be grown on marginal land and in greater yields than grain crops. Eventually, the U.S. aims to use up to a billion tons of such biomass per year. However, there are few processes available to breakdown plant fiber comprised of cellulose, hemicellulose, pectin, and lignin. Many of these processes are inconvenient or expensive because of the difficulty in degrading plant cell wall. There is a need to further increase the rate and extent of plant fiber digestion to produce bioproducts.

The microorganisms that live in the first stomach chamber, or rumen, of cattle and other ruminants can readily degrade plant cell wall but they produce a mixture of acids rather than specific bioproducts. Other sources of microorganisms like animal feces, insect gut, or compost also produce a mixture of organic acids or methane but not high concentrations of specific carboxylic acids, alcohols, or longer-chain alkanes. Previous disclosures by the inventor (U.S. Ser. No. 60/870,441; U.S. Ser. No. 12/000,856; U.S. Ser. No. 61/113,337; U.S. Ser. No. 12/385,215; U.S. Ser. No. 61/165,654) describe production of acids, alcohols, methane, or hydrogen from biomass using fermentation, and the use of thermodynamics to shift fermentation profiles toward desired products. However, there is a need to produce additional products.

Synthesis gases ($CO_2$, CO and $H_2$) can be produced as byproducts of fossil fuel or biofuel production or from heating of biomass to high temperatures with limited oxygen. Thus, it may also be advantageous to make bioproducts like alcohols, alkanes or acids from such gases. Previous disclosures (U.S. Ser. No. 61/165,654; PCT/US2010/029707) describe methods to convert gases into alcohols, specific acids, or methane, and the use of thermodynamic analysis to shift fermentation toward desired products and to produce higher concentrations of desired products.

An alternative to ethanol from corn grain or methane from animal manure would be to produce various hydrocarbons (e.g. alkanes, alkenes, and alkynes) from different types of biomass. Hydrocarbons may range in size with the short-chain hydrocarbons being gaseous at room temperature and long-chain hydrocarbons being liquids at room temperature. Currently most hydrocarbons are produced from fossil fuels. Alkanes greater in length than one-carbon are generally understood to derive from fossil degradation of biomass under high pressures and temperatures. It would be advantageous to produce hydrocarbons greater than one carbon in length through microbial digestion and fermentation. An advantage of hydrocarbon production over ethanol or methane is that longer-chain hydrocarbons would be separated easily from the liquids in which they are produced, and they would be more easily condensed or compressed than methane. For example, propane is a gas that would bubble from fermentation liquid, but can be readily compressed to liquid propane gas. Higher chain-alkanes like hexane or octane could be separated readily from liquids and used to extend gasoline. Thus, it would be advantageous to produce alkanes from various sources of biomass or from synthesis gases ($CO_2$, CO, $H_2$).

Hydrocarbons greater in length than one-carbon are generally understood to derive from fossil degradation of biomass under high pressures and temperatures and millions of years time. Only a few microorganisms have been discovered that produce trace quantities of certain alkanes. One may contemplate genetic engineering approaches to develop organisms that convert a large quantity of some type of biomass, such as a sugar or plant fiber, or to convert synthesis gases, to hydrocarbons. These organisms may be developed by first isolating organisms that produce trace quantities of hydrocarbons, and then identifying metabolic pathways that produce the hydrocarbons. The genes encoding the enzymes in those pathways may then be inserted into the genome of a convenient host organism and through known genetic engineering techniques those genes may be turned on. However, even though genetic engineering approaches are now facilitated by current technologies, developed organisms often do not survive well, or compete well against mutants or contaminant organisms. The resultant organisms often do not produce the desired products even when the enzymes are present.

Previous disclosures by the inventor (U.S. Ser. No. 60/870, 441; U.S. Ser. No. 12/000,856; U.S. Ser. No. 61/113,337; U.S. Ser. No. 12/385,215; U.S. Ser. No. 61/165,654; PCT/US2010/029707) describe using mathematical models based on the second law of thermodynamics to define conditions that determine which products are produced in a fermentation process and to accelerate the digestion and fermentation process. For example, the simplest alkane, methane, can be made to evolve more quickly by removing fermentation gases to decrease the partial pressures of gases in the fermentation. Likewise, more alkyl alcohols can be produced through fermentation by manipulating the concentrations and the ratios of concentrations of products and reactants to make the desired products more thermodynamically favorable. It would be advantageous to apply the same approach to produce other organic compounds such as hydrocarbons from biomass or synthesis gases.

BRIEF SUMMARY OF THE INVENTION

The disclosed invention embodies a process to produce organic compounds such as hydrocarbons (e.g. alkanes, alkenes, alkynes) or other compounds using microorganisms and manipulation of reactants and products to shift fermentation toward the desired products in accordance with the second law of thermodynamics.

The current invention comprises a process to directly convert biomass, including plant fiber, to alkanes with greater than one carbon through anaerobic digestion and fermentation. Alternatively, the biomass may be converted to acids, and the acids can be converted to alkanes through a chemical process or a simultaneous or subsequent fermentation process. The invention may combine production of acids from biomass with production of alkanes from the acids in a single fermentation. The length of the acids may be extended through controlling concentrations of reactants and products before converting the acids to alkanes to make longer-chain alkanes.

The invention also comprises producing alkanes from synthesis gases. In one aspect, the synthesis gases can be converted to acids and these acids subsequently converted to alkanes. In another aspect of the invention, the synthesis gases can be converted directly to alkanes using a microbial culture and the correct conditions and concentrations of products and reactants of desired and undesired pathways to shift fermentation toward the desired products.

The invention further comprises a composition that is a microbial culture that converts biomass, such as cellulosic biomass, directly to alkanes.

The invention also comprises a microbial culture that converts organic acids or synthesis gases to alkanes. The invention also comprises a microbial culture to make carboxylic acids from biomass or gases ($CO_2$, CO and $H_2$). The carboxylic acids can range in length from C2 to C18 or greater, and the length of shorter carboxylic acids may be extended under certain conditions. It is a further object of the invention to provide a culture of microorganisms that converts carboxylic acids to hydrocarbons such as ethane, propane, butane and alkanes with longer chain length such as octane and isooctane, branched-chain hydrocarbons, as well as alkenes and alkynes such as butene from valerate and acetylene from butyrate. It is a further object of the invention to provide a culture of microorganisms that assimilates $CO_2$ and $H_2$ or CO and $H_2$ into hydrocarbons such as an alkane longer than 1 carbon in length, alkene, or alkyne.

In each case, the microbial culture can be a mixed culture or a pure monoculture and one or two alkanes may be produced or a mixture of several. In each case, the microbial culture may be comprised of microorganisms that may or may not have been genetically modified.

The invention also comprises a process to isolate and enrich the microbial cultures used in the invention. This process includes establishing conditions to enrich microbial cultures to increase the activity that leads to greater production of alkanes from biomass or gases. Further, the invention comprises methods to isolate pure cultures of microorganisms that digest biomass or produce alkanes from biomass or both, or that convert acids to alkanes, or that directly or indirectly produce alkanes from synthesis gases. The invention also comprises a method to produce alkanes in mono-culture or mixed cultures of microorganisms that may optionally be genetically engineered to decrease production of undesired products or to increase production of desired products, or the genes for the necessary enzymes to produce alkanes may be used to transform other organisms.

These organisms may also be used under different thermodynamic conditions to degrade alkanes or organic acids to $CO_2$ and methane or $CO_2$ and water.

The invention also comprises using the second law of thermodynamics to determine conditions that control the fermentation to produce alkanes or carboxylic acids and select for microbes that produce alkanes or desired carboxylic acids from biomass, acids or gases. The second law of thermodynamics may also be used to determine conditions that will direct evolution of organisms so they produce alkanes or the desired carboxylic acids in greater concentration or greater efficiency of conversion.

Another embodiment of the invention is a mathematical model that uses calculation of Gibbs Free Energy between and among reactions under different conditions (e.g. temperature, pH) and different concentrations of products and reactants to identify appropriate or optimal conditions to produce desired hydrocarbons.

It is a further object of the present invention to provide a method to shift fermentation towards producing specific desired organic compounds, or producing higher concentration of specific desired compounds than would be produced in lower concentrations by natural conditions of fermentation.

One embodiment of this process is to produce hydrocarbons greater than one carbon in length by conducting the microbial fermentation under greater than 1 atm pressure, preferably greater than 2 or even more preferably greater than 4 atm pressure, or with a molar ratio of $H_2$ to $CO_2$ that is higher than natural fermentation and may approach 3 to 1.

In a different embodiment of the invention, the microbial process may be conducted under low pressure such as less than 1 atm and preferably less than 0.5 atm or even less than 0.05 atm, or with purging with gases such as argon or $N_2$ to decrease the partial pressures of $H_2$ and $CO_2$, to favor dehydrogenation and creation of double or triple bonds in products. For example, valerate was converted to the alkenebutene when fermented under vacuum, and butyrate was converted to alkyne acetylene under vacuum.

For example, microorganisms were cultured that produced ethane, propane, 1-butane, isobutane, 1-pentane, 1-hexane, 1-heptane, and 1-octane and branched-chain alkanes.

This invention also embodies isolated microorganisms that produce hydrocarbons such as alkanes greater than one carbon in length from biomass or $CO_2$, CO and $H_2$. Isolated organisms were more than 97% homologous with 16S rRNA of members of the genera *Actinomyces, Enterococcus, Eschericia, Clostridium, Proteus*, and *Tissierella*. These isolated organisms may obtain energy and grow while producing the hydrocarbons from gases.

It is moreover, a further object of the present invention to enrich and isolate naturally occurring microorganisms for producing organic compounds, such as acids, alcohols, hydrocarbons, or others.

It is a further object of the invention to provide a culture of microorganisms that degrades plant fiber such as ligno-cellulose with added $H_2$ to predominantly produce propionic acid.

It is a further object of the invention to provide a culture of microorganisms that degrades plant fiber or other biomass to predominantly produce butyric acid or valeric acid or longer chain acid.

It is a further object of the invention to provide a culture of microorganisms that assimilates $CO_2$ and $H_2$ or CO and $H_2$ into ethanol, propanol, acetate, propionate, butyrate or other alcohol or volatile fatty acid wherein the organisms predominantly produce one or two of the major products and tolerate a high concentration of the product.

Another embodiment of the invention is a process to degrade organic compounds such as hydrocarbons (e.g. alkanes, alkenes, alkynes) or other compounds using microorganisms and manipulation of reactants and products to shift fermentation toward shorter-chain alkanes or $CO_2$ and $H_2$.

The above objects and others are provided by a method for producing the organic compounds from biomass containing plant fiber or from gases, which entails digesting or fermenting the biomass containing plant fiber or gases with one or more microorganisms which directly digest the biomass containing plant fiber, or which assimilate the gases, and which microorganisms are tolerant to the accumulation of the desired product.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 1 shows the change in Gibbs Free Energy ($\Delta G$; kJ/mol) for synthesis of carboxylic acids from $H_2$ and $CO_2$ as the molar ratio of $H_2$ to $CO_2$ increases. The figure shows that which products are favored depends on the ratio of $H_2$ to $CO_2$, with longer chain acids particularly favored as the molar ratio of $H_2$ to $CO_2$ approaches 3. Potentially linked reactions to produce ATP were not included in the calculation. Model assumed 1 atm total pressure, 0.001 M aqueous carboxylic acids, temperature 40° C., pH=6.5. Conversion of gases to end product can occur without additional energy when the $\Delta G$ is negative.

Figure 2:
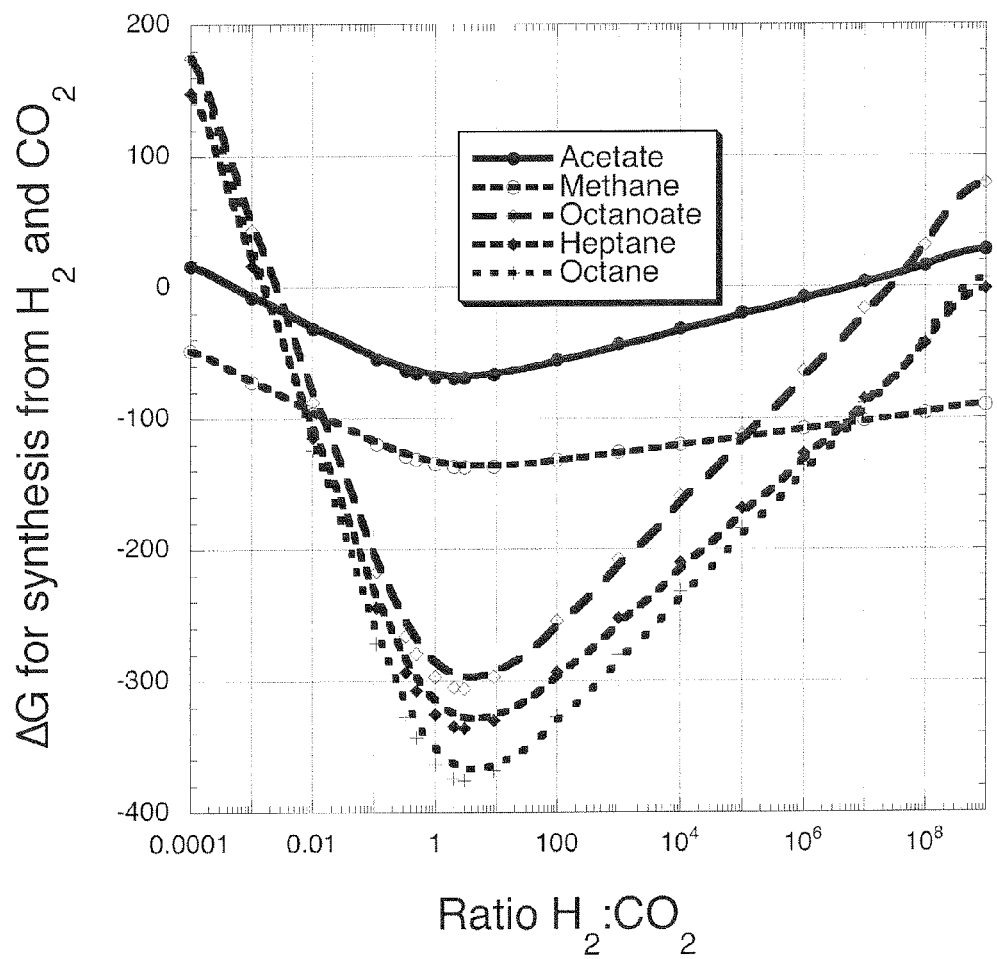

FIG. 2 shows the change in Gibbs Free Energy ($\Delta G$; kJ/mol of product) for synthesis of alkanes or carboxylic acids from $CO_2$ and $H_2$. The figure shows that which products are favored depends on the ratio of $H_2$ to $CO_2$, with longer chain acids and alkanes particularly favored as the molar ratio of $H_2$ to $CO_2$ approaches 3. At this ratio, alkanes are favored over acids of similar length. Potentially linked reactions to produce ATP were not included in the calculation. Model assumed 1 atm total pressure, 0.001 M aqueous carboxylic acids, 0.01 atm alkane gas (with soluble gas in equilibrium), temperature 40° C., pH=5.0. Conversion of gases to end product can occur without additional energy when the $\Delta G$ is negative.

Figure 3:
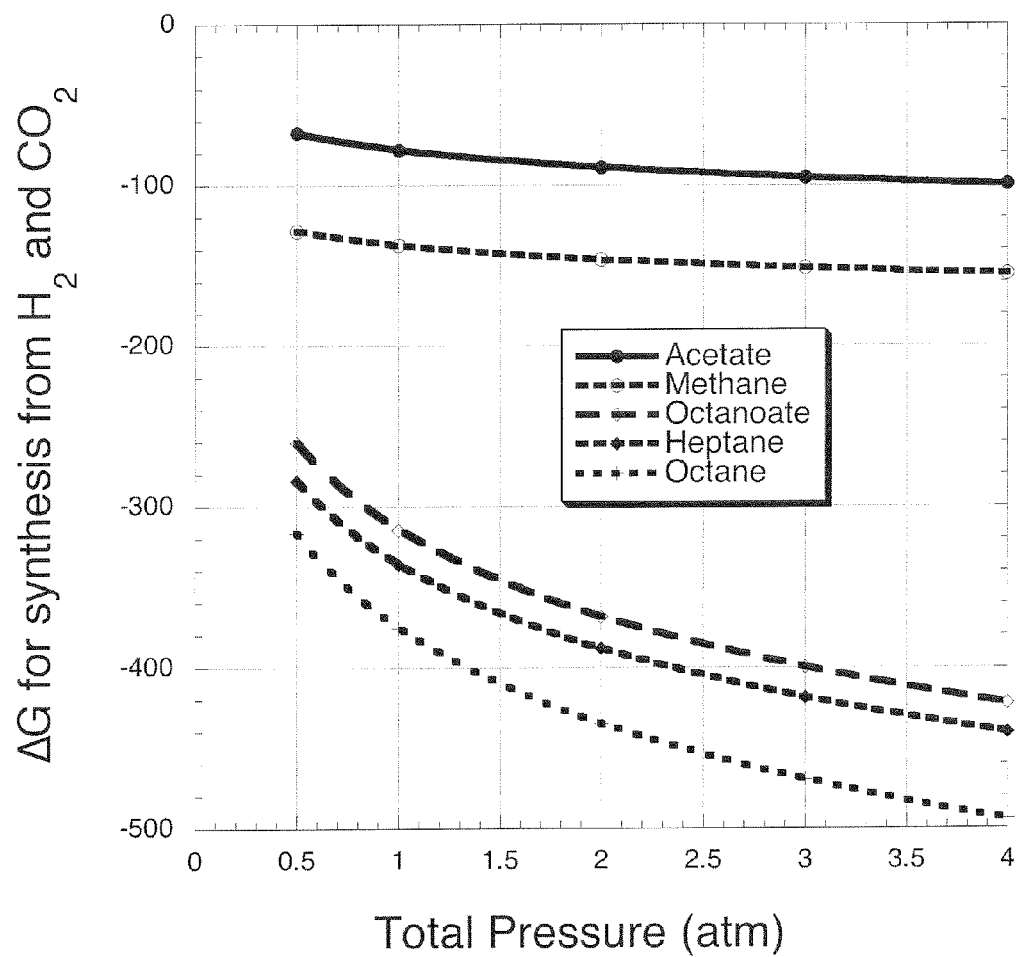

FIG. 3 shows the change in Gibbs Free Energy ($\Delta G$; kJ/mol of product) for synthesis of alkanes or carboxylic acids from $CO_2$ and $H_2$. The figure shows that as the total pressure of $H_2$ and $CO_2$ increases at a constant ratio, longer chain alkanes and acids are favored over shorter alkanes and acids, and alkanes are favored over acids of a similar length. Potentially linked reactions to produce ATP were not included in the calculation. Model assumed a ratio of $H_2$:$CO_2$ of 3, 0.001 M aqueous carboxylic acids, 0.01 atm alkane gas (with soluble gas in equilibrium), temperature 40° C., pH=6.5. Conversion of gases to end product can occur without additional energy when the $\Delta G$ is negative.

DETAILED DESCRIPTION OF THE INVENTION

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

Term Definitions

About: means plus or minus 10% of the amount indicated for 95% of examples unless otherwise indicated.

Acid Detergent Fiber or ADF: means the dry residue remaining after boiling a biomass sample in dilute sulfuric acid for one hour, and filtering usually through a fritted glass filter under vacuum. Acid detergent fiber is comprised of cellulose and lignin. Some heat-damaged protein and ash may also be included.

Alkanes: means any of the series of saturated hydrocarbons including methane, ethane, propane, butane, etc. Alkanes have the molecular formula $C_nH_{2n+2}$.

Alkenes: means any of the series of hydrocarbons with at least one double bond. For example, ethene, propene and butene are alkynes.

Alkynes: means any of the series of hydrocarbons with at least one triple bond. For example, acetylene (a.k.a. ethyne) is an alkyne.

Carboxylic acid or fatty acid: means an organic compound containing the carboxyl group COOH or COO$^-$ making it an organic acid because the proton (H$^+$) can be donated. Carboxylic acids range in length from 1 to many carbons, such as greater than 20 carbons. The short-chain carboxylic acids (C2 to C5) are volatile fatty acids.

Cellulosic biomass: means biomass containing cellulose, which is composed of 1, 4 beta-linked glucose molecules. Cellulosic biomass typically also contains other components of plant fiber including hemi-cellulose and pectin, or other materials. Examples of cellulosic biomass include, for example, hay, grass, paper, cotton, and wood.

Conversion percentage by weight: means the percentage of cellulose weight converted to alkane or other product. This calculation does not include exogenous water or hydrogen that may also be incorporated into alkane. For example, 37% conversion of cellulose to ethane by weight means that 1 g of cellulose (molecular weight=162 per glucose equivalent) is converted to 0.37 g of ethane (molecular weight=30). It could also be described as two moles of ethane per mole of glucose equivalent from cellulose=60/162×100=37%.

Defined cultures: means cultures of microorganisms that have been isolated and characterized to some extent, possibly identified as genus and species, and possibly characterized by sequencing the variable region of 16S rDNA, or by sequencing the complete genome.

Direct digestion: means the microorganisms act directly on the cellulosic biomass in its natural form (e.g. grass or hay) with minimal pretreatment to digest the cellulosic or fibrous content.

Direct evolution: means to direct the development of microorganisms that are well suited, preferably particularly well suited, for a given environment that is different from the environment from which the organism was taken, thereby changing the organism to be better suited to the new environment.

Directed Equilibrium: means the process or invention disclosed herein in which a system is allowed to move toward equilibrium, but concentrations of reactants and products within the system are manipulated, and possibly some reactions are directly inhibited, to direct the system toward a different equilibrium than would otherwise be approached.

Favorable Gibbs Free Energy for Synthesis: means the change in Gibbs Free Energy ($\Delta G$) is negative for the combination of reactions that comprise the system that converts a set of reactants to a set of products, and the system can therefore convert the reactants to products. The $\Delta G$ is calculated based on the change in Gibbs Free Energy under standard conditions ($\Delta G°$) of temperature and the concentrations or partial pressures of reactants and products. The $\Delta G°$ is calculated as the difference in Gibbs Free Energy of Formation ($\Delta G°_f$) for the products and reactants. The $\Delta G°_f$ is the $\Delta G°$ for formation of any material from the elements, i.e. graphite, $H_2$, $O_2$, for example, under standard conditions. Standard conditions means standard temperature (298.15 K unless otherwise indicated), 1 molar concentration of all solutes of reactants and products and 1 atmosphere partial pressure of gases.

Fermentation or fermentation system: refers to the use of microorganisms to produce a product for example, by digestion of biomass containing plant fiber; where the system refers to the totality of all possible reactions which occur during digestion.

Glucose equivalent: means the moles of glucose that would be linked together in a cellulose molecule. For example, 162 g of cellulose would contain one mole of glucose if it were completely hydrolysed at 100% efficiency, thus it contains 1 mole glucose equivalent. Note that the mass of 1 mole of glucose is 180 g because the hydrolysis incorporates 1 mole of water (molecular weight=18 g).

Hydrocarbons: means compounds comprised of only carbon and hydrogen and includes alkanes, alkenes, and alkynes.

Isolated microorganisms: means one or more microorganisms that either have been isolated from a natural environment and grown in culture, or that have been developed using the methodologies from the present invention and grown in culture.

Neutral Detergent Fiber or NDF: means the dry residue remaining after boiling a biomass material in pH-7 detergent for one hour, and filtering usually through a fritted glass filter under vacuum. Neutral detergent fiber is comprised of cellulose, hemicellulose, and lignin. Some denatured protein or heat-damaged protein and ash may also be included.

Mixed cultures: means more than one strain of microorganism cultured together, may be defined or undefined, pure or impure cultures.

Percent energy conserved: means the percentage of energy conserved in product such as a fuel of the energy in the feedstock used to make the product. The first law of thermodynamics requires that all energy in the feedstock be conserved in the sum of the product, other co-products and as heat produced. For example, if the energy of combustion of 1 mole of glucose in constant volume is a joules, and a process captures b joules energy in ethane produced from the glucose, the percentage energy conserved as ethane is b/a×100.

Plant fiber: is defined chemically as comprising cellulose, hemicellulose, pectin or lignin, or combination thereof, and found in plant cell wall and many forms of feedstock including whole plants, biofuel crops (e.g. switchgrass, algae), food byproducts, wood, wood byproducts, paper, waste, animal manure, human manure, and others.

Pure cultures: means cultures of microorganisms that have been isolated or partially isolated to eliminate contaminant microorganisms. Cultures can be a single strain or multiple strains (mixed cultures).

Ratio of $H_2$ to $CO_2$: means the molar ratio (similar to ratio by volume) of $H_2$ to $CO_2$ gas, that is the moles of $H_2$ gas per mole of $CO_2$ gas.

Synthesis gases: means gases used to synthesize products. In the present case these are usually carbon dioxide, carbon monoxide, and hydrogen.

Thermodynamically favorable conditions: means reaction conditions that render a reaction of interest to be thermodynamically favorable. Such reaction conditions might include pH, temperature, headspace vacuum, headspace perfusion gases or inclusion of reducing agents as well as concentrations of all reactants and products.

Thermodynamically favorable reaction: means the concentrations of reactants and products are such that the reaction is favored over other reactions.

Thermodynamically feasible: means the multiplicative product of reaction product concentrations divided by the multiplicative product of reactant concentrations is low enough for the reaction to proceed spontaneously in the forward direction under the other conditions such as temperature, pH, headspace gases.

Undefined cultures: means cultures of microorganisms taken from a source without having isolated individual microbes or characterized individual organisms.

VFA: means volatile fatty acids, which are short-chain ($C_2$ to $C_5$) carboxylic acids (e.g. acetic acid, propionic acid, butyric acid, lactic acid, isobutyric acid, valeric acid, isovaleric acid). Other names for certain VFA are propionoic for propionic, butanoic for butyric, and pentanoic for valeric.

The present invention relates to a process that produces bio-products such as hydrocarbons (e.g. alkanes, alkenes and alkynes), or other organic compounds from biomass or gases through digestion and fermentation under conditions that thermodynamically favor production of desired compounds from biomass (including, e.g., biomass comprising cellulose, hemicellulose, pectin, starch, protein, sugars, fats, acids or other combinations thereof), gases or a combination of biomass and gases. The present invention also relates to a mathematical model to determine conditions to optimize production of desired products and enrich for or select for microorganisms to produce desired products. The invention also embodies a composition of matter comprising microorganisms used in the process to digest biomass and produce desired compounds; and a process for enriching for and isolating microorganisms that can be used in the process to produce desired compounds. The invention also relates to a process to produce carboxylic acids such as volatile fatty acids (e.g. acetic acid, propionic acid, butyric acid, isobutyric acid, valeric acid, isovaleric acid) or longer carboxylic acids such as hexanoic, octonoic and decanoic acid, and odd-chain carboxylic acids and longer-chain carboxylic acids. These carboxylic acids can be made from gases ($CO_2$, CO and $H_2$) or from biomass (e.g. cellulose, hemicellulose, protein, starch, sugars, fats, other). The invention also comprises methods to produce other compounds or to degrade hydrocarbons, carboxylic acids, or other compounds. The invention also comprises methods to produce other compounds or to degrade hydrocarbons, carboxylic acids, or other compounds to shorter hydrocarbons or to $CO_2$ and $H_2$.

The current invention provides for a method to obtain and use microorganisms for production of organic compounds by applying the laws of thermodynamics to determine optimal conditions of the fermentation culture. Compared to previous processes, the current approach provides for greater efficiency in obtaining microorganisms that are able to digest certain types of feedstock (e.g. ligno-cellulose) faster and more completely, and it provides processes that are able to digest a high percentage (e.g. >50% and preferably greater than 80%) of biomass and convert it to specific products (e.g. specific volatile fatty acids, alcohols, or hydrocarbons), which are produced to a high concentration.

Application of the second law of thermodynamics to physical and chemical systems is common, and was previously disclosed in U.S. patent applications by the author (U.S. Ser. No. 61/266,610; U.S. Ser. No. 61/113,337; 12/000,856; U.S. Ser. No. 60/871,441, incorporated herein by reference), as a means to identify conditions to control a microbial ecosystem and produce biofuels. The concept as previously described can be applied to many different forms of biomass to produce many different types of products. In general, the production of a biofuel or a bioproduct by isolating a microorganism from a mixed culture of microorganisms that can use a certain feedstock and produce a number of different products is demonstrated. The process comprises analysis of the thermodynamics for all possible pathways in the mixed culture, and then removal of certain products or addition of certain reactants to make production of the favored product more thermodynamically favorable. The conditions that favor the desired product can be maintained until microorganisms that produce the product are enriched for, and from this altered mixed culture, individual microorganisms can be selected. These microorganisms can be subsequently used to digest a feedstock and produce the desired product. Likewise, mutant organisms can be enriched for until they become dominant organisms in a process of directed evolution. Even genetically engineered organisms can be selected for and the non-transformed organisms selected against by establishing thermodynamic conditions that favor the engineered organism. The biofuel or bioproduct may be an intermediate that would normally be utilized or an uncommon product produced in the mixed culture. However, altering the conditions of the culture in accordance with the thermodynamic analysis can make the product accumulate or be produced at a higher rate (more product per unit time) or greater efficiency (more product per unit substrate). Maintenance of these conditions of substrate and product concentrations can used to prevent a loss of desired activity by microorganisms by continually providing an advantage to the desired organisms.

Overview of the Process

This disclosure describes a process called "Directed Equilibrium" to control fermentation end products and to isolate microorganisms that produce desired products. This process is based on the discovery that the laws of physics, including the laws of kinetics and thermodynamics, govern fermentation pathways. The process of Directed Equilibrium uses mathematical models to establish conditions that favor production of certain desired products and to disfavor production of undesired products. The fermentation is controlled using these conditions so that the desired products are principally produced, and the organisms that produce those products are better able to survive and grow than competing organisms. As a result, the organisms that produce the desired products can be enriched for in the fermentation, and isolated and used in subsequent processes.

A similar approach has been used to isolate microorganisms that digest plant fiber (e.g. cellulose) to produce ethanol at a high concentration. This approach is also used to discover and isolate microbes that predominantly produce short-chain carboxylic acids such as butyric acid and valeric acid from carbon dioxide and hydrogen gas. Furthermore, it has been discovered that certain conditions of fermentation resulted in alkane production through decarboxylation and hydrogenation of carboxylic acids.

It is also contemplated to develop other methods to isolate microorganisms that produce medium chain alkanes from carbon dioxide and hydrogen gas. These microbes will produce the desired products or intermediates at high rates, to high concentrations, and will convert a high percentage of the gases to the desired products. The alkanes (C5 to C12) that are targeted for production will be similar in composition to the components of automotive gasoline (e.g. research octane number>85, heat of vaporization greater than 0.5 MJ/kg and energy density of greater than 40 MJ/kg). For example, hexane produced by microorganisms has been isolated using the process with conditions thermodynamically favoring hexane production.

As one embodiment of the invention, the isolation and development of microorganisms that are used for making gasoline among other products from $CO_2$ and $H_2$ are described herein. These microorganisms have the following functional attributes:

Convert $CO_2$ and $H_2$ to carboxylic acids of medium length (C5 to C10).

Convert acetate and butyrate to longer chain carboxylic acids.

Convert carboxylic acids to alkanes by hydrogenation or decarboxylation.

Convert $CO_2$ and $H_2$ directly to alkanes.

Also described herein are procedures to isolate microorganisms for the conversion of carbohydrate such as sugars or plant fiber to specific organic acids that can be converted to alkanes using organisms described herein. These organisms have the following functional characteristics.

Convert plant carbohydrates such as specific sugars or plant fiber to medium length carboxylic acids (e.g. C5 to C10).

Convert plant fiber or sugars directly to alkanes.

It has been discovered previously that many reactions are near equilibrium within fermentation and other microbial ecosystems. Therefore, the profile of products depends on the second law of thermodynamics, which orchestrates a continuous adjustment of the ecosystem to maintain a certain profile of products. As one product builds up, the organisms that produce that product can obtain less energy from producing more of it and they either stop producing it or they grow slower. As a result, the same substrate is converted to a different product in which the concentration is still low enough for the organisms that produce that different product to obtain energy. Over time the population of organisms shifts toward those better able to produce the thermodynamically favored products. The second law of thermodynamics can be used to show why fermentation proceeds to a certain profile of products and what needs to be done to change the profile of products or the microorganisms.

This discovery led to the invention of a process called "Directed Equilibrium" in which the microbial ecosystem is permitted to approach equilibrium, but certain metabolites and gases are added or removed to direct the ecosystem toward a desired equilibrium and produce more of a desired product or less of an undesired product. Directed Equilibrium process can be used to control a microbial ecosystem to convert a greater portion of substrate to a desired product, to make a higher concentration of a desired product or less of an undesired product, or to enrich or isolate certain microorganisms that produce a desired product. When the enriched or selected organisms are mutants within a culture, Directed Equilibrium process is also a means of directed evolution whereby the mutants are selected to grow in the culture.

Prior to the invention of Directed Equilibrium process, microbial isolations selected organisms that could digest a certain substrate by growing the microorganisms on that substrate, but it was not possible to select for organisms that produced certain products. The process described in this disclosure makes it possible to select for organisms that produce a certain product such as certain carboxylic acids, certain lower alkyl alcohols, or specific hydrocarbons. The selected organisms convert a greater portion of substrate to desired product at a higher concentration, and are often able to grow under these conditions.

In general, the process of Directed Equilibrium was described in detail in the inventor's previous patent applications, which are incorporated herein in their entirety by reference (U.S. Ser. No. 60/870,441; U.S. Ser. No. 12/000,856; U.S. Ser. No. 61/113,337; U.S. Ser. No. 12/385,215; U.S. Ser. No. 61/165,654; U.S. Ser. No. 61/165,654; PCT/US2010/029707; U.S. Ser. No. 61/266,610; U.S. Ser. No. 61/328,368).

Overview of Directed Equilibrium

The concept that many reactions in microbial ecosystems are near equilibrium has not been widely published or accepted. However, the change in free energy (G) for many different reactions in different fermentation systems was calculated and it was found that after accounting for some energy for ATP synthesis, indeed the $\Delta G$ was near 0. The calculations further showed that some reactions are near equilibrium even with very low concentrations of some products.

In general, the steps of the process of Directed Equilibrium include any or all of the following:

1. Obtain a culture of microorganisms, which includes activity that enables the conversion of a substrate to the desired product. In nature, this culture may only produce a trace amount of the desired product, or it may not be known to produce any of the desired product at all, but it may produce a similar product that can be converted to the desired product in a few metabolic steps.
2. Incubate the feedstock that is desired for use with the microorganisms and determine all major products.
3. Determine the association of all co-products for all end products and desired end products based on the stoichiometry of balanced chemical reactions.
4. Calculate the $\Delta G$ for conversion of fermentation substrates to each observed product and the desired product. To calculate the $\Delta G$, determine the $\Delta G°$ for formation of each product and reactant from the elements. These values are typically found in textbooks. The $\Delta G°$ (the free energy under standard conditions) is determined for each reaction based on the stoichiometry of each reaction for conversion of the substrate to each product and the $G°$ of formation for products and reactants. The $\Delta G$ is determined by adjusting the $\Delta G°$ to the temperature of the fermentation, and using the actual final concentrations for each product and reactant. For each reactant in the system, the example provided in the previous disclosures and physical chemistry textbooks provide examples enabling this aspect of the invention. Although this step can be enormously helpful it may not be necessary to formally calculate equilibrium concentrations or $\Delta G$.
5. Determine alternative conditions that will shift fermentation to thermodynamically favor production of the desired product. These conditions may include inhibitors of pathways that are otherwise favored, or addition of undesired products or gases or removal of desired products or gases. This aspect of the process can be aided by using a mathematical model in a spreadsheet developed as part of the previous step. Alternatively, adding inhibitors to reactions that produce competing products (e.g. use same substrates) or adding concentrations of alternative products will favor production of the desired product. The basis of the response is the fact that the fermentation approaches equilibrium, whether it is calculated or not, so other end product concentrations prevent competing reactions.
6. Incubate the feedstock with the microorganisms while maintaining the conditions to shift the fermentation toward producing more of the desired product. This step might require continuous infusion or removal of metabolites or gases to make the desired product thermodynamically favored over other products.
7. Whereas it may be cost prohibitive to continuously maintain conditions to produce the desired product over all other products, microorganisms that produce the desired product will be enriched for over time decreasing future competition for other products. These microorganisms grow faster, so diluting all organisms repeatedly overtime results in disappearance of organisms that produce undesired products.
8. An alternative approach to the previous step is to use conditions that favor production of the desired product but which may not result in its accumulation. For example, including an ethanol-degrader in the fermentation and conditions leading to ethanol production and subsequent degradation (e.g. high $H_2$, allow $CO_2$) would manage to keep ethanol producers in the culture, and they could be further enriched or cultured in a subsequent step.
9. To select a pure culture of microorganisms to produce mainly the desired product, dilute the enriched culture serially and plate or produce a roll tube to grow them in an agar as individual colonies. Use thermodynamic conditions so that only the desired organisms can be grown. Pick colonies that grow and continue to purify them or use them under conditions wherein they can produce the desired product based on the thermodynamic model.
10. Even a pure culture of a microorganism might produce a wider array of products than desired, or may not produce a high concentration of the desired products. Directed Evolution can be conducted by subjecting the pure culture to fermentation on the feedstock to be digested or substitute feedstock while controlling the products and reactants to make it thermodynamically favorable to produce the desired product over other products. Over many successive generations, as described previously, mutant organisms will thrive and other organisms may be diluted or wash out.
11. Another aspect of the process includes growing the microorganism with a high concentration of the desired product to select for organisms that can tolerate such a high concentration. Furthermore, conditions might be used to make it thermodynamically favorable to degrade the desired product. Such organisms might be isolated while degrading a compound, and later be grown under different conditions wherein producing the product is thermodynamically favored and under those opposite conditions, the product may be produced.
12. Furthermore, the microorganisms selected can be made more tolerant to the desired product by digesting the biomass using the microorganisms in the presence of increasing concentrations of the desired product while maintaining conditions to make it favorable to continue producing the desired product in the presence of the high concentration.
13. Another aspect of the invention is the adaptation of microorganisms to continue to degrade a feedstock such as cellulose or hemicellulose even as the mono- or di-saccharide concentration increases. Enriching, isolating and developing organisms to produce higher concentrations of intermediates like sugars involves closing all other pathways for the organisms to obtain energy. The inventor proposes using inhibitors or high concentrations of different products to make it thermodynamically infeasible for the organisms to obtain energy unless it converts a high concentration of intermediate to a high concentration of product. Because of the thermodynamics, only organisms that turn off their enzyme inhibition by intermediates survive and a higher concentration of intermediate will be produced.

14. Another aspect of the invention is to use the second law of thermodynamics to analyze the fermentation system, including an industrial fermentation and each of the organisms in it, to understand what combinations of organisms can digest feeds to certain concentrations of products, and thus how to use the optimal organisms for all components of the feedstock available for the products that are desired.

15. Another aspect of the process includes combining or maintaining more than one strain of microorganism together to provide all the desired activity. The use of thermodynamic analysis can also define conditions to isolate the best strains for combinations or to define conditions to maintain combinations as will be described in examples in this disclosure. For example, one culture requires a high concentration of glucose, and another is selected to produce a high concentration of glucose.

The process of Directed Equilibrium when used to enrich and isolate microorganisms differs from previously known processes in that the microbial system is analyzed using multiple simultaneous equations based on the second law of thermodynamics to develop conditions wherein only organisms that produce a certain product can survive, or at least are more fit than undesired organisms. Previously known systems for isolating microorganisms have used the starting mixed culture and certain substrates to enrich or isolate organisms that could use those substrates, but a wide array of products could result. Often, no organisms that produce the desired product were isolated because the conditions (pH, temperature, gas composition, metabolite accumulation) selects against the desired organisms. The present invention applies a newly discovered principle that microbial ecosystems approach thermodynamic equilibrium. One aspect of the recent inventions is the application of this principle to control microbial ecosystems and enrich and select for microorganisms that produce a desired product. Using mathematical models employing the laws of thermodynamics, it is possible to select and develop microorganisms for many different processes.

Mathematical Models of Biological Systems

All chemical reactions are controlled kinetically or thermodynamically. With kinetic control, the rates of reactions depend on substrate concentrations or enzyme activities, and these enzyme activities in turn may depend on microbial growth or enzyme synthesis. The profile of products formed depends on relative rates of different competing reactions. With thermodynamic control, the rates of reactions and which pathway branches are available depend on the second law of thermodynamics. This law governs whether or not a reaction can proceed spontaneously in the forward direction based upon the concentrations of reactants and products.

Biologists have focused on controlling kinetic elements of fermentation such as enzyme function, microbial activity, gene expression, or provision of substrates. However, it has been discovered that fermentation is often controlled by thermodynamics. For example, in a mixed-culture anaerobic digester, as soon as a glucose molecule is released by digestion of cellulose there are several microbes that can transport it into their cells and metabolize it to any number of products. The amount of energy any particular organism can obtain depends on the concentration of all products of the reaction relative to all reactants. Since the free glucose concentration is very low due to competition among microorganisms in the fermentation, and the products of fermentation are removed slowly, only very efficient microbes can use the small amount of glucose at all. And they can only use it when concentrations of the products they produce are low. Therefore, when their products start to build up, they can no longer obtain energy by converting the reactant to a product, and they leave the glucose behind for another microbe that produces a different product. In this way, a constant ratio of products is produced.

In chemistry, whether or not a reaction can proceed spontaneously in the forward direction is represented by the change in Gibbs Free Energy ($\Delta G$), which can be calculated based on the ratio of products and reactants in the system. Using this calculation, a strongly negative $\Delta G$ indicates that the reaction could proceed strongly in the forward direction without the addition of energy to the system. A strongly positive value of $\Delta G$ indicates the reaction can not proceed in the forward direction without addition of energy to the system, and it may even run in the reverse direction. If one calculates the $\Delta G$ values between many of the products in the rumen of a cow assuming typical metabolite concentrations, one finds that they are usually very near to 0. This means that the products made are a function of thermodynamics. Additional products cannot be made unless the reactant concentrations increase or the product concentrations decrease. If one product increases, then substrates to produce that product increase slightly so more of a different product can be produced. Mathematical models incorporating this knowledge have been developed by solving multiple simultaneous equations using thermodynamic data to predict concentrations of products that would result. These models will be described subsequently, and they include competition for substrates and intermediates.

Using this approach, reactor conditions that favored production of methane through anaerobic digestion were discovered, and under these conditions biomass digestion and methane production were accelerated (U.S. Ser. No. 60/870,441; U.S. Ser. No. 12/000,856). Conditions were also established that shifted undefined mixed-culture fermentation from producing methane to producing hydrogen gas. Furthermore, ethanol-producing fiber-digesting microbes that produced a high concentration of ethanol were isolated (U.S. Ser. No. 61/113,337; U.S. Ser. No. 12/385,215). Microbes that could synthesize carboxylic acids from $CO_2$ and $H_2$ were also isolated, and conditions in which carboxylic acids were condensed to produce longer chain carboxylic acids were observed (PCT/US10/29707). Rumen microbes that hydrogenate and decarboxylate fatty acids to produce alkanes were discovered (U.S. Ser. No. 61/266,610). Several of these embodiments can be used to produce gasoline and other products from $CO_2$ and $H_2$ or from biomass.

It was recently discovered that microorganisms in undefined rumen contents convert carboxylic acids to alkanes under certain conditions. These organisms used two pathways for the conversion: decarboxylation and hydrogenation. For example, butyric acid was converted to propane, isobutane, and butane by organisms in rumen fluid. Later, heptanoic acid (C7) was converted to hexane by incubating with rumen microbes, showing that longer chain carboxylic acids can be converted to alkanes that are liquid at room temperature and which comprise components of gasoline. These results demonstrate the concept that altering the environment of the fermentation in accordance with the mathematical models described in this application can shift the fermentation to pathways that were not even known to exist before. The current invention also relates to isolation of some of the organisms in rumen fluid that are responsible for the conversion of carboxylic acids to alkanes.

Source of Microbes

A further innovative aspect described in this application is that organisms may be obtained from several sources that may contain such microorganisms, such as pond water, water around geothermal vents, or the rumen of a cow. Especially preferred is the fluid obtained from the rumen. The rumen is consistently warm favoring rapid metabolism and hosting $10^{10}$ organisms per ml. The high dilution rates wash out organisms that do not grow quickly. These conditions are similar to anaerobic digesters to be used for the proposed process. The rumen gas phase is largely comprised of carbon dioxide and methane with enough hydrogen to make it thermodynamically feasible to produce carboxylic acids. Rumen microbes produce several liters of hydrogen gas per day and this hydrogen is transferred among microbial species and is incorporated into methane and carboxylic acids. The mixed culture rumen microorganisms are well known to produce acetic acid from $CO_2$ and $H_2$, and these microbes also convert acetic acid to other volatile fatty acids by incorporating $CO_2$ and $H_2$ to produce propionic acid, butyric acid, and longer chain acids. About 10% of the dry mass of rumen bacteria is comprised of carboxylic acids, and rumen bacteria synthesize carboxylic acids de novo with the medium-length saturated carboxylic acids (<C16:0) comprising a high percentage of the synthesized fatty acid in cell membranes. Rumen bacteria also synthesize odd-chain carboxylic acids such as C 15:0 and C 17:0 through elongation of propionate or valerate, and branched chain carboxylic acids from elongation of isobutyric, isovaleric and 2-methyl isobutyric acid. In addition, the rumen bacterial dry mass is about 50% protein, and this protein has a high biological feeding value and would be an excellent animal feed. Microbes that produce carboxylic acids from $CO_2$ released during digestion of biomass as well as added hydrogen, as well as microbes that produce alkanes from the carboxylic acids and additional hydrogen were isolated. These results will provide solutions to critical pathways for large-scale production of carboxylic acids or alkanes for commercialization of the technology.

In mixed-culture fermentation with rumen microbes, it was discovered that all of these reactions are near equilibrium. Six-carbon carboxylic acids (e.g. caproic acid) in rumen fluid were also measured. Thus, infusion of $H_2$ and $CO_2$ into rumen fluid proportionally increased production of all VFA. However, displacement of $CO_2$ with $H_2$ principally favored the elongation of VFA (the last two reactions) as it provides a way to use $H_2$ by reduction of shorter VFA rather than reduction of $CO_2$. Thus, isolation of microorganisms from the rumen that can carry out a series of reactions in steps under conditions thermodynamically favoring the forward reactions is contemplated.

Microorganisms

One embodiment of the current invention is a composition of matter comprising pure cultures or mixed cultures of microorganisms that produce alkanes and other hydrocarbons from VFA, biomass such as cellulosic biomass, or synthesis gases. Mixed cultures of rumen microorganisms incubated under thermodynamically optimal $H_2$ to $CO_2$ ratio and under pressure (e.g. 1 to 4 atm.) produced alkanes such as ethane, propane, butane, isobutane, pentane, hexane, octane, and longer, and branched-chain alkanes. Increasing pressure and using an optimal ratio of $H_2$ to $CO_2$ over what is natural makes it thermodynamically favorable to produce and accumulate these compounds. Under these conditions, alkanes were produced. Understanding these growth conditions, organisms were isolated that also produced these compounds in pure culture under similar conditions.

Pure cultures of isolated microorganisms isolated under conditions favoring alkane production differed from each other in appearance of cultures and differed in profile of products. Microorganisms appeared to represent the kingdoms of bacteria and archaea. Isolated bacteria were more than 97% homologous with members of the genus *Actinomyces, Enterococcus, Eschericia, Clostridium, Proteus*, and *Tissierella*.

Most cultures grew on glucose or other sugars as well as on $CO_2$ and $H_2$. Many cultures formed colonies on agar plates and roll tubes, but some colonies dissolved agar or flowed within the agar matrix. Several colonies produced slime. Some cultures produced unidentified volatile liquids, which evaporated. Some cultures produced high concentrations of methane as well as specific alkanes such as ethane, propane, butane, pentane, hexane, heptane, methyl-pentane, and others. Most individual microbial isolates produced little methane but produced specific longer-chain alkanes.

A mixed culture of organisms often produces many different VFA, but pure cultures were found to often specialize. For example, one isolate produced mostly butyrate from cellulosic biomass while another mostly produced propionate. The same is true for pure cultures that produce alkanes. Although a mixed culture of organisms produces many different types of alkanes under conditions that thermodynamically favor alkane accumulation, pure cultures produce narrow profiles of alkanes. For example, one isolated culture produced only two alkanes approximate 5 to 8 carbons in length. Techniques are described to select for organisms that produce specific products. One of the advantages of the isolated pure cultures is the ability to convert a high percentage of the biomass or gases to a few desired products rather than produce many separate products.

Methods of Production, Enrichment and Isolation of Microorganisms

Much of the emphasis in recent years has been on specific genetic manipulation and transformation to engineer organisms. However, these methods are of limited value in the early stage of microbial development. First, the genotype of the newly isolated organisms is not known, and in many cases plasmids or other vectors may not have been identified. Second, the types of changes that are desired may not be understood metabolically. For example, it is more efficient to isolate organisms that are tolerant to high concentrations of the desired products (e.g. specific acids) and grow quickly or are robust, than to transform organisms. These traits are complex and may require several genetic changes, many of which are not fully understood. Therefore, it wouldn't be easy to begin specific manipulations of DNA to create the desired organism. Furthermore, it wouldn't be necessary as there are many organisms that already evolved to thrive under the conditions needed to use in an industrial process. The initial experiments focused on enrichment and isolation for obtaining organisms with the traits that are difficult to engineer, and then apply specific engineering to simpler DNA modifications later if necessary. For example, organisms that convert a high percentage of the substrate to the desired product are selected for, but if an organism produces the desired product at all, and under certain conditions can obtain energy from producing it, it may be possible through specific genetic manipulation to knock out the ability to produce undesired products later. In other words, the process that is the focus of this application is best for developing the traits that are hardest to engineer, leaving simple mutations for the end. If specific traits are altered through transformation, mathematical models can again be used to select for the successful individuals and to establish conditions that maximize the production of the desired products from reactants.

The present invention embodies a process to use microorganisms to make desired hydrocarbons, such as alkanes, alkenes and alkynes, from biomass, carboxylic acids, and $H_2$, and one of $CO_2$ or CO. This invention comprises microbial cultures shown to have the pathways to produce specific desired hydrocarbons and which may also have the ability to digest biomass including cellulose, hemicellulose, pectin, starch, protein, and others, and which may also have the ability to assimilate synthesis gases ($H_2$, $CO_2$ and CO) into organic compounds such as hydrocarbons. The invention further comprises a process using the microorganisms and process conditions that make it thermodynamically favorable to make the desired hydrocarbons from the biomass, carboxylic acids, or synthesis gases. These process conditions include certain molar ratios and pressures of gases that make the desired conversions thermodynamically favorable over other possible uses of the reactants or intermediates. The invention further comprises a mathematical model to calculate the process conditions based on the laws of thermodynamics, the potential reactants and products in the fermentation, and the stoichiometry for the efficient conversion from one set of reactants to another. The invention further comprises a process to isolate and improve microorganisms to be used in the process by further applying conditions determined by the mathematical model.

Conversion of carboxylic acids to hydrocarbons while capturing Gibbs Free Energy requires the $\Delta G$ for the conversion to be negative. A specific molar ratio of $H_2$ to $CO_2$ (e.g. 3) and pressures greater than 1 atm make the reactions to produce alkanes thermodynamically feasible while capturing energy as ATP. Pressures greater to 2 atm and more preferably greater than 4 atm may be preferred. Even higher pressures such as 8 or 15 atm further shift the equilibrium toward longer chain alkanes or longer chain carboxylic acids. However, vacuum pressures, such as about 0.05 atm, favor certain reactions such as decarboxylation of carboxylic acids in the fermentation and therefore can also yield alkanes when carboxylic acids are present. Such low pressures also favor degradation of carboxylic acids and decrease production of carboxylic acids from biomass. Thus, the compete set of conditions needs to be defined in accordance with how it affects the $\Delta G$ of the desired conversions. Wherein, many microorganisms can be isolated to digest biomass to carboxylic acids, under conditions wherein the conversion of carboxylic acids to hydrocarbons is thermodynamically feasible, these same organisms or symbiotic organisms can use the carboxylic acids to make hydrocarbons like alkanes. Organisms can also convert $H_2$ and $CO_2$ to hydrocarbons under conditions wherein it is thermodynamically feasible. In addition, $H_2$ and CO can be converted to alkanes or other hydrocarbons by similar organisms because $CO+H_2$ and $CO_2$ are readily inter-converted. Thus, the optimal ratio for alkane production from $H_2$ and CO would be 2 and the effect of increased pressure is similar.

Organisms can produce some products that are not thermodynamically favorable when considering only the single reaction that produces that product. The overall $\Delta G$ of all linked reactions must be negative, but the conversion of ATP to ADP or conversion of some other high-energy intermediate to a lower-energy product could be linked to the production of desired product. It may be possible to isolate organisms that produce trace quantities of a desired product, such as an alcohol or alkane, even without establishing conditions that make it possible for the organisms to capture Gibbs Free Energy from carrying out the reaction. However, it is particularly advantageous to establish conditions in which the organisms that produce the desired products grow faster, or capture more Gibbs Free Energy, than competing organisms, while producing the desired product. Doing this requires attention to concentrations of reactants and products in the culture so that the desired reaction is thermodynamically feasible and thermodynamically favorable. If a certain product is found in a fermentation, it is known that the combination of reactions leading up to that product were thermodynamically feasible, but using analysis of thermodynamics makes it possible to establish conditions that make it possible to make the product while allowing organisms to grow from the Gibbs Free Energy they capture from making it or to make the product in a high concentration. For example, microbes were previously isolated that could produce trace quantities of ethanol from $CO_2$ and $H_2$, but producing a high concentration of ethanol while allowing the organisms to grow is promoted by higher partial pressures (e.g. greater than 1 or 2 atm) and certain ratios of gases (e.g. $H_2$ to $CO_2$), and the combination of conditions needed or acceptable can be determined according to thermodynamics.

Often researchers describe development of organisms to produce specific products but the products are not produced in high concentrations or the organisms do not survive. For example, genetic engineers can put genes into an organism to produce a certain fuel. Even if the genes are expressed, the enzymes may not catalyze the desired reactions in the forward direction, or there may be no advantage to the organisms that do, unless the conditions of the fermentation including reactant and product concentrations are such that the desired pathway is thermodynamically favorable and feasible. Thus, one embodiment of the current invention is the establishment of conditions that make it possible to use microbes that produce desired products including hydrocarbons under conditions wherein it is thermodynamically feasible and favorable to produce those products while capturing energy for microbial growth.

The procedures described in U.S. Ser. No. 61/113,337, U.S. Ser. No. 12/385,215 and PCT/US2010/029707 were used for calculation of $\Delta G$ for reactions, in vitro fermentations, enrichments, and isolation of microorganisms except for modifications described in this application. The type of feedstock that can be used, the laboratory analysis of feedstock, and the industrial process described in U.S. Ser. No. 61/113,337, U.S. Ser. No. 12/385,215 and PCT/US2010/029707 for production of alkyl alcohols also apply to the methods to produce volatile fatty acids, alkanes or any other type of fermentation reaction to produce a product. The previously described methods are incorporated herein by reference and will not be repeated completely.

Standard Microbiological Procedures

Generally, microbial selection is preceded with enrichment of organisms with desired traits. Organisms that have desired functional traits are enriched under specific conditions for several periods of growth followed by sub-culturing and dilution. For example, conditions may be created that favor alkane production so that only the alkane producers grow quickly. Selective media are inoculated with a mixed culture and incubated under those conditions for two to five days. A culture starting with $10^8$ viable cells per ml may end with $10^{10}$ cells per ml, and 99% of the new cells will have grown recently under the restrictive conditions. Therefore if a rare organism in the original culture thrives under highly restrictive conditions, it will dominate the new culture. For example, one in a million organisms, or 100 in a hundred million, would make up 99% of the culture after one enrichment phase if the conditions are such that only those organisms can grow. If the conditions only favor desired organisms, but do not completely exclude competitors, it takes several iterations of culturing and sub-culturing to reach a steady state in which more organisms with the desired traits exist in the culture compared with the initial conditions. We typically use a few to more than 10 separate enrichment steps.

Often different conditions are used in alternating enrichment steps. One set of conditions may be used to select for a certain functional trait, and a second set of conditions used sequentially for a second functional trait. For example, if organisms that produce liquid alkanes are desired, one set of conditions to select for medium-chain carboxylic acids (e.g. $C_6$ to $C_{12}$) and a second set of conditions that favor alkanes over acids. The result will be organisms that can produce both medium-chain acids and alkanes. Some of these organisms will produce alkanes of length $C_6$ to $C_{10}$ via decarboxylation or hydrogenation of the acids they also produce.

Once the desired traits have been enriched for, individual strains of organisms are selected. Serial dilutions from 1 to $10^{-14}$ are poured to agar plates, which are incubated under restrictive conditions. Agar plates are incubated with specific gas compositions and pressures. Roll tubes can also be used at times to apply certain types of gas composition. For roll tubes, warm agar is inoculated in test tubes, which are sealed and rolled on ice to make the agar gel. The agar hardens around the perimeter of the tube. Both agar plates and roll tubes typically are incubated at 40° C. until discernable colonies form, usually within one to three days.

Colonies are picked from the tubes and plates using sterile technique. The plates and tubes with less diluted inoculation have overlapping colonies, while the ones that are highly diluted do not have any colonies. Some plates have individual colonies, and these are added to a sterilized broth and incubated under conditions to favor production of the desired product. 32-liter canning pressure cookers are used as anaerobic chambers. Several racks of test tubes or agar plates can be added to the chambers with adequate headspace so that gases do not need to be changed more than once a day. The chambers support up to 3 atmospheres of gas infused through a valve into the chamber. In addition, the leading organisms are incubated in tubes or flasks with gases bubbled into each fermentation using small aquarium pumps inside the chamber, or incubations are carried out in Wheaton bottles in a shaking bath or shaking incubator.

The products each strain produces are screened sometimes using rapid procedures (e.g. visual appraisal of carboxylic acid or alkane layer after centrifugation at low speed), and leading candidates are analyzed for several products using gas chromatography (GC). After an initial screening of all isolates, the most promising strains are further evaluated by determining the optimal conditions for their growth (e.g. pH, temperature, substrates, oxygen), and the rate of growth (g/L per day), sensitivity to end products (e.g. acids, alkanes, alcohols).

Following this process which typically isolates and evaluates a few hundred to a few thousand organisms each run, the results are evaluated to determine which end products and metabolic pathways dominate for each strain. Once the best cultures are selected and evaluated under many different conditions, the growth rate, production rate, conversion efficiencies (percent of $CO_2$ and $H_2$ conversion to different products), titer and tolerance to potential end products are determined.

After evaluation of the leading strains and identification of the potential weaknesses of any leading strain, a process of mutagenesis is initiated. In this process, the conditions in which the desired products are strongly favored are used on separate pure cultures of large numbers of organisms (e.g. $10^{10}$) of a strain. Conditions are established in which production of desired products are favored and production of undesired products are strongly disfavored. For example, if an organism only produces a few products, conditions to select against the few undesired products are focused on. A range of conditions is used to both favor desired organisms and disfavor undesired ones. No organisms will grow under many sets of conditions, while under other conditions a few grow and they will take over the culture. The survivors are enriched again under even more restrictive conditions. In this way, only the mutants that have special abilities within the originally pure culture survive. To increase the genetic diversity, some cultures are exposed to different levels of ultraviolet light or other mutagen briefly at the beginning of the incubation. The treatment increases mutation rate and accelerates the evolutionary process. The developed organisms are selected on agar plates and tested as previously. Thus, the entire process of enrichment and selection may be repeated many times for both original selection and development.

Conditions for Alkane Production

A typical in vitro fermentation can be used as described previously (Goering and Van Soest, 1970) but with substitution for bicarbonate buffers, and using rumen microorganisms or any similar source of microorganisms. Typically, buffers will be added with a source of biomass to maintain neutral pH. The biomass could be plant fiber (e.g. AVICEL® microcrystalline cellulose, carboxymethyl cellulose, timothy hay, timothy ADF) or an intermediate like a volatile fatty acid. The incubation must be conducted under high concentration of hydrogen and low concentration of $CO_2$. These conditions shift fermentation toward decarboxylation and hydrogenation. The alkanes can be measured by gas chromatography.

Aside from incubating in the presence of a high concentration of $H_2$, other gas headspace could also favor alkane production. High $N_2$ perfusion would lead to an increase in $H_2$ concentration as the $CO_2$ is diluted. Applying vacuum pressure would remove lower alkanes and increase $H_2$ by decreasing $CO_2$. Perfusion and removal of $H_2$ would remove the volatile short-chain alkanes and further shift equilibrium to greater alkane production. The low $CO_2$ and high $H_2$ could also increase alkane production. High methane perfusion could also result in high alkane production because the methane concentration would inhibit the alkane production.

In the preliminary experiments, alkanes were produced from volatile fatty acids when incubating in $N_2$, $H_2$, vacuum or even $CO_2$. The incubation in vacuum resulted in the highest concentration of alkanes (ethane, propane, butane, pentane, higher length were not measured). However, the lower amount of gas in the headspace for the vacuum treatment means the actual gas production was not higher. The hydrogen treatment resulted in the highest alkane production. The results from this application of the process of Directed Equilibrium were surprising because that fact that such organisms exist in the rumen or anywhere was unknown. However, now that it is known that such organisms exist in anaerobic microbial cultures, and the conditions to favor these microorganisms have been determined, it will be possible to isolate such organisms from these cultures and to use them in pre cultures to convert biomass to alkanes.

Isolation of Alkane-Producing Microorganisms

Having established that alkanes are produced by microorganisms from the rumen, and the conditions to favor alkane production, it is possible to isolate the responsible organisms and improve them by incubating under conditions favoring greater alkane production. For example, alkane producers could be enriched by incubating volatile fatty acids with high concentrations of hydrogen, and then selecting colonies from roll tubes with acids as the energy source in the presence of hydrogen.

In some cases, fermentations that produce a mixture of alkanes are preferred, wherein production of a predominant alkane may be preferred in other cases. Uniform fermentation results in a product that may be easier to separate (e.g. only one boiling point) or burned (e.g. only one flash point). A mixture of alkanes can also be used however and may be preferred if the fermentation is faster and cheaper or requires less sterilization.

Industrial Production of Alkanes

The industrial production of alkanes as a biofuel is contemplated. If pure cultures of microorganisms are used, the cultures isolated previously would be used. The biomass would be sterilized by heating, possibly under pressure, and transferring to the digester. Other methods of sterilization such as use of chemicals are contemplated. A culture of microorganisms that digests the biomass and converts it to alkanes would be added. It may take one set of organisms that produces a certain volatile fatty acid, or mixture of acids from the biomass and another set that converts the acids to alkanes. An organism that elongates volatile fatty acids, such as an isolate discussed herein, might also be used to produce a longer-chain alkane. The biomass might be cellulose biomass like paper or grass. Once certain microorganisms have been isolated for the process, without the competition from other organisms that would exist in a natural population, the conditions could be relaxed and alkanes still be produced. For example, $N_2$ or partial vacuum might be used to replace $H_2$ that would be used for microbial selection. As long as the desired reactions are thermodynamically feasible, it would not be necessary to inhibit other reactions. In this way alkanes would be produced and could be removed as gas, or if longer-chain alkane through extraction, distillation or diffusion process. These alkanes can be used directly in gasoline or diesel or shorter chain alkanes used fuels as compressed gases.

An alternative approach would be to use a mixed population of microorganisms like rumen microorganisms or single pure cultures to produce volatile fatty acids from biomass, and then convert the acids to other fuels in a subsequent process. For example, a chemical process can be used and the final biomass could be an alcohol or an alkane, including an alkane longer than one carbon. This approach was contemplated previously in U.S. Ser. No. 60/870,441 and U.S. Ser. No. 12/000,856. In summary: It was discovered that alkanes can be produced by microorganisms from biomass in a mater of a few days incubation under the correct conditions. They have discovered these organisms exist in the rumen of a cow among other places. They have established the conditions (e.g. high H2 and low $CO_2$) that shift the fermentation to produce the alkanes, and these conditions can be used to isolate the organisms that carry out the reactions. Using the process of Directed Equilibrium, alkane-producing organisms can be selected and used to produce alkanes from biomass.

Use of Mathematical Models

Methods of microbial isolation and development using mathematical models of fermentation have been improved. The models simultaneously use both laws of thermodynamics and kinetics, and solve simultaneous equations representing multiple pathways. These models predict the consequences of competition for substrates, and determine conditions in which organisms that obtain energy from a certain pathway will or will not be able to grow from those pathways.

One example shown in FIGS. 1 to 3 relates to the Gibbs Free Energy change ($\Delta G$) for different reactions that can produce products from $CO_2$ and $H_2$. If the $\Delta G$ is negative, the reaction can proceed in the forward direction spontaneously. The most negative $\Delta G$ represents the reaction with the most favorable conditions to carry out the reaction. Reactions with positive $\Delta G$ can proceed in the forward direction, but only if energy is put into the system to drive the reaction forward. In other words, another linked reaction with an even greater absolute value of $\Delta G$ that is negative must be linked to make the overall $\Delta G$ negative. For end products relative to reactants like $CO_2$ and $H_2$, a positive $\Delta G$ means the organisms that carry out the reaction will have to use their own energy to make the reaction proceed. If an organism is using energy to make the product, it will not be able to grow from carrying out the reaction. On the other hand, an organism that carries out a reaction under conditions with very strongly negative $\Delta G$ will not only be able to carry out the reaction without using its energy stores, it will also be able to link ATP generation or other storage of energy. Thus, the strongly negative $\Delta G$ will allow for the fastest growth rates (particularly with the types of organisms we are discussing because the energy can be generated from dissipation of proton gradients in continuous fractions of ATP).

This model to enrich and isolate organisms that produce long-chain carboxylic acids or alkanes in a high concentration, and that does not produce as much acetic acid or methane, is used. The calculated $\Delta G$ depends on the ratio of products to reactants, and the $\Delta G$ for several different potential pathways is calculated. There are two manipulations to fermentation that particularly change which products are favored. The first is the ratio of $H_2$ to $CO_2$, and the second is the combined pressure of both gases. The optimal ratio to produce acetic acid is 2:1, but the optimal ratio to produce alkanes or long-chain carboxylic acids approaches 3:1. The optimal ratio to convert acetate to propionate is 3:1. In all cases, increasing the total pressure of $H_2$ and $CO_2$, especially at the optimal ratio, exponentially favors alkanes and long-chain acids over acetate. For example, at twice the pressure, the equilibrium concentration of acetate doubles, but the equilibrium concentration of long-chain acids or alkanes increases four fold. Thus, incubation under moderate pressures of optimal ratios of $H_2$ and $CO_2$ shifts equilibrium toward desired products and in fact, organisms that produce those products will be favored. Different conditions favor elongation of acids, decarboxylation or hydrogenation. Carboxylic acid elongation and hydrogenation are favored by high $H_2$ pressure. Decarboxylation is favored by low $CO_2$ pressure. These procedures have been used and the empirical results confirmed the theoretical expectations.

In addition to these procedures to favor organisms that produce these desired products, metabolic models point to several other ways to further select desired organisms. One surprising approach to obtain organisms that carry out a desired conversion reaction (e.g. A→B) is to isolate organisms that carry out the reverse of the desired pathway (e.g. B→A). In other words, enrich them under conditions that start with a high concentration of the desired product and favor degradation of the product. In a subsequent phase, the desired product is removed and the thermodynamic conditions are reversed. The resulting organisms can create the desired product under one set of conditions and degrade it under another set. This approach applied to enrichment of organisms selects for a high degree of tolerance to the desired product (only organisms that grow in a high concentration survive) and a high specificity of production (selected organisms have the enzymes to make or degrade the desired product). It is based on the theory that all catalysts decrease activation energy of reactions, they do not change the equilibrium constant or $\Delta G$. Catalysts such as enzymes accelerate the rate of reactions when those reactions are kinetically controlled, but they must also accelerate the rate of the reverse reactions to an equal proportion (Chang, 1981. Physical Chemistry with Applications to Biological Systems. MacMillan Publ. Co., Inc., New York which is incorporated herein by reference). Otherwise the equilibrium constant would change. A corollary to this principle is that all catalyzed reactions are bi-directional. If enzymes to catalyze a given reaction are desired, for example to produce butanol, organisms that degrade butanol have those enzymes. The cell machinery may not be set up to allow the organisms to grow (produce ATP) under both sets of conditions, but this is often the case. Alternatively, the genes encoding the enzymes to degrade a compound can be used to transform another organism to make the product that the gene donor organism degraded.

A further application of the model to establish conditions for enrichment pertains to using aerobic conditions in the enrichment phase. Many organisms can aerobically catabolize a substrate like glucose to $CO_2$ and $H_2O$. However, they may also survive under anaerobic conditions by making another end product that does not require oxidation. For example, they may make acetate and $H_2$ or ethanol or lactate. If oxygen is returned to the environment, they may further oxidize these "end products" to $CO_2$ and $H_2O$ for additional energy. Thus, it is advantageous to isolate such facultative aerobes by growing them in the presence of oxygen and high concentrations of the desired product. For example, this technique isolates organisms that produce caproic acid (a.k.a. hexanoic acid, $C_6H_{11}COOH$) or isovaleric acid (a.k.a. 3-methyl butanoic acid, $C_5H_9COOH$). In one phase of the enrichment, the acid is oxidized to $CO_2$ and $H_2O$, and in the other phase organisms are grown under conditions to favor production of the desired acid from $H_2$ and $CO_2$. There are special advantages of facultative aerobes. They can be grown aerobically very quickly while only producing $CO_2$ and $H_2O$, which can be easily removed. Even facultative anaerobes are advantageous because of their ease of handing in the laboratory.

Without understanding that enzyme-catalyzed reactions are bi-directional it would not be apparent that growing microbes under conditions to degrade certain products would enrich for microbes that can also produce the products. However, the approach has now been used to produce several different products from $CO_2$ and $H_2$. For example, organisms were isolated that convert $CO_2$ and $H_2$ to high concentrations of ethanol or butyrate, among others. Also, microbes were grown on iso-octane under conditions to degrade it, and then organisms were isolated that could synthesize hydrocarbon compounds similar in size and composition to iso-octane under 2 to 4 atm. pressure of gases comprising $H_2$ and $CO_2$ in a molar ratio of 3. In addition, other enrichment strategies are also used. Organisms that are isolated that can degrade a certain product can be used as a source of material to genetically transform organisms to make those products because all metabolic pathways are bi-directional.

Source of Microbes

Although any anaerobic fermentation, and even aerobic microbial ecosystems, may be an adequate source of microbes, the rumen (or first stomach chamber) of a cow is especially advantageous. The rumen is consistently warm favoring rapid metabolism and hosting $10^{10}$ organisms per ml. The high dilution rates wash out organisms that do not grow quickly. These conditions are similar to anaerobic digesters to be used for the proposed process. The rumen gas phase is largely comprised of carbon dioxide and methane with enough hydrogen to make it thermodynamically feasible to produce carboxylic acids. Rumen microbes produce several liters of hydrogen gas per day and this hydrogen is transferred among microbial species and is incorporated into methane and carboxylic acids. The mixed culture rumen microorganisms are well known to produce acetic acid from $CO_2$ and $H_2$, and these microbes also convert acetic acid to other volatile fatty acids by incorporating $CO_2$ and $H_2$ to produce propionic acid, butyric acid, and longer chain acids. Microbes that produce carboxylic acids from $CO_2$ released during digestion of biomass as well as added hydrogen, as well as microbes that produce alkanes from the carboxylic acids and additional hydrogen, have been isolated. Rumen microbes are also highly adapted to rapidly digest many different forms of biomass including ligno-cellulose.

Other sources of microbes can also be used with the described process. These sources include other anaerobic or aerobic microbial consortia. For example, silage, soil, biomass digester, compost, sludge, soil, or alcoholic beverages may also be sources of microbes. Organisms that can degrade carboxylic acids to $CO_2$ and $H_2$ may also be able to produce carboxylic acids from $CO_2$ and $H_2$. Therefore, sources of carboxylic acid degradation, such as rotting fats may also provide organisms. In particular, spoiled milk products may be particularly suitable for isolating degraders and therefore producers of medium length carboxylic acids because milk contains many of such acids. Likewise, organisms that degrade alkanes such as petroleum products may also produce alkanes from acids. Thus, contaminants of gasoline or organisms in diluted petroleum products may also contain adequate microbes. Organisms from water bodies, including organisms that live near hydrothermal vents, may be particularly useful because hydrothermal vents release gases that are synthesized to organic compounds and these gases are under pressure due to water depth. Organisms that may already have been isolated but were not used with the process described in this application may also be used. For example, organisms that degrade carboxylic acids or alkanes, including organisms that are used to clean up oil spills, may also be adequate for the described process to make alkanes or carboxylic acids under thermodynamic conditions that favor synthesis over degradation.

Digestion and Fermentation

In vitro digestion of various feedstock is orchestrated according to the example of H. K. Goering and P. J. Van Soest, 1970 (Agricultural Handbook No. 379 entitled Forage Fiber Analyses (Apparatus, Reagents, Procedures, and Some Applications, Agricultural Research Service of the United States Department of Agriculture), which is incorporated by reference). Media are as described for in vitro digestion by Goering and Van Soest (as cited) but the bicarbonate salts are replaced with phosphate salts when not using carbon dioxide as the headspace gas. Macro minerals, microminerals, tryptic digest of casein, ammonia, sulfide, and cystein reducing agents, and resazurinare used according to Goering and Van Soest (as cited). These digestions are typically carried out in flasks or test tubes under anaerobic conditions in a water bath at 39° C., but sometimes are under aerobic conditions, and other temperatures are used in the range from 25° C. to 55° C. Even warmer or cooler temperatures could be used.

Enrichment

In addition to the procedures described in U.S. Ser. No. 61/113,337, U.S. Ser. No. 12/385,215, and PCT/US2010/

029707, which are incorporated herein by reference, for enrichment and isolation of microorganisms, the additional conditions for enrichment and isolation outlined below are used. Example media for enrichment, isolation, screening and initial experiments is as described for in vitro digestion by Goering and Van Soest, "Forage fiber analyses (apparatus, reagents, procedures, and some applications)." Agricultural Handbook Number 379, Agricultural Research Service, USDA, Washington D.C., but the bicarbonate salts were replaced with phosphate salts when not using carbon dioxide as the headspace gas. Macro minerals, microminerals, tryptic digest of casein, ammonia, sulfide, and cystein reducing agents, and resazurin can be used according to Goering and Van Soest (as cited). Media are typically boiled under 1 atm $CO_2$ or $N_2$ (for $H_2$ preparations). The same media formula can be used for initial enrichment, agar roll tubes, broths, slant tubes, and agar plates. However, roll tubes, slant tubes and agar plates also contain 2% agar gel (BactoAgar). Media used for pure cultures (everything but the initial enrichments) can be combined with 20% autoclaved rumen fluid to provide potential unknown growth factors.

Media usually contain 2% of the form of carbohydrate as timothy hay, timothy NDF, timothy ADF, AVICEL® microcrystalline cellulose, filter paper, or carboxymethyl cellulose. In other cases, the source of energy is VFA, and in other cases only synthesis gases (e.g. $CO_2$ and $H_2$) provide energy to select for organisms that grow on synthesis gases. The rationale for the different sources of carbohydrate or other source of energy is to enrich for microorganisms that can digest and utilize the type of carbohydrate for energy. For example, to obtain organisms to digest grass ligno-cellulose, timothy ADF can be used. This source has little energy other than the ligno-cellulose so that other organisms would not grow well.

Media (45 ml) are transferred to each 140-ml bottle under perfusion of gas. Rumen fluid from the cows' rumen or other source of bacteria can be prepared by blending for 1 minute and straining through cheese cloth followed by glass wool. Carbon dioxide or nitrogen, when used as the headspace gases, are often run through a copper column to remove residual $O_2$ before being perfused over rumen contents and into containers to maintain anaerobic conditions. Rumen inocula (5 ml) is added to each flask. Flasks are sealed with butyl rubber stoppers and incubated in a shaking water bath for 48 hours. To prevent wash out of some slower growing microorganisms, each enrichment is sometimes carried out for greater than 48 h. New flasks are prepared with 45 ml of media with additional carbohydrate, and 5 ml of subculture are added from the previous fermentation. These flasks are again incubated for 48 h, and again sub-sampled. Each enrichment process typically includes at least three cycles of sub-culturing and growth. For each enrichment and roll tube, the temperature of incubation is typically 39° C. unless indicated otherwise. Some enrichments occur at 25° C. or 55° C. and other temperatures can be used in particular to select or organisms or enzyme that are tolerant and efficient at different temperatures.

The enrichments are conducted while maintaining conditions to favor enrichment of the microorganisms of interest. Such conditions are defined for specific examples that follow. In general, provision of undesired products (e.g. VFA, gases) in the fermentation shifts metabolism against further production of those products because the fermentations are near equilibrium. Therefore, the desired products are maintained in low concentration relative to the other products to increase further production of only the desired products. The knowledge of the stoichiometry of the reactions leading to the desired or undesired products is used to supply several different undesired products as once. For example, gaseous co-products are added or removed to drive enrichment of organisms that either do not produce or do produce those gases along with other metabolites. Inhibitors of certain pathways like methanogenesis or hydrogen transport are also used based on the knowledge obtained from the mathematical model that highlights the need to inhibit certain pathways to favor certain products.

Isolation

Isolation of microorganisms generally follows the description in U.S. Ser. No. 61/113,337, U.S. Ser. No. 12/385,215 and PCT/US2010/029707, all by the inventor and which are incorporated by reference for isolation of microorganisms to produce ethanol from plant fiber, except modifications are made to select for organisms that are more likely to produce a certain acid (e.g. propionic acid), or produce an alkane greater than one-carbon in length. Specific modifications to isolate organisms that produce each type of product are provided as examples.

Isolation of individual microorganism strains used common practices in microbiology except for the addition of metabolites (aqueous and gaseous) or inhibitors to prevent production of undesired products and to drive the fermentation toward desired products and organisms that produce them. Media was as described for in vitro digestion by Goering and Van Soest (1970) but the bicarbonate salts were replaced with phosphate salts when not using carbon dioxide as the head space gas. Macro minerals, microminerals, tryptic digest of casein, ammonia, sulfide, and cystein reducing agents, and resazurin are used according to Goering and Van Soest (1970).

Media are boiled under 1 atm $CO_2$ or $N_2$ (for $H_2$ preparations). The same media formulae are used for initial enrichment, agar roll tubes, broths, slant tubes, and agar plates. However, roll tubes, slant tubes and agar plates also contained 2% agar gel (BactoAgar). Media used for pure cultures (everything but the initial enrichments) are combined with 20% autoclaved rumen fluid to provide potential unknown growth factors.

Sterile roll tubes or plates are used to isolate colonies from sources of microorganisms with or without enrichment. The media are transferred to sterile tubes or plates while still hot from boiling. Tubes are cooled to 55° C. and inoculated. The microbial inoculais diluted serially in media to obtain cultures from 1 to $10^{-14}$ viable cells per 0.5 ml inocula. Roll tubes are prepared for each level of dilution, but concentrating on the dilutions best able to separate individual cells depending on the source. Once inoculated, tubes are perfused with gas, stoppered, and rolled on ice to make the gel harden. Plates are incubated in anaerobic chambers under $N_2$ and 5% $H_2$, or in air. Roll tubes are especially used for $H_2$, CO or mixed gases when a number of different gas mixes are desired or the gases might be toxic or dangerous if leaked in large quantity. Tubes and plates are incubated for 24 to 48 h at 39° C. and independent colonies selected from these.

Maintenance

Colonies are selected from among the colonies in roll tubes and transferred to broth for short-term maintenance. The broth is of the same composition as media for other purposes, but does not contain agar, and contains a source of energy such as 0.8% cellobiose, Avicel, filter paper, timothy hay, or gases. Once the tubes for broth are prepared and stoppered, they are autoclaved before use. The microbial inocula is added using a sterile needle. Broth cultures are maintained at 39° C. until they become cloudy. Broth cultures (5% final concentration, vol/vol) are transferred to new media three times per week. After two to three cultures, 0.1 ml culture is transferred to a slant culture (2% agar media with new energy source in a 25-ml tube with 10 ml media on a slant to increase surface area. The inocula added on top the agar which is maintained under $CO_2$, $N_2$ or $H_2$ or other gas as needed for the type of culture. These are initially incubated at 39° C. until colonies form (16 h), and then stored at 25° C. or 4° C. for up to a month. Cloudy broth cultures are also stored by adding 30% glycerol (final volume) and freezing in liquid nitrogen; once frozen, these colonies are stored at −80° C.

Sterile conditions are used for pure cultures that digest pure or artificial feedstock. Media are added to Wheaton bottles or tubes with an energy source and other nutrients, the containers stoppered and autoclaved. The inocula are added through the stopper with a sterile needle.

Screening

Screening of microorganisms addresses whether they can use a certain substrate and convert it to desired product. For ease of use, soluble cellobiose or AVICEL® microcrystalline cellulose are frequently used. Cellobiose is a two-glucose unit of cellulose used by many fiber digesters. However, AVICEL® microcrystalline cellulose is a better indicator of the ability to digest more complex sources of plant fiber. The inventor also screens for fiber digestion using filter paper or timothy hay wherein the disappearance of the NDF or ADF indicates fiber digestion. The disappearance of filter paper is visible after one day. Other sources of fiber (e.g. algae) may be desired when organisms are needed for a certain feedstock. Previous isolates (U.S. Ser. No. 12/385,215) were screened for digestion using AVICEL® microcrystalline cellulose and timothy hay (NDF disappearance measured). New isolates from AVICEL® microcyrstalline cellulose or carboxymethyl cellulose in the roll tubes are also screened this way, with a higher percentage of successful fiber digesters. In fact, high fiber digestion is a property of nearly all isolates from a source of fiber in the roll tube or plate used for isolation. Screening is also performed using alcohols in the tube to determine the ability to digest fiber in the presence of a high concentration of alcohol (e.g. 6 or 10% by volume), or a high concentration of a certain VFA (e.g. 2% acetate). Screening of organisms that produce an organic compound from synthesis gases is undertaken by growing the organisms in the presence of the optimal concentration of those gases for production of the desired organic compound no other energy source and measuring all products and the remainder of gases. Cell growth is measured by changes in optical density, especially when the energy source does not interfere. After the digestion in these various substrates for a period of one to 5 days, the VFA, alcohols and alkanes are measured by gas chromatography. Results indicate that several species can convert a natural (e.g. timothy hay) or pure (Avicel) source of plant fiber to predominantly produce a desired product such as a single VFA or only a few alkanes.

Screening also involves defining each organism by the substrate it can use and the products it can produce. The second law of thermodynamics is used to provide a framework which is parameterized through in vitro experimentation. For example, based on the second law of theirmodynamics and the knowledge that it applies to many products of fermentation, we know that the final concentration of a product depends upon the concentrations of other products and reactants. Thus, experiments can be undertaken to incubate organisms with defined concentrations of substrates and the equilibrium (final) concentrations of each product and substrate determined. These data can then be used to determine which organisms to use in what combinations to optimally produce the product. For example, organism X can generate 1 mM cellobiose from cellulose, and organisms Y will convert that to up to 8% ethanol.

Mathematical Model of Hydrocarbon Production

Balanced chemical equations were derived for conversion of glucose, VFA, or $CO_2$, CO, and $H_2$ to alkanes or other hydrocarbons. Alkanes greater than one carbon in length were previously thought to be produced by high temperatures and pressures over geological time (e.g. millions of years). It has been discovered that microorganisms can produce alkanes from fatty acids in a matter of hours. Thus, for example it has been observed that an acid such as butyric acid ($CH_3CH_2CH_2COOH$) gave rise to propane ($CH_3CH_2CH_3$) and butane ($CH_3CH_2CH_2CH_3$) and iso-butane ($CH_3CHCH_3CH_3$). Based on the products and the reactants, the stoichiometry can be understood. For example, to produce propane from propionate, a product may be $CO_2$ which balances C, H, and O. To produce butane or iso-butane, $H_2$ may be a reactant and $H_2O$ a product.

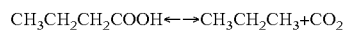

$$CH_3CH_2CH_2COOH \longleftrightarrow CH_3CH_2CH_3 + CO_2$$

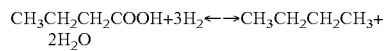

$$CH_3CH_2CH_2COOH + 3H_2 \longleftrightarrow CH_3CH_2CH_2CH_3 + 2H_2O$$

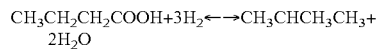

$$CH_3CH_2CH_2COOH + 3H_2 \longleftrightarrow CH_3CHCH_3CH_3 + 2H_2O$$

Thus, the balanced equations can be determined. The respective pathways are determined for any and every reaction thought to occur in the fermentation system of interest. The production of various VFA from synthesis gases was known, so once conversion of VFA to alkanes was discovered, the conversion of synthesis gases to alkanes was initially assumed. For example, $4CO_2 + 13H_2 \longleftrightarrow CH_3CH_2CH_2CH_3 + 8H_2O$ was thought to produce butane under appropriate conditions. Using this stoichiometry, the conditions needed for the desired pathway to be thermodynamically feasible or thermodynamically favorable were determined. When microorganisms of various sources were incubated under these conditions, the desired pathway was enabled to produce the desired product (butane and other alkanes in this case). The production of butane from the synthesis gases confirmed the presence of the desired pathway or similar pathway.

The change in Gibbs Free Energy under standard conditions ($\Delta G°$) was determined in the established way of calculating the Gibbs Free Energy of Formation from the basic elements for each reactant and product and subtracting the Gibbs Free Energy of Formation of the products from the Gibbs Free Energy of Formation of the reactants (Chang, R. 1981. Physical Chemistry with Applications to Biological Systems: Second Edition, MacMillan Publishing Co., Inc., New York). The Gibbs Free Energy of Formation values not found in the book authored by Chang were obtained from the literature (Guthrie, J. Peter; 1992. A group equivalents scheme for free energies of formation of organic compounds in aqueous solution. Canadian J. Chemistry 70:1042-1054). The relevant values from the literature are provided again in Table 1. Similar information can be obtained from these references and others if desired to add other metabolites to the model.

The values in Table 1 are the key thermodynamic data under standard conditions for these reactants and products as well as some other important potential fermentation intermediates. These values represent the Gibbs Free Energy of formation ($\Delta G°_f$) and enthalpy of formation ($\Delta H°_f$) of the metabolites from the elements (e.g. $H_2$, $O_2$, graphite). Gibbs Free Energy ($\Delta G°$) and enthalpy ($\Delta H°$) under standard conditions and concentrations can be determined from these tabular values for each reaction of interest (Chang, 1981). Standard conditions are 1 M concentration of each soluble reactant and product, $1.01325 \times 10^5$ Pa (1 atm) of all gases, and 298.15 K.

$\Delta G° = \Delta G°_f$ of products $- \Delta G°_f$ of reactants and $\Delta H° = \Delta H°_f$ of products $- \Delta H°_f$ of reactants

TABLE 1

Thermodynamic data of selected compounds.

| Substance | $\Delta H°_f$ | $\Delta G°_f$ |
|---|---|---|
| Methane (g) | −74 | −50 |
| Ethane (g) | −84 | −32 |
| Propane (g) | −105 | −24 |
| Butane (g) | −125 | −17 |
| 2-Methylbutane (aq) | −134 | −3 |
| Pentane (aq) | −147 | 9 |
| Hexane (aq) | −167 | 18 |
| Heptane (aq) | −188 | 27 |
| Octane (aq) | −208 | 36 |
| Methanol (aq) | −201 | −176 |
| Ethanol (aq) | −235 | −182 |
| 1-Propanol (aq) | −255 | −173 |
| 2-Propanol (aq) | −273 | −186 |
| 1-Butanol (aq) | −275 | −163 |
| 2-Methyl-1-propanol (aq) | −284 | −167 |
| 2-Butanol (aq) | −293 | −179 |
| 1-Pentanol (aq) | −294 | −153 |
| Acetoaldehyde (aq) | −166 | −140 |
| Propanal (aq) | −185 | −130 |
| Butanal (aq) | −205 | −120 |
| Acetic acid (aq) | −432 | −394 |
| Propionic acid (aq) | −453 | −385 |
| Butyric acid (aq) | −475 | −378 |
| Valeric acid (aq) | −491 | −365 |
| Hexanoic acid (aq) | −511 | −386 |
| Glucose (aq) | −1264 | −917 |
| $CO_2$ (g) | −413 | −386 |
| $H_2$ (g) | 0 | 0 |
| Water (l) | −286 | −237 |

Gibbs Free Energy in kJ per mole under standard conditions of several potential fermentation metabolites at 298.15 K and $1.01325 \times 10^5$ Pa (1 atmosphere). Standard conditions are 1 M concentration of each soluble reactant and product, $1.01325 \times 10^5$ Pa (1 atm) of all gases, and 298.15 K.

Adjustment to each $\Delta G°$ for temperature was made using a transformation of the van't Hoff equation (Chang, 1981) and enthalpy where $T_1$ and $T_2$ are the initial and final temperatures respectively, and $\Delta G°_{T1}$ and $\Delta G°_{T2}$ are the respective standard Gibbs Free Energy values:

$\Delta G°_{T2} = T_2/T_1 [\Delta G°_{T1} - \Delta H°(T_2-T_1)/T_2]$

So, for example the $\Delta G$ at 39° C. or 312 K was determined for many of the reactions of interest from the tabular data reported at 298.15 K because the fermentations were conducted at 312 K.

Once the $\Delta G°$ is determined, it can be used to calculate the actual $\Delta G$ for a specific set of conditions using the equation:

$\Delta G = \Delta G° + RT \ln \{[\text{products}]/[\text{reactants}]\}$ where the [products] and [reactants] is the product of the concentration of all products or reactants in the fermentation. Given this value, the Gibbs Free Energy available for a reaction can be calculated. If the $\Delta G$ is negative, there would be energy for organisms to produce ATP and grow while carrying out the process. If the $\Delta G$ is positive, the opposite reaction might enable the organisms to obtain energy.

When the $\Delta G$ for a reaction producing a certain product is negative, there is enough Gibbs Free Energy available to conserve some energy in a linked reaction such as ADP conversion to ATP. Thus, organisms that catalyze reactions with strongly negative $\Delta G$ can capture more Gibbs Free Energy and grow faster. The conditions are necessary to select for previously unknown microorganisms carrying out previously unknown pathways such as alkane production from biomass were determined. It is one thing to find an organism that makes a trace amount of an alkane, but it is more useful to define the conditions that make it possible for an organism to grow from the energy it obtains by making a certain product (e.g. an alkane) from certain reactants (e.g. $CO_2$, CO and $H_2$). Once these conditions are defined, it is possible to isolate organisms that rapidly make high concentrations of the desired products while conserving Gibbs Free Energy.

All of the separate equations for $\Delta G$ can be compared for a given set of conditions, and the conditions altered in a spreadsheet to determine the impact on the $\Delta G$ for each reaction. In this way, conditions can be determined in which a desired reaction will be favored ($\Delta G$ more negative) compared to other reactions.

In addition, the equilibrium concentrations of products can be determined assuming certain reactions might go to equilibrium and use available substrate. An example was provided for alkyl alcohols previously (U.S. Ser. No. 12/385,215). For an additional example, consider the reaction to convert a VFA to an alkane. Equilibrium concentrations of each VFA with possible alkanes can be calculated under certain manipulated gas pressures. With a certain ratio of $H_2$ to $CO_2$ and with pressurization, for example, conversion of VFA to alkane could be favored. Conditions can be established where alkanes would be favored over the VFA and these conditions used to create alkanes or to isolate microorganisms to create them. The use of the thermodynamic model requires the understanding that selection for conditions to accumulate a favored product are not necessarily the same as conditions to enrich for or select organisms that make that product. It may be advantageous to establish conditions in which the favored product is created before it is converted to something else by different organisms. As long as conditions favor production of the desired product in the first place, they may be suitable for enrichment or isolation.

Pathways to Produce Alkanes and Other Products.

Whereas alkanes are saturated hydrocarbons, their conversion from carbohydrate, carboxylic acids, or amino acids requires decarboxylation (removal of $CO_2$) or their conversion from sugars, carboxylic acids, amino acids, aldehydes, ketones, alkenes, or alkynes requires addition of hydrogen and usually co-production of $H_2O$. For example, carboxylic acids may be converted to alkanes by decarboxylation:

where R represents an alkane group. If R is $CH_3$, the alkane formed would be methane from acetate. Decarboxylation of longer chain acids yields longer alkanes wherein the alkane has one fewer carbon atoms than the carboxylic acid from which it is derived. Conditions of low $CO_2$ or high carboxylic acid concentration drive this reaction forward. Removal of the $CO_2$ and alkane by vacuum or perfusion with another gas such as $N_2$, especially in the presence of high concentrations of carboxylic acids, drives the reaction forward.

Alternatively, the alkane may be produced by hydrogenation of the carboxylic acid in several steps:

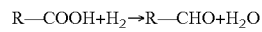

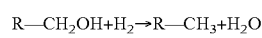

In the first step above, the carboxylic acid is converted to an aldehyde. For example, the two-carbon carboxylic acid, acetic acid can be converted to acetylyaldehyde. In the second step above, the aldehyde can be converted to an alcohol. For example, the acetylaldehyde can be converted to ethanol. In the third step above, the alcohol can be converted to an alkane. Thus, one aspect of the present invention is conversion of carboxylic acids to aldehydes, ketones, or alcohols as well as alkanes. The production of alkanes by hydrogenation is promoted thermodynamically by high concentrations of $H_2$.

Yet another pathway of importance to the invention is the elongation of carboxylic acids.

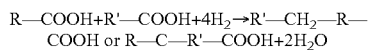

For example, if R and R' are both methyl groups then each starting carboxylic acid would be acetic acid and the resulting acid would be butyric acid:

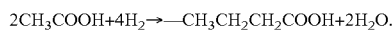

One means of elongation involves addition of the intermediate acetyl-CoA to a fatty acid. Elongated fatty acids can be converted to long-chain alkanes and used for bio-diesel or bio-gasoline. The inventor has isolated 1-hexanoic and 1-octanoic acids from fermentation mixtures for example, and thus production of medium-length fatty acids is known.

Thermodynamics of Alkane Production

For the equations listed above, the change in Gibbs Free Energy under standard conditions ($\Delta G°$) was determined in the established way of calculating the Gibbs Free Energy of Formation from the elements for each reactant and product and subtracting the Gibbs Free Energy of Formation of the products from the Gibbs Free Energy of Formation of the reactants.

In general, removing the product carbon dioxide from the fermentation shifts equilibrium toward decarboxylation resulting in an alkane. Addition of hydrogen to the fermentation shifts equilibrium toward hydrogenation and conversion of acids to aldehydes or ketones and ultimately to alkanes. Both low carbon dioxide and high hydrogen should promote the elongation of carboxylic acids to longer carboxylic acids, which can be converted to alkanes.

Table 2 shows the calculated $\Delta G$ values (not including ATP) for example reactions that comprise aspects of the current invention using book values for $\Delta G$ of formation of metabolites (Guthrie, 1992. Can. J. Chem. 70: 1042-1054 incorporated herein by reference). Only the $CO_2$ and $H_2$ concentrations were manipulated in this example, but of course many other metabolites can also be manipulated, and inhibitors of undesired reactions can also be used when thermodynamics is not enough by itself. Conditions typical for fermentation are shown in the second column ($CO_2$=1 atm; $H_2$=0.0001 atm). The negative $\Delta G$ for methanogenesis indicates that microbes would be able to capture about 1 ATP per mole of methane produced. Reactions for carboxylic acid synthesis have positive $\Delta G$ indicating that carboxylic acids would not be synthesized, and might be degraded. Carboxylic acids would also not be elongated or hydrogenated, but there is a slight possibility for decarboxylation to produce an alkane from the carboxylic acid. As the $H_2$ pressure is increased, methane production becomes more feasible, but so does the potential for carboxylic acid synthesis and elongation. Note that the $\Delta G$ for synthesis of longer VFA and carboxylic acid becomes more negative as the ratio of $H_2$ to $CO_2$ increases (FIG. 1). In addition, it becomes feasible to hydrogenate the carboxylic acids to produce alkanes (FIG. 2). If the $CO_2$ concentration is decreased, reactions that chemically reduce $CO_2$ become less favorable (e.g. synthesis of methane or acetate), and reactions that use the $H_2$ in a different way (e.g. reduction of acids to make longer acids) become more favored. In addition, decarboxylation is favored. Based on this example, one can clearly see the potential to establish conditions to favor organisms with certain functional traits over others, and by using multiple steps in the isolation, organisms with a specific set of traits can be isolated.

TABLE 2

Gibbs Free Energy change ($\Delta G$, kJ) for fermentation reactions under different partial pressures of $CO_2$ and $H_2$ at 39° C. More thermodynamically favorable reactions are identified by more negative $\Delta G$.

| | $CO_2$ = 1 atm | | | $CO_2$ = 0.0001 atm | | |
| --- | --- | --- | --- | --- | --- | --- |
| | $H_2$ (atm.) | | | | | |
| | 0.0001 | 0.01 | 1.0 | 0.0001 | 0.01 | 1.0 |
| $CO_2$ + 4$H_2$ → $CH_4$ + 2$H_2O$ | −48 | −96 | −144 | −24 | −72 | −120 |
| Carboxylic Acid Synthesis | | | | | | |
| 2$CO_2$ + 4$H_2$ → Acetate + 2$H_2O$ | 17 | −31 | −78 | 65 | 17 | −31 |
| 3$CO_2$ + 7$H_2$ → Propionate + 4$H_2O$ | 28 | −56 | −140 | 102 | 18 | −66 |
| 4$CO_2$ + 10$H_2$ → Butyrate + 6$H_2O$ | 55 | −64 | −183 | 154 | 35 | −85 |
| 5$CO_2$ + 13$H_2$ → Valerate + 8$H_2O$ | 95 | −60 | −215 | 219 | 64 | −92 |
| 6$CO_2$ + 16$H_2$ → Caproate + 10$H_2O$ | 123 | −68 | −260 | 270 | 79 | −112 |
| 8$CO_2$ + 22$H_2$ → Caprylate + 14$H_2O$ | 172 | −91 | −354 | 367 | 104 | −158 |
| Carboxylic Acid Elongation | | | | | | |
| Ac + $CO_2$ + 3$H_2$ → Prp + 2$H_2O$ | 10 | −26 | −61 | 37 | 1 | −35 |
| Valerate + $CO_2$ + 3$H_2$ → Caproate + 2$H_2O$ | 27 | −9 | −44 | 51 | 15 | −20 |
| 2Ac + 2$H_2$ → Butyrate + 2$H_2O$ | 24 | 0 | −24 | 24 | 0 | −24 |
| Butyrate + Ac + 2$H_2$ → Caproate + 2$H_2O$ | 51 | 27 | 3 | 51 | 27 | 3 |
| Caproate + Ac + 2$H_2$ → Caprylate + 2$H_2O$ | 32 | 8 | −16 | 32 | 8 | −16 |
| Caprylate + Ac + 2$H_2$ → Capric + 2$H_2O$ | 35 | 11 | −13 | 35 | 11 | −13 |
| Carboxylic Acid Decarboxylation | | | | | | |
| Acetate → $CH_4$ + $CO_2$ | −66 | −66 | −66 | −90 | −90 | −90 |
| Butyrate → Propane + $CO_2$ | −11 | −11 | −11 | −38 | −38 | −38 |
| Valerate → Butane + $CO_2$ | −28 | −28 | −28 | −56 | −56 | −56 |

TABLE 2-continued

Gibbs Free Energy change (ΔG, kJ) for fermentation reactions under different partial pressures of $CO_2$ and $H_2$ at 39° C. More thermodynamically favorable reactions are identified by more negative ΔG.

| | $CO_2$ = 1 atm | | | $CO_2$ = 0.0001 atm | | |
|---|---|---|---|---|---|---|
| | $H_2$ (atm.) | | | | | |
| | 0.0001 | 0.01 | 1.0 | 0.0001 | 0.01 | 1.0 |
| Caproate → Pentane + $CO_2$ | −33 | −33 | −33 | −61 | −61 | −61 |
| Caprylate → Heptane + $CO_2$ | −24 | −24 | −24 | −52 | −52 | −52 |
| Carboxylic Acid Hydrogenation | | | | | | |
| Butyrate + 3$H_2$ → Butane + $H_2O$ | 9 | −27 | −62 | 9 | −27 | −62 |
| Caprylate + 3$H_2$ → Octane + $H_2O$ | −2 | −38 | −74 | −2 | −38 | −74 |

Assumed concentrations of reactants and products include: carboxylic acids, 50 mM, alkanes 0.01 atm. soluble gas, $H_2O$ = 50M, pH = 6.5, temperature = 39° C.

Typical fermentation conditions (e.g. $H_2$ to $CO_2$ ratio 0.0001) for natural systems (e.g. cow's rumen or anaerobic digester) are similar to the far left side of FIGS. 1 and 2. Under such conditions, the ΔG for synthesis of octanoic acid, heptane, and octane are strongly positive. The ΔG for acetate synthesis from gases is slightly positive. It is not surprising that alkanes longer than one carbon are not produced under such conditions and carboxylic acids are degraded to methane and $CO_2$. Microbes from the cow's rumen degrade fatty acids to methane, which is a thermodynamically favorable pathway under natural conditions, were observed. Alkanes are similar in composition to carboxylic acids except for the absence of the carboxyl group. However, under unnatural conditions in which partial pressure of $H_2$ exceeds about 0.05 atm, the ΔG for synthesis of long-chain carboxylic acids becomes negative, and the feasibility of decarboxylation or hydrogenation of carboxylic acids increases. The exact point where the transition occurs can be greater than 0.05 atm depending on concentrations of other metabolites (products and reactants) and other conditions (e.g. temperature, pH). Whereas the curves for synthesis of methane or acetate are more flat than for the longer chain carboxylic acids or alkanes, near the ratio of $H_2$ to $CO_2$ for maximal synthesis of alkanes (between about 2 to 3), the equilibrium ratio of longer alkanes to methane or acetate increases. Thus, it is clear that in the range of this ratio, it is feasible and more favorable to produce longer chain carboxylic acids, longer chain alkanes, or to decarboxylate acids to make alkanes. When incubating with only $H_2$ (no $CO_2$) in the head space, it continues to be favorable to decarboxylate the longer chain carboxylic acids to form alkanes, but the advantage of doing so compared to methane synthesis decreases. It has been observed that octanoic acid was degraded to methane, ethane, propane, butane, and pentane which were measured in the gas phase, when incubating octanoic acid with rumen fluid under 3 atm $H_2$ pressure. However, octanoic acid would be more likely to be converted to octane or heptane when incubating with a ratio of $H_2$:$CO_2$ of 2:1 to 3:1. Including methane inhibitors or methane itself, or selecting against methanogens can further shift the fermentation toward the desired longer alkanes.

If the ratio of $H_2$ to $CO_2$ is either too great or too little, the longer chain alkanes or longer chain acids are degraded in an undefined mixed culture fermentation or pure culture. Therefore, under natural conditions (for most places on earth at the present time) production of alkanes or longer chain acids would not occur. However, under unnatural and manipulated conditions of $H_2$ to $CO_2$ ratio and pressure, alkanes can be produced from synthesis gases.

In addition to manipulating the ratio of $H_2$ to $CO_2$ to increase length of carboxylic acids or alkanes, or to produce more alkanes with greater than one carbon, the total pressure of the fermentation vessel can also be manipulated. FIG. 3 shows the effect of pressure on ΔG for synthesis of example acids and alkanes. As the pressure increases, synthesis of methane, acetate, longer-chain alkanes, and longer chain carboxylic acids all become more feasible. In this case the $C_8$ carboxylic acid (octanoate) and $C_7$ and $C_8$ alkanes represent longer chain alkanes. The difference among each metabolite represents the ΔG for conversion from one to the other. Although the ΔG decreases for each product of synthesis gases as the pressure increases, the ΔG decreases more rapidly for the longer chain acids and alkanes, and the difference between the longer chain acids and alkanes and methane or acetate increases. Thus, increasing pressure of all gases at a constant ratio of $H_2$ to $CO_2$ favors longer chain alkanes and acids over shorter chain acids. In this example, the widening difference between octanoic acid and octane represents the fact that hydrogenation is favored thermodynamically as pressure increases. The widening difference between acetate and octanoate represents the decrease in ΔG for elongation of carboxylic acids as pressure increases. More negative ΔG again represents the increased favorability of the elongation reactions. In contrast, the consistent difference between octanoic acid and octane shows that decarboxylation is unaffected by total pressure. However, as the total pressure decreases below 1 atm or preferably below 0.5 atm, the ΔG for competing reactions becomes more positive and decarboxylation is favored. Thus, at low total pressure of gases, methane is formed by decarboxylation of acetate, but not from $CO_2$ and $H_2$. Longer carboxylic acids are also decarboxylated to form longer alkanes as observed in several experiments. The elongation of acids and hydrogenation are especially favored over other uses of $H_2$ as the total pressure increases.

These effects of ratio of $H_2$ to $CO_2$ and total pressure are used to favor production of longer chain alkanes and longer chain acids over methane and acetate. Although the relationship that is shown only represents a few specific alkanes or acids, the same relationships hold for any length of alkane or acid. Thus, to increase the length of acid or alkane, higher pressure can be used with the optimal ratio of $H_2$ to $CO_2$. Low pH also decreases the favorability of acid production and favors alkanes, or to a lesser extent longer chain acids. Thus, an embodiment of this invention is to increase the pressure, maintain an optimal ratio of $H_2$ to $CO_2$, and use an appropriate pH to make alkanes when desired, or to degrade alkanes if that is desired, or to isolate or improve the microorganisms that can carry out either or both reactions. The same approach can be used to make or degrade other hydrocarbons (e.g. alkenes), or other organic compounds. However, in the case of alkenes or alkynes, low $H_2$ pressure such as from vacuum pressure or perfusion of other gas decreases $\Delta G$ and makes the production of alkenes or alkynes from alkanes more favorable.

Alkanes longer than methane are not usually formed in an anaerobic digester because hydrogenation and decarboxlation of longer-chain acids is not thermodynamically favorable without input of energy for the concentrations and partial pressures of the typical fermentation. The most thermodynamically favorable reactions involve chemical reduction of $CO_2$. Therefore, under typical conditions for biomass degradation and fermentation, most available hydrogen will be used with carbon dioxide to produce methane. In a typical fermentation, carbohydrates are degraded to carboxylic acids, $CO_2$ and $H_2$. For example, the repeating unit of cellulose, glucose, may be degraded to 2 acetic acid, 2 $CO_2$ and $4H_2$. The degradation of acetic acid subsequently results in 2 $CO_2$ and one $4H_2$ which can be used to synthesize an additional $CH_4$. This reaction uses the available $H_2$ making it thermodynamically infeasible to produce other alkanes. Typically the fermentation stabilizes with excess $CO_2$ and low concentrations of $H_2$. These conditions result in about equal concentrations of $CH_4$ and $CO_2$. If the $H_2$ pressure builds up, the continued production of $CH_4$ may eventually inhibit further $CH_4$ production, and other alkanes may become thermodynamically favored.

Under artificial conditions, the production of longer alkanes can be made thermodynamically favorable, and with the change in conditions, the microorganisms that carry out those reactions may be enriched and selected for. One set of artificial conditions includes application of vacuum pressure or purging with gases to remove $CO_2$ to increase decarboxylation and spare hydrogen for hydrogenation. Perfusion of an inert gas like $N_2$ removes $CO_2$ in much the same way as application of vacuum. Alternatively, perfusion of $H_2$ gas both removes $CO_2$ and directly increases $H_2$. The artificial conditions can be created using a vacuum pump with or without membrane filters to selectively remove gases or recycle gases. The thermodynamically favorable conditions for alkane production can be created with pressures that are less, equal or greater than atmospheric pressures; the relative partial pressures compared with the acids and undesired products is the important factor.

Based on the stoichiometry and second law of thermodynamics, the optimal ratio of $H_2:CO_2$ for methane production is 4. Therefore, incubating at this ratio maximizes methane production compared to other potential end products. The thermodynamics may also favor the breakdown of longer chain hydrocarbons to methane or shorter alkanes, as conversion of longer-chain alkanes to shorter-alkanes also uses $H_2$. Thus, it may be advantageous to isolate microorganisms to carry out the desired pathways leading to the desired alkanes, but excluding undesired pathways. In general, manipulating the fermentation to produce alkanes involves increasing $H_2$ and decreasing $CO_2$, and inhibiting, or selecting against alkane cracking if it is not desired.

One aspect of this invention is the process of incubating biomass including organic acids, aldehydes, or ketones under conditions that make it thermodynamically favorable to produce alkanes so that alkanes can be produced in higher concentration than normally observed. The biomass may also comprise cellulose, hemicellulose, pectin, starch, sugars, protein or other more complex biomass that can be converted to acids by anaerobic digestion and further converted to alkanes. The acids can also be derived from synthesis gases such as $CO_2$, CO and $H_2$, which can be synthesized to organic acids like acetic acid, propionic acid or butyric acids or longer acids under high partial pressures of the gases, and which can be converted to alkanes directly from synthesis gases or indirectly from the acids. Any feedstock that can be converted to carboxylic acids can be converted to an alkane. Another aspect of the invention is to apply artificial conditions that favor alkane production based on thermodynamics to enrich for and isolate microorganisms that can produce alkanes of greater than one carbon in length. The microbial cultures that convert biomass to alkanes and the process to enrich for and isolate the microorganisms are both aspects of the invention.

In the experiments, alkanes were produced from volatile fatty acids when incubating in $N_2$, $H_2$, vacuum or even $CO_2$. The incubation in vacuum resulted in the highest concentration of alkanes (ethane, propane, butane, pentane, higher length were not measured). However, the lower amount of gas in the headspace for the vacuum treatment means the actual gas production was not higher. The hydrogen treatment resulted in the highest alkane production. The results from this application of the process of Directed Equilibrium were surprising because the fact that such organisms exist in the rumen or anywhere was unknown. However, once it was determined that such organisms exist in anaerobic microbial cultures, and the conditions to favor these microorganisms were defined, it was routine to isolate such organisms from these cultures and to use them in cultures to convert biomass or synthesis gases to alkanes.

Specific Enrichment and Isolation Treatments for Hydrocarbon Production

One embodiment of the current application is isolation and development of microorganisms based on their functional traits. This is a process that can be carried out quickly and with efficient use of resources. For example, a library of organisms was assembled capable of carrying out the reactions of interest under a variety of conditions. Subsequently, organisms in this library can be improved primarily by making them produce the desired products faster and to a higher concentration, and to convert a high percentage of the gases to the desired products.

The following procedures result in the isolation and development of microorganisms that can be used for making hydrocarbons or other products from biomass or from $CO_2$, CO, and $H_2$. These microorganisms can have the following functional attributes:

Convert $CO_2$, CO, and $H_2$ to carboxylic acids of medium length ($C_5$ to $C_{10}$) or longer.

Convert acetate and butyrate to longer chain carboxylic acids.

Convert biomass to medium length carboxylic acids ($C_5$ to $C_{10}$) or longer.

Convert carboxylic acids to alkanes by hydrogenation or decarboxylation.

Convert $CO_2$ and $H_2$ directly to alkanes.

Convert biomass directly to alkanes of greater than one carbon in length.

The organisms are selected and developed to be robust (easily maintained and grow quickly), produce the desired products at a high rate to a high concentration of product, and to convert a high percentage of the substrate (e.g. gases) to the desired products. The alkane products are analyzed for octane number, energy density and heat of vaporization, and the process using the organisms analyzed for energy conversion efficiency.

In general, isolation methods follow established protocols that have been used for alcohols and acids. These protocols employ mathematical models incorporating thermodynamics and kinetics to create conditions in which only the desired organisms can grow. Several iterations of enrichment, isolation, screening and evaluation are conducted to develop a library of organisms with the desired traits. Key organisms may be improved through non-specific mutagenesis with several more iterations using similar procedures.

For each of the types of organisms that are desired, several different enrichment and isolation strategies can be undertaken at the same time (Table 3). Forward strategies enrich for organisms under conditions that produce the desired products and then select for organisms under similar conditions, and reverse enrichment strategies enrich for organisms that degrade the desired product and then select organisms that produce the desired product under the opposite conditions. Both forward and reverse enrichment strategies are used herein. The reverse enrichment strategies may use air, $N_2$ or $CO_2$ as the gas composition to potentially select for aerobes, and facultative and strict anaerobes that may or may not require $CO_2$. Reverse strategies use high concentrations of the desired product to select for tolerant organisms. Several concentrations are used. Forward strategies use $H_2$ or ratios of $H_2$ and $CO_2$ as the gas composition that favor synthesis according to the thermodynamic model. Different pH levels are also be used for both enrichment and isolation, and isolation is performed with different media formulas including different levels of complex nutrients (e.g. yeast extract, amino acids) in an attempt to isolate microbes with minimal nutrient requirements if possible. Enrichment is repeated for multiple steps before isolation.

The use of separate steps makes it possible to continually favor the desired reactions and to optimize the efficiency of the process. In particular, maintaining a low concentration of short-chain intermediates during the conversion of carboxylic acids to alkanes inhibits the production of short-chain alkanes. However, other means are available to manage production of short-chain alkanes if needed including recirculating short-chain alkanes or using them in separate process. Thus, it may be completely acceptable to produce a mixture of lengths of alkanes or to control the length by the thermodynamics and composition of reactants and products.

Conditions for Carboxylic Acid Synthesis (Step 1)

Reduction of $CO_2$ to produce acetate or longer chain carboxylic acids requires control of the fermentation conditions to favor the forward reaction. Otherwise, the same microorganisms degrade acetic acid to $CO_2$ and $H_2$. Based on the calculation of the G values, conditions to thermodynamically favor acetic acid production include pressurization of the reaction vessel and maintenance of the ratio of $H_2$ to $CO_2$ of 2:1. In the present case, however, longer-chain acids are desired and the optimal ratio of $H_2$ to $CO_2$ for longer-chain carboxylic acids approaches 3:1. As the ratio of $H_2$ to $CO_2$ increases beyond 3:1, the G for carboxylic acid synthesis decreases so the organisms orchestrating the reaction are not able to capture as much free energy from carrying out the process. Nonetheless, as the ratio of $H_2$ to $CO_2$ continues to increase, longer chain carboxylic acids are further favored over short-chain carboxylic acid as long as it is still feasible to

TABLE 3

Conditions for enrichments to isolate organisms with desired functional traits.

| Target | Enrichment Additions | Enrichment Gas Mix | Isolation Gas Mix |
|---|---|---|---|
| $CO_2$ and $H_2$ → $C_5$-$C_{12}$ fatty acids | Individually include $C_5$-$C_{12}$ fatty acids | $N_2$, air, or $CO_2$ (favors degradation) | 3:1 $H_2$:$CO_2$ or (favors synthesis) |
| | Media only (alternate with above enrichment) | 3:1 $H_2$:$CO_2$ | 3:1 $H_2$:$CO_2$ or (favors synthesis) |
| | $C_2$-$C_4$ fatty acids (disfavors short chain) | 3:1 $H_2$:$CO_2$ | 3:1 $H_2$:$CO_2$ or (favors synthesis) |
| $C_2$-$C_4$ fatty acids → C5-C12 fatty acids | $C_2$-$C_4$ fatty acids (favors elongation) | 3:1 $H_2$:$CO_2$ | $H_2$ or 3:1$H_2$:$CO_2$ with fatty acids |
| $C_5$-$C_{12}$ fatty acids → C5-C12 alkanes | Individually include $C_5$-$C_{12}$ alkanes | $N_2$, air, or $CO_2$ (favors degradation) | $H_2$ or 3:1$H_2$:$CO_2$ with fatty acids |
| | Individually include $C_5$-$C_{12}$ fatty acids | 3:1 $H_2$:$CO_2$ | $H_2$ or 3:1$H_2$:$CO_2$ with fatty acids |
| $CO_2$ and $H_2$ → $C_5$-$C_{12}$alkanes | Individually include $C_5$-$C_{12}$ alkanes | $N_2$, air, or $CO_2$ (favors degradation) | 3:1 $H_2$:$CO_2$ (favors synthesis) |

At this time, a process that will use two fermentation steps to obtain alkanes of the desired length and level of branching is contemplated. Additionally, a single-step process is also contemplated. First, a set of organisms produces carboxylic acids ranging in length from C2 to C12. The short-chain carboxylic acids (C2 to C5) remain soluble in the aqueous phase until they are elongated. The medium-chain carboxylic acids (C5 to C12) are immiscible in aqueous solutions and separate to the top of the medium with their hydrophilic carboxyl groups in the aqueous phase, or they are incorporated into cell membranes. The medium-length carboxylic acids are removed from the top of the reactor and incubated under specific conditions with a separate set of organisms that convert them to alkanes. The hydrophobic alkanes separate to the top of the medium where they can be removed and separated from the carboxylic acids by distillation. Alkanes evaporate at lower temperatures than equivalent-length carboxylic acids.

produce them. Eventually, at a very high ratio of $H_2$ to $CO_2$ the ΔG becomes positive just as it is at very low ratio of $H_2$ to $CO_2$ and carboxylic acids may be degraded. Thus, it is necessary to maintain just the right ratio of $H_2$ to $CO_2$ with total pressure and other conditions to make it thermodynamically feasible and thermodynamically favorable to produce the longer chain acids. The means to calculate the necessary conditions (G) were described in U.S. Ser. No. 61/266,610, which is incorporated by reference.

Organisms that primarily produce acetic acid or ethanol, and other organisms that primarily produce longer chain VFA such as propionic acid, butyric acid, or valeric acid have been isolated. Condensation reactions in anaerobic digestion readily convert two acetate molecules to butyrate or acetate and propionate to valerate. The butyrate and valerate can be further elongated by condensation to create medium and long chain carboxylic acids that can be used for production of fuels such as gasoline. In addition, longer chain carboxylic acids are also produced by addition of the acetyl group of acetyl-CoA to carboxylic acids. High $H_2$ pressure (e.g. 2 to 3 atm.) thermodynamically favors the elongation reactions especially when low $CO_2$ pressure disfavors synthesis of acetate. Thus, the ratio of $H_2$ to $CO_2$ may be increased during the fermentation to increase the length of carboxylic acids produced.

Conditions for Conversion of Carboxylic Acids to Alkanes (Step 2)

The decarboxylation of acetate to methane and $CO_2$ is well known. However, it was observed that the decarboxylation and hydrogenation of longer chain volatile fatty acids to produce longer chain alkanes. These reactions are thermodynamically favored under low $CO_2$ and high $H_2$ pressures. For example, when butyrate was incubated with an undefined culture of rumen microbes under $H_2$ pressure, major products that resulted were propane, butane and iso-butane. Thus, microorganisms decarboxylated butyrate to produce propane and hydrogenated butyrate to produce butane. Thus, microorganisms in mixed rumen fluid can be used to decarboxylate or hydrogenate the medium-chain length carboxylic acids of the previous step to alkanes using high ratios of $H_2$ to $CO_2$ to favor the elongation and isomerization. Low $CO_2$ pressure can be obtained by purging with other gases (e.g. $N_2$), as well as $H_2$, or by applying vacuum pressure. Wherein one competing reaction is degradation of the carboxylic acids or alkanes (e.g. to produce methane), a ratio of $H_2$ to $CO_2$ will again be maintained to limit degradation and optimize final alkane length. For example a ratio of $H_2$ to $CO_2$ of 2:1 or 3:1 or greater will favor further elongation of carboxylic acids and prevent degradation to short-chain products while still making it thermodynamically feasible for alkane production. Higher total gas pressure (e.g. 2 atm or preferably 3 atm or even more preferably 4 atm) favors hydrogenation of carboxylic acids, and elongation of carboxylic acids and alkanes.

EXAMPLES

Example Procedures. There are many variations on the methods to enrich for microorganisms for production of alkanes compared to producing other products. Media usually minimize extraneous sources of energy (e.g. glucose), to select for organisms that can grow from the energy they capture from the process being enriched for. For example, when an organism to decarboxylate or hydrogenate carboxylic acid is desired, only the carboxylic acid is used as an energy substrate. Various amounts and types of carboxylic acids can be used. These conditions select for organisms that can utilize the carboxylic acids under conditions favoring decarboxylation (e.g. low $CO_2$), and hydrogenation (high $H_2$) at ratios that do not favor the complete degradation of the carboxylic acid. For example, $CO_2$ to $H_2$ molar ratio of 2 minimizes degradation of VFA. Since different length acids are used, organisms are selected specializing in accessing a certain length acid.

Alternatively, a reverse enrichment strategy can be used in which the desired alkanes are initially included in the media in place of the carboxylic acid, and gas composition and concentrations of solutes are controlled to make it thermodynamically favorable to degrade the alkane. The gas composition includes either a very high ratio of $H_2$ to $CO_2$, a very low ratio of $H_2$ to $CO_2$, or $N_2$ or air. With air, aerobic or facultative aerobic organisms would be favored. Under these conditions, organisms isolated have the enzymes to make the alkanes. The same can be done for specific carboxylic acids, which could subsequently be converted to alkanes. Enrichment and isolation can use media buffered to pH 7, pH 5, or pH 4. The lower pH disfavors carboxylic acid producers and methane producers but maximal growth of organisms is obtained near neutral pH (e.g. between 5 to 7).

Enrichment also includes sequential steps. In one step, a desired product, such as an alkane or carboxylic acid, may be used under conditions to degrade or convert it. And in another step, organisms that use a certain type of biomass, such as plant fiber or synthesis gases, can be supplied without other substrate to enrich for organisms that use the substrate. Over several iterations, organisms are selected that can utilize a certain substrate to produce a desired product.

Isolation. Roll tubes and agar plates use the same medium as for enrichment but also sometimes contain 20% strained and autoclaved rumen fluid for micronutrients. Tubes are incubated for 1 day to up to several weeks at a temperature usually between 25 to 60° C., and preferably about 40° C., and independent colonies selected from these.

Maintenance. Colonies are selected from among the colonies in roll tubes and agar plates, and are transferred to broth for short-term maintenance. The broth is of the same composition as media for other purposes, but does not contain agar. All cultures are maintained in large tubes leaving a high proportion of headspace, the ratio of $CO_2$ to $H_2$ or CO to $H_2$ that favors synthesis of the products, and gas pressures of 2 atm to 4 atm. Broth cultures are transferred to new media (5% final concentration, vol/vol) one to two times per week. After two to three cultures, 0.1 ml culture is transferred to a slant culture in a 25-ml tube with 10 ml media on a slant to increase surface area). The inocula is added on top of the agar, which is maintained under $CO_2$ and $H_2$ or CO and $H_2$ in the thermodynamically favored ratio. These are initially incubated at 39° C. until colonies form (16 h), and then are stored at 25° C. or 4° C. for up to a month. Cloudy broth cultures are also stored by adding 15% glycerol (final volume) and freezing in liquid nitrogen; once frozen, these colonies are stored at −80° C. Frozen cultures can also be freeze dried. Cultures are also maintained using carbohydrates as the energy source, such as glucose.

Screening. Screening of microorganisms addresses whether they can synthesize a certain hydrocarbon or acid from $CO_2$, CO, and $H_2$, or whether they can convert one or more acids to alkanes, and the extent to which they are tolerant to the product and other co-products. The isolates derived as described are screened by transferring 0.5 ml broth to 9.5 ml media (as described, no agar). Tubes are perfused with mixtures of $CO_2$, CO and $H_2$ to favor synthesis (e.g. 3:1 ratio of $H_2$:$CO_2$) of the desired product preferably under at least 2 atm total gas pressure. Preferably 4 atm total gas pressures are used. However, successful isolations are also performed with only 1 atm total gas pressure with the ideal ratio of gases. The pH of the media is adjusted to 7, 5, or 4 and 3% or 6% mixed VFA or longer chain carboxylic acids added for different runs. The cell growth is determined by turbidity (optical density), and alkanes and acids are measured by gas chromatograph at time=0, and other time points (e.g. 3 d and 5 d). Unknown peaks are also identified by gas chromatography and mass spectrometry. All colonies are typically screened after first isolating them by adding the colony directly to a test tube with media, incubating with $H_2$ and $CO_2$ with or without VFA or longer carboxylic acid and determining which strains produce the highest concentrations of desired products or show other desired traits. The strains that appeared to be most ideal are sub-cultured and incubated again in fresh media in replicate to verify results and test for effect of different conditions (e.g. pH, gas pressure) of the fermentation.

Mutagenesis. The process of Directed Equilibrium can also be used to direct the evolution of microorganisms as described previously (e.g. U.S. Ser. No. 12/385,215). Once the conditions are defined that enable an organism to obtain energy from producing a desired product, and the conditions are defined in which it cannot obtain energy, based on the second law of thermodynamics and the defined calculations, the conditions can be established so that only microbes that produce the desired product obtain energy. The microorganisms that produce other products waste their energy and cannot compete with the desired organisms. Therefore, mutants that no longer produce the undesired products are favored and eventually these organisms predominate. After several enrichment phases, the desired mutants are selected under conditions favoring the desired product. Thus, it is possible to breed organisms that produce a predominant product.

These same conditions to enrich or isolate microorganisms that produce high concentrations of alkanes or acids from $CO_2$, CO and $H_2$ or that convert acids to alkanes can be used to improve isolated strains. Some improvements occur in the enrichment or isolation process although the improvements may not be observed. Pure cultures of microorganisms are incubated with the ratio and pressure of gases that thermodynamically favors synthesis of the desired alkane or acid, under pressures (e.g. 2 to 4 atm or higher), and in the presence of the products to which tolerance is desired. Under these conditions, organisms that produce the most of the desired product thrive, while those that produce more of the undesired product waste energy and become diluted. Over many generations, which can occur in a matter of days, organisms evolve under these conditions that can synthesize greater quantities of the desired product relative to other products, at faster rates, and that are more tolerant of the product and potential co-products. Mutation rate can be increased by brief exposure to UV light or other mutagen combined with thermodynamic controls. Using these conditions and several sub-cultures for enrichment of pure cultures, organisms can be developed that make only the desired products, at high rates, with high tolerance to those products. This process of directing evolution (or non-specific mutagenesis) selects for organisms on the basis of the products they make, and selects for organisms that can tolerate very high concentrations of products.

Previous attempts at non-specific mutagenesis did not select for organisms that produced specific products, so one could not increase the amount of those products produced as a portion of total products. As a result, many different products were made. In addition, previous methods at adaptation to higher levels of products (e.g. alkanes) by growing the isolates with the products selected against further production of those products (because they became thermodynamically limited). By maintaining highly thermodynamically favorable conditions for the production of desired products (e.g. alkanes) organisms can be adapted that produce the desired products even at high concentrations. Using this process, organisms that produce a desired alkane or desired carboxylic acid nearly exclusively, and at very high concentration, and a fast rate, are isolated. By maintaining conditions that strongly favor a certain pathway, the $\Delta G$ for that pathway becomes more negative, representing greater energy that can be captured by carrying out the reaction. Therefore, organisms that can link ATP production to the reaction grow faster and are enriched and later selected using the enrichment and selection processes described on cultures derived from organisms that have already been selected and may have mutated while growing. Organisms can thus be adapted to produce virtually nothing but the desired alkane at a fast rate.

After a library of desired organisms is assembled and evaluated, the leading organisms are subjected to a series of further enrichments and isolations, but this time starting with isolated pure cultures. Cultures are subjected to mutagenesis and enrichment using similar restrictive conditions as previously, but specifically designed to select for desired traits (e.g. rapid growth rate, tolerance to alkanes). Particular emphasis is placed on overcoming the complex issues like growth rate or membrane structure knowing that it is easier to knock out an undesired pathway using specific genetic engineering. Isolated organisms are maintained in broth for short-term use, on agar in sealed tubes for longer-term storage, and by freezing at −80° C.

Analysis Methods

It is necessary to measure short-chain and medium-chain carboxylic acids, and liquid and gaseous alkanes and other products after each isolation. One way to decrease the time and equipment needed is to use rapid screening tools so that each sample does not have to be completely analyzed. For example, separation procedures to rapidly evaluate production of medium-chain carboxylic acids or alkanes are used. These products are immiscible in aqueous medium. It was determined that less than half a percent of either medium-chain carboxylic acid or medium-chain alkane is visible as the top layer in a fermentation after centrifugation at 1500 g for 30 minutes. It is not possible to tell the difference between carboxylic acids and alkanes using this approach, but alkanes can be evaporated readily en masse and their disappearance from samples can be determined gravimetrically. A paired sample can be analyzed for the actual content of alkanes that disappeared. The total short-chain carboxylic acids can be grossly estimated by titration to a specific pH.

The volatile fatty acids ($C_2$ to $C_5$) are soluble and miscible in aqueous solutions, caproic ($C_6$) and heptanoic ($C_7$) acids are partially soluble and partially miscible, and longer-chain carboxylic acids ($>C_8$) are insoluble and immiscible in aqueous solutions. Thus, methods of separation and analysis vary for each group. Carboxylic acids are soluble in alkane solutions. The carboxylic acids and alkanes are separated from the aqueous phase by centrifuging at 1500 g for 30 minutes. The top layer including free carboxylic acids and alkanes is sampled when analyzing for both the carboxylic acids and alkanes. The extracted carboxylic acids are methylated and determined on the gas chromatograph (GC). The alkanes are analyzed using a carbowax column on a separate GC. The free volatile fatty acids are analyzed from the aqueous phase directly using a packed column without forming derivatives. For some samples, the microbial cells are isolated by differential centrifugation. The bacterial pellet is then be extracted to release triglycerides and free carboxylic acids are extracted from the pellet; triglycerides are hydrolyzed and the carboxylic acids are analyzed by GC. The microbial growth is measured by optical density.

The separated fuels are also to be analyzed for research octane number, energy density, and heat of vaporization. These data are used with the data on the raw efficiency (kg fuel produced per kg of $H_2$ and $CO_2$ used) from the fermentation experiments that produce the fuel. The fuel energy output per unit energy input is calculated as: energy density of the fuel (MJ/kg) times the raw efficiency (kg fuel/kg gas) times the energy cost of gas production (kg gas/MJ input). The financial cost is also be determined by substituting the inverse of the cost of gas production (kg gas/$) for the last factor. The evaluation uses purified gases, but the results are calculated for a number of different potential sources of gases that would be available including gases from electrolysis, biomass pyrolysis, and gasification.

One of the advantages of using microorganisms to catalyze the reactions is the possibility of using somewhat less pure sources of gases that will be less expensive to produce than purified gases. For example, most anaerobic microorganisms tolerate relatively high concentrations of sulfide. Trace amounts of other gas in addition to pure gas (excursions to the pure gas) can be used to determine the extent to which less pure gas can be used, and the leading microorganisms using such sources can be tested. If impurities affect the efficiency of some organisms, impurities can be added and trace amounts of impurities of different composition in the gas during the enrichment, isolation and development phase can be used to specifically develop organisms that can thrive on impure gases. Although it is important to use specific ratios of gases for microbial isolation and development in order to thermodynamically favor the desired pathways, once the organisms are isolated and developed, and some undesired pathways are removed, the ratio of gases is not as critical. The isolated organisms can be tested for the quality, quantity and efficiency of gasoline or value-added product production using different ratios of $CO_2$, CO and $H_2$ and available sources of the selected gases. Most organisms using $CO_2$ and $H_2$ can just as easily use CO and $H_2$.

Alternative Isolation Methods

In addition to isolations of microbes that can convert $CO_2$ and $H_2$ to carboxylic acids and alkanes, similar organisms can be used to produce carboxylic acids and alkanes from CO and $H_2$. Wherein $CO_2$ and CO are in equilibrium, these procedures would not be very different except a different ratio of $H_2$ to CO would be used to balance and maximize the production of acids. In addition, the carboxylic acids and VFA can be produced from biomass, or the alkanes may be produced directly from biomass instead of from gases.

Examples Using Mixed Cultures from the Rumen

Example Microbes that Produce Alkanes

An experiment demonstrated that under high $H_2$ and low $CO_2$ pressures, mixed rumen microbes (rumen fluid) converted volatile fatty acids to alkanes by both decarboxylation and hydrogenation. In this experiment, mixed rumen fluid was incubated at 39° C. under 2 atm $H_2$ pressure. Later the optimal ratio of $H_2$ to $CO_2$ was found to be 3 to 1. After five days incubation, alkanes were measured in the headspace of the fermentation at 39° C. using a gas chromatograph and Carbowax column. When 200 mM butyric acid was incubated under these conditions for five days, propane, butane and iso-butane were produced. Longer-chain alkanes were not measured in this experiment. A later experiment also produced hexane from heptanoic acid, but other alkanes were not measured conclusively. Other liquid alkanes may have been produced but were difficult to measure conclusively due to noise on the column. However, it is clear that any given alkane can be produced under the appropriate conditions using rumen microbes or other source of microbes. These results indicate that organisms in the rumen produce alkanes from organic acids. Rumen microbes have long been known to convert $CO_2$ and $H_2$ to acetate, and the acetate is known to be converted to propionate and butyrate and other long chain acids. However, the discoveries encompassing the present invention show that all of the steps for production of alkanes from $CO_2$ and $H_2$ exist in the rumen, and the conditions to favor their production have now been calculated and tested successfully.

Microbes that Convert VFA or Sugars to Alkanes

In one experiment, several different alkanes greater than one carbon in length were produced by fermentation using mixed rumen microorganisms. The methods for producing these alkanes are described below as they were carried out, but several changes were since discovered to increase the production of alkanes that could be produced. Treatments were arranged in a 2 by 4 factorial design with two substrates and three gas compositions. Duplicate screw-cap 15-ml test tubes contained one of the following as the substrates: ground (1 mm screen) 2% (wt/vol) timothy hay; or 0.5% of each: glucose, cellobiose, xylose; or 2% (vol/vol) of mixed VFA solution comprising an equimolar mixture of acetic acid, propionic acid, butyric acid, and valeric acid. The initial gas phase was also altered for different tubes including: vacuum pressure of 0.05 atm, or 1 atm $CO_2$, $H_2$, or $N_2$. All tubes were adjusted to pH 6.8 at the start of the incubation, and were incubated at 39° C. in a water bath for 10 days. Each tube contained 5 ml of media with substrate and 10 ml gas headspace. Media included 20% (vol/vol) rumen fluid taken directly from a fistualted Holstein cow, blended, and strained as in Goering and Van Soest, 1970 as cited. The headspace gas was sampled at 39° C. and analyzed on a GC using a Carbowax column (Agilent, Inc.).

The fermentation with timothy grass hay mainly produced one major alkane, methane. When incubating in $CO_2$, $H_2$, $N_2$ or vacuum the percentage methane of all gases was 23-24%, 40-42%, 20-21% and 17-20% respectively. The range represents the values of two duplicate samples. Trace amounts (0.001 to 0.002%) of ethane were also measured when vacuum or $CO_2$ comprised the gas phase, but no other alkanes were observed. This result does not indicate that timothy grass could not be converted to alkane, but rather that the gas produced from the fermentation changed the conditions so that it was not produced.

However, the gas phase for the mixture of sugars and VFA contained several different alkanes: methane, ethane, propane, butane, pentane, and hexane, and unidentified hydrocarbons in the same range. The concentration of methane in the gas phase for these samples was lower by an order of magnitude or more. For example, methane concentration (in parts per million) was 152-1679, 129-151, 123-140 and 263-330 for $CO_2$, $H_2$, $N_2$ and vacuum treatments respectively. The second most prevalent alkane was propane with mean of 8 ppm, and ranged from 5 to 14 ppm. There was no apparent affect of which gas phase was used. Mean butane concentration was 3 ppm and ranged from 2 to 5 ppm. Pentane and hexane were also observed at 2 to 3 ppm. Other peaks among these were also present but standards were not available to identify them. The peaks were likely to be branched chain alkanes. The conditions in this experiment were adequate to produce trace amounts of alkanes but generally did not favor much alkane production. The optimal gas phase would have been a combination of $H_2$ and $CO_2$ such as $H_2:CO_2$ ratio of about 3. The VFA were hypothesized to be the source of the alkane. Nonetheless, the experiment demonstrated that alkanes could be produced from carbohydrates or carboxylic acids using microbes taken directly from the rumen of a cow.

Conditions for Conversion of Carboxylic Acids to Alkanes

The decarboxylation of acetate to methane and $CO_2$ is well known. However, the decarboxylation and hydrogenation of longer chain volatile fatty acids to produce longer chain alkanes was observed. These reactions are thermodynamically favored under low $CO_2$ and high $H_2$ pressures. For example, when butyrate was incubated with an undefined culture of mixed rumen microbes under $H_2$ pressure, major products that resulted were propane, butane and iso-butane. Thus, microorganisms decarboxylated butyrate to produce propane and hydrogenated butyrate to produce butane. Thus, microorganisms in mixed rumen fluid can be used to decarboxylate or hydrogenate the medium-chain length carboxylic acids of the previous step to alkanes using high ratios of $H_2$ to $CO_2$ to favor the elongation and isomerization. Low $CO_2$ pressure can be obtained by purging with other gases (e.g. $N_2$), as well as $H_2$, or by applying vacuum pressure. Wherein one competing reaction is degradation of the carboxylic acids or alkanes (e.g. to produce methane), a ratio of $H_2$ to $CO_2$ will again be maintained to limit degradation and optimize final alkane length. For example a ratio of $H_2$ to $CO_2$ of 2:1 or 3:1 or greater will favor further elongation of carboxylic acids and prevent degradation to short-chain products while still making it thermodynamically feasible for alkane production. Higher total gas pressure (e.g. 2 atm or preferably 3 atm or even more preferably 4 atm) favors hydrogenation of carboxylic acids, and elongation of carboxylic acids and alkanes.

Example

Microbes and Conditions that Convert Carboxylic Acids to Alkanes and Alkenes

The previous experiment demonstrated that under certain conditions, alkanes were produced by mixed cultures of rumen bacteria. Based on those results, it was hypothesized that the alkanes were made from the VFA. For example, a carboxylic acid could be decarboxylated (e.g. $R\text{—}COOH \rightarrow RH + CO_2$) or hydrogenated ($R\text{—}COOH \rightarrow R\text{—}COH_2 \rightarrow R\text{—}CH_2OH \rightarrow R\text{—}CH_3$) to form an alkane. Alkenes could also be made from decarboxylation and dehydrogenation. (e.g. $R\text{—}CH_2\text{—}COOH \rightarrow R=CH_2 + H_2 + CO_2$). A subsequent experiment compared the production of alkanes from specific VFA with either vacuum (0.05 atm) or $CO_2$ in the 10 ml headspace. Aside from the substrates, the procedures were as described in the previous experiment. In this experiment, there was no mono- or di-saccharide added (i.e. no glucose, xylose or cellobiose), and only one VFA was included in each tube at a final concentration of 2% (wt/vol). In separate tubes 2% of acetate, propionate, butyrate, or valerate were added. Each tube was incubated for 6 days. Each treatment was replicated in triplicate.

All alkanes were produced in lower concentration in this experiment than in the previous one, and methane was the predominant alkane in each case. Methane concentration ranged from 351 to 453 ppm for the treatments with $CO_2$ and from 20 ppm to 79 ppm for the treatments under vacuum. There was a linear ($P<0.01$) decrease in methane as the length of the acid increased for the $CO_2$ treatments. For example, methane from acetate, propionate, butyrate, and valerate were 463, 400, 367, and 351 respectively. The effect was not significant for vacuum treatment. Trace concentrations of ethane, propane, butane, pentane and hexane were also observed mostly in the vacuum treatment. Acetate treatment with vacuum produced methane, ethane, propane, and butane. Propionate treatment produced only methane, ethane and a little propane. Butyrate treatment with vacuum produced methane, ethane, and propane. Valerate treatment with vacuum produced methane, ethane, propane, butane, pentane, and hexane. In addition to alkanes, alkenes were also produced for the vacuum treatment. The highest peak for the vacuum treatment with butyrate was for acetylene, a two-carbon alkyne, and the highest peak for the vacuum treatment with valerate was 1-butene (a.k.a. isobutylene, $CH_2=CHCH_2CH_3$). These compounds (all alkanes, alkenes and alkynes measured) also appeared at the same time points on the GC curve from a gasoline sample. Although the alkenes and alkynes were not initially expected, the low $CO_2$ and low $H_2$ pressures would thermodynamically favor conversion of carboxylic acids to alkenes and alkynes by decarboxylation and dehydrogenation. Butane and isobutylene are currently used together to produce iso-octane (a high-energy, high-octane fuel in gasoline).

The experiment was also conducted with similar conditions except 1 atm $H_2$ was used as the headspace gas. In this example, each VFA appeared to be decarboxylated and hydrogenated. For example, propionic acid yielded ethane and propane as well as methane. Butane yielded propane, butane and iso-butane (in order of concentration). Thus, the four-carbon butyric acid was converted to 3-carbon alkane (propane) by decarboxylation, or to 4-carbon alkanes (butane, isobutane) by hydrogenation. The hydrogenation step must also produce butene (an alkene which has a double bond) that is interconverted to isobutane. Many longer chain and branched chain hydrocarbons may also have been produced but were not measured.

Microbes that Produce Components of Gasoline from Fatty Acids

Longer-chain carboxylic acids were incubated under similar conditions to those described previously. For example, 1% heptanoic acid ($C_{7:0}$) was incubated with mixed rumen microbes (rumen fluid) and media as described previously for 4 days. In this case, the initial headspace gas was comprised of 2 atm of a ratio of $H_2$ to $CO_2$ of 2.5. At this ratio, the $\Delta G$ for alkane degradation to shorter alkane or acid degradation to shorter acid was positive so that degradation of the acid was not favored. After the incubation, the headspace gas was sampled after heating the sample to above about 150° C. to volatilize the longer-chain alkanes. Hexane was found in the measured sample only after incubation. Hexane is one of the components of gasoline and an industrial solvent. This example shows that microbes in rumen fluid can convert the longer-chain carboxylic acids to alkanes that are major products of gasoline as well as industrial solvents. In addition, the example shows the conditions in which the microbes carry out the desired reaction, and using those conditions isolation or development of the microbes is facilitated. Many other conditions could have been used as long as the composition and pressure of gases and other conditions enabled made it thermodynamically feasible for production of the alkane from heptanoic acid. Longer alkanes were probably also present but were difficult to measure in the headspace gas. Other VFA could have been used or longer-chain carboxylic acid could have been used to produce a different size alkane. In addition, low pressure would have favored decarboxylation over hydrogenation, and higher pressure would have favored hydrogenation.

Degradation of Hydrocarbons

Another treatment using rumen fluid included 1% heptanoic acid and other conditions as described above. Initial gas composition was 2 atm $H_2$ gas in place of the ratio of $H_2$ to $CO_2$ of 3. As seen in FIG. 3, at very high ratio of $H_2$ to $CO_2$, the degradation of alkanes to methane is favored. In this case, several short-chain alkanes were observed with the majority of alkane being methane and decreasing amounts of ethane, propane, butane, and pentane in that order. This experiment shows the production of alkanes longer than one carbon in length from carboxylic acids using rumen microbes, but in addition, it shows the degradation of such alkanes (e.g. cracking) to shorter alkanes under anaerobic conditions with high percentage $H_2$ at moderate pressure (e.g. 2 atm.) to produce shorter alkanes. Compared to chemically catalyzed methods of hydrocracking, for example for fossil fuel refinement, require much higher pressure and temperatures, and enzymatic (or microbial) methods are likely to be more specific to certain lengths of alkanes. Enzyme catalyzed hydrocracking using microorganisms may be useful for decreasing the length of hydrocarbons.

Examples of Pure Cultures that Produce Hydrocarbons

Example Isolation of Organisms to Convert $CO_2$ and $H_2$ to Alkanes

The Directed Equilibrium process was used to isolate microorganisms that convert $CO_2$ and $H_2$ directly to liquid alkanes in the range suitable for gasoline or fuel oil. For example, organisms were isolated that make pentane, hexane and other alkanes in the range of heptane, octane, and iso-octate from $CO_2$ and $H_2$ gases. The advantage of using isolated microorganisms is that they can be selected to produce specific hydrocarbons so that only the desired hydrocarbons are produced in a process.

Isolation procedures were as described elsewhere in this disclosure for isolation of microorganisms that can produce alkanes from $CO_2$, CO and $H_2$. Organisms were derived from the rumen of a cow and used to inoculate flasks containing 5% of one of the following as the main energy source: 1-hexane, 1-heptane, oriso-octane. These represent even and odd straight alkanes and branched chain alkanes of economic value. Each treatment was enriched in the presence of different headspace gases designed to favor degradation of the hydrocarbons: $H_2$, $N_2$ or vacuum pressure (0.05 atm). After enriching for several steps, organisms were plated to agar in serial dilutions and incubated at 39° C. for 5 to 10 days in pressure cookers with 2 atm pressure of 3:1 ratio of $H_2$:$CO_2$. Other energy sources were not included in the agar. Fifty isolated colonies were incubated in 2 to 4 atm pressure tubes containing broth without added energy source in 3:1 molar ratio of $H_2$:$CO_2$ for several weeks with alkanes measured in the headspace gas by GC every week. Exact composition of hydrocarbons in the media was measured by GC-MS after one month. Forty-six of the 50 colonies grew in broth from the headspace gas after isolation, and 41 produced specific hydrocarbons ranging in length from 3 to 8 carbons. Example hydrocarbons were: propane, butane, pentane, methyl-pentane, hexane, heptane, and iso-octane. Different isolates produced different profiles of hydrocarbons with some only producing two specific alkanes and others producing five or six alkane species. Cultures were further purified and tested again for alkane production by a similar method.

Purified cultures were identified by 16S-rRNA analysis using colony PCR. Greater than 97% homology with known strains was assumed to represent the possibility for a strain to be the same species as a published strain. Some isolates could not be identified by colony PCR. Based on these results, eleven strains isolated after enrichment in $H_2$ were similar in 16S-rRNA to Tissierrella sp. In addition, two strains of *Escherichia coli*, two strains of *Clostridium glycolicum* and one strain of *Proteus* sp. were also isolated from cultures enriched on alkanes with $H_2$ gas in the headspace. Other species were more common when other gases comprised the headspace gas during enrichment. Three strains of *Enterococcus* and two strains of *Actinomyces* were isolated when $N_2$ comprised the headspace gas during enrichment. When vacuum comprised the headspace gas during enrichment, identified organisms were *Enterococcus faecium* or *E. Hirae* (2 strains), *E. coli* (7 strains), *Proteus* (1 strain), *Actinomyces* (5 strains), and *Clostridium glycolicum* (1 strain). Most of these microbial species had been previously isolated as petroleum contaminants and were found to degrade hydrocarbons. Several were known to take up and use hydrogen. However, these results confirm that the pathways can be reversed to make hydrocarbons under higher and optimal partial pressures of $H_2$ and $CO_2$. Similarly, $H_2$ and CO could be used. The resultant isolates also grew readily on glucose media as well. A similar procedure as described could be used to isolate fiber digesting organisms or others that can also make a similar profile of alkanes or other hydrocarbons. Furthermore, these isolated organisms can be improved using mutagenesis and culturing under thermodynamically favorable conditions for alkane production. Under gas pressures, optimal ratios of $H_2$ to $CO_2$ or CO, and provision of undesired end products, mutants that produce more alkanes can be favored and allowed to grow faster as more Gibbs Free Energy can be made available to support their rapid growth.

Genetically Engineered Microbes

Specific genetic engineering (e.g. transformation) may be used to develop organisms that convert a high percentage of synthesis gases to desired products (e.g. specific length acids or alkanes). This alternative may be more expensive than the methods described as an embodiment of this invention, and needed traits such as high conversion rates, robustness, and tolerance to high concentrations of products, are complex and not well understood. If specific genetic engineering is used, the genes for undesired products may be knocked out or genes for the desired products transferred to a convenient host. Even if using genetically engineered microbes, it is necessary to consider the thermodynamics as described as an embodiment of this invention.

Without considering thermodynamics, it is not possible to drive reactions in the desired direction. Genetically transformed organisms would be similar to those from other projects in which the organisms do not produce desired products in high concentration even when genes encoding the enzymes to produce the products are transferred or up-regulated. For example, rather than isolate an organism with all the desired traits, an organism like *E. coli* could be transformed to hyper produce fuels. This is the current standard approach, which has not worked because the thermodynamics of the approach have not been considered. It may be possible to hyper produce the enzymes to make a fuel once the enzymes are discovered. The discovery of those enzymes is one embodiment of the invention. However, without considering the thermodynamics of the process, the enzymes will not catalyze the reactions in the desired direction. Another aspect of the invention is the control of metabolism to produce longer chain carboxylic acids or alkanes, whether or not organisms have been genetically engineered.

The concept that all enzyme-catalyzed reactions are bi-directional can also be used for specific genetic engineering such as transformation of organisms. This is a concept that is often misunderstood by biochemists and genetic engineers. It has not occurred to many biochemists and genetic engineers that when seeking an organism with a certain gene, for example to produce a certain product, that gene would exist in an organism with the capability of utilizing the product. For example, one can incubate a mixed culture of organisms with an alkane like iso-octane to obtain a gene to produce iso-octane from some other product. The organisms would need to be incubated with the desired compound under conditions favoring the degradation of the compound, and wherein the conversion of the desired compound to something else is a thermodynamically favored pathway. Under these conditions, the organisms that degrade the desired compound could be isolated, and such organisms would have the genes to produce the enzyme to degrade or produce the desired compound. Whether the organism is isolated from a natural environment or is genetically engineered, the products and reactants must be controlled to make it thermodynamically feasible to produce the desired concentration of the product.

Examples of Industrial Processes to Make Hydrocarbons

The invention of Directed Equilibrium process as described in this disclosure will make it possible to isolate microorganisms to produce many different products. Some products may be valuable but only needed in small quantity. Other products may need to be produced from the least expensive biomass source feasible to be cost effective. The types of biomass that might be used could include grass, wood waste, waste paper, cardboard, algae, food waste, animal and human manure, leaves, and biofuel crops. All sources of biomass identified previously (U.S. Ser. No. 12/000,856) for alcohol production could be used for any of the bioproducts that can be produce using this invention. Producing hydrocarbons from gases could include waste gas or fermentation gas, gases from heating biomass, synthesis gas, and sources of hydrogen could include electrolysis or photosynthesis in addition to other sources. Even direct provision of electricity into the fermentation with electrodes can be used. Additional products could include fertilizer, microbial protein that could be used as a feed supplement, or carbon or nitrogen trading credits.

When using a pure culture of microorganisms, the biomass may need to be sterilized by heat and pressure or with chemicals to prevent competition with other microorganisms. When heat is used, the same source of heat may be captured with a heat exchanger and shared with heat for distillation of products if necessary. Distillation may also be by using vacuum or purging with gases. It would make sense to have a mixer that can be filled with biomass intetmittently, and which feeds the feedstock into the system continuously from there. The residual biomass could include lignin and other indigestible residues, which could be used as a fertilizer or burned. One of the surprising aspects of the process is the rapid speed at which the process can occur. In the experiments conducted already, the volatile fatty acids were converted to alkanes in a matter of hours or days, at neutral pH and 39° C. The use of extreme conditions and long periods of time thought to bring about the production fossil fuels were not necessary. An industrial process may involve use of one set of microorganisms to produce the acids and a second set, simultaneously or in separate batches, to produce the alkanes from the acids. The alkanes can then be removed. Any of the process steps for other products described in this disclosure or in a previous disclosure (U.S. Ser. No. 12/000,856) for alcohol production can be used.

The use of Directed Equilibrium process facilitates the design and operation of industrial-scale bio-product production. Not only is Directed Equilibrium process used to isolate the organisms and to improve them, but it is used to define the conditions for optimal industrial production. The analysis of thermodynamics and thermodynamic data obtained for each organism that might be used can be used to select optimal combinations of organisms for given substrates or desired products. For example, some available organisms can digest ligno-cellulose in the presence of 6% ethanol, but other organisms can use more readily available carbohydrates in the initial substrate to produce 10% ethanol by volume. One set of organisms can release the sugars from cellulose while another set can use them. One substrate might be used earlier in the fermentation while a different substrate or a less digested one might be used when the ethanol concentration is higher. The data obtained by determining what substrates can be used at what concentrations to produce what products, and the way in which the thermodynamics defines the use, makes it possible to control fermentation as described as an aspect of this invention.

Example Process to Make Gasoline from Synthesis Gases

One example application for the proposed process is to use microorganisms to convert $H_2$ and either one or both of $CO_2$ and CO to alkanes that will be identical to components of gasoline. The production of both straight and branched chain alkanes ranging from $C_5$ to $C_{12}$ is contemplated. The process can be designed to target any desired length of alkane such as $C_8$ alkane with as many branches in the chain as desired. Such a liquid fuel has a research octane number exceeding 85, heat of vaporization greater than 0.5 MJ/kg and energy density of greater than 40 MJ/kg. It would be a high-value component of gasoline or airplane fuel.

The process to produce gasoline from gases would be able to use various sources of gases depending on availability and price. In some cases the process would be accelerated by pressurizing the system to a few atmospheres or by mixing different sources of gases to obtain a desirable ratio, however once the organisms are selected and developed, the exact composition of gases is not critical. In addition, sources of gases that contain potential contaminants (e.g. sulfide) are also acceptable. The incubation media and culture may be sterilized with heat and pressure using standard methods before fermentation, and be kept closed to outside contaminants. The mixed gases may be filtered through a 0.2-micron filter to remove potential microbial contaminants before feeding the reactors containing the developed microorganisms. However, it may be necessary to sterilize the system if the conditions are appropriately defined and maintained to keep the favored organisms and pathways prevalent.

The reactor vessels would be heated to an optimal temperature for growth. Typically a temperature of 40° C. is used, but lower or higher temperature may also be advantageous. Gas may be bubbled into the reactors through a gas disperser on a rotating arm. Such reactors are frequently used, especially for aerobic fermentation wherein the gas is oxygen or air, but in this case the gas would be $H_2$ and $CO_2$ or CO. Other methods of solubilizing the gas can also be used such as fixed bubble dispersers or tubing, mixing, vibrating, or recirculating liquid, and maintaining high surface area. The same filtered gas is re-circulated from the headspace, and gas can be replaced as it is used to maintain the desired pressure. An aqueous broth in the reactors contains simple nutrients (e.g. ammonia, minerals, cofactors). Some microbes can digest and use microbial protein while others synthesize protein from the infused gases and ammonia. Both options have their advantages depending on needs of the market. Including an organism that digests other microbes at a controlled rate decreases the need to replace nutrients, but also decreases the activity of the organisms using the synthesis gases. On the other hand, if the proteolytic activity is minimized the accumulated microbial protein can be removed periodically and the nutrients replaced. The microbial protein can be separated and used as a high-value animal feed. Microbial protein comprises the type of protein ruminants consume (as it is synthesized in their rumens), and it has a high biological value because of its favorable amino acid ratio and high digestibility.

One approach to make gasoline is to use microorganisms for a two-step process. For example, caproic acid ($C_6$:0, a.k.a. hexanoic acid) from rumen fluid were isolated. The caproic acid can be converted directly to n-hexane and pentanes. Some existing microbial isolates produce branched chain carboxylic acids, and the conversion of straight-chain carboxylic acids to alkanes resulted in branched isomers. Therefore, the production of caprylic acid ($C_8$:0, a.k.a octanoic acid), capric acid ($C_{10}$:0, a.k.a. decanoic acid), and branched-chain acids and their conversion to high-octane gasoline components like isooctane is contemplated. However, microorganisms that produce the same alkanes directly from synthesis gases were also isolated.

Example

Chemical Conversion of Carboxylic Acids to Alkanes

An alternative way to produce gasoline from short-chain carboxylic acids would be to produce the carboxylic acids through fermentation and convert them to alkanes with chemical or electro-chemical procedures. For example, chemical decarboxylation or hydrogenation is contemplated for conversion of carboxylic acids to alkanes. In addition, short-chain carboxylic acids can be converted to medium-length alkanes via decarboxylative dimerization through electrolysis (a.k.a Kolbe electrolysis). In Kolbe electrolysis, two carboxylic acids are joined to produce a single alkane. Using electrolysis, the carboxyl group of the acids is removed releasing $CO_2$ and free radicals of the alkyl group. The free radicals join each other to produce an alkane. For example, two acetic acid molecules ($C_2$:0) would be converted to $2CO_2$ and ethane ($C_2H_6$). The process can convert carboxylic acids of varying chain length and is energetically efficient and converts a high percentage of the acids to the desired alkane. A major co-product may be hydrogen, but this product can be used in the carboxylic acid synthesis step.

The short-chain carboxylic acids produced in this project may be dimerized to form liquid alkanes that comprise gasoline components. For example, butyrate is already a predominant volatile fatty acid from some isolates that use $CO_2$ and $H_2$, and excellent fiber digesters that mostly produce butyrate from cellulosic biomass were isolated. This butyrate ($C_4$:0) could be converted to n-hexane, an industrial solvent and gasoline component as described in a U.S. Patent publication number 2007/095215, which is incorporated herein in its entirety. Microorganisms that were isolated and described in a PCT patent application incorporated herein by reference (PCT/US10/29707) could be used this way, as organisms that produce about equi-molar concentrations of valerate, butyrate and acetate, and some organisms that produce significant concentrations of iso-valerate from $CO_2$ and $H_2$ were isolated. Other organisms the inventor isolated mostly produce butyric acid, and others could be isolated using the approach described in this application to produce longer-chain acids. Increasing the conversion efficiency to these longer chain acids in isolated microorganisms is contemplated. It may be efficient to convert carboxylic acids with 4 to 5 carbons to alkanes. For example, conversion of valerate ($C_5$:0) to alkane by Kolbe electrolysis would create n-octane, and dimerization of isovalerate to alkane would yield 2,5-dimethylhexane, a high-octane component of gasoline and aviation fuel. Rumen microbes, including major fiber digesters, are known also to produce large quantities of the dicarboxylic acid succinate, which is transferred to other organisms and decarboxylated to propionate. Kolbe electrolysis with a dicarboxylic acid will produce polymers of long chains of alkanes, but Kolbe electrolysis of a mixture of 50% succinate and 50% butyrate would produce a mixture of alkanes mostly in the range from $C_6$ to $C_{12}$, which would be gasoline components. Thus, organisms that have been already isolated can produce carboxylic acids that can be converted to gasoline components through Kolbe electrolysis.

Example

Alkane Gases

Gaseous alkanes ($C_1$ to $C_4$) in the gas phase from mixed culture fermentation of volatile fatty acids were measured. Production of methane by anaerobic digestion is well known and a useful biofuel production process. It is currently the only consolidated bioprocessing method for direct microbial conversion of plant fiber to biofuel that doesn't require a pretreatment. One of the advantages of methane production is that methane can easily be separated out from the aqueous media because it is volatile. However the cost of gas conditioning and compression is significant. Slightly longer alkanes (ethane, propane and butanes) are desirable because of their lower boiling points thus making them easier to compress, store and use, and also because of their higher energy density. Yet they are still easily removed from the fermentation liquid. In addition to producing longer alkanes that would be liquids at room temperature, isolation and improvement of organisms that produce shorter alkanes that live in the rumen in mixed cultures is also contemplated.

It has been discovered that alkanes can be produced by microorganisms from biomass in a matter of a few days incubation under the correct conditions. They have discovered these organisms exist in the rumen of a cow among other places. They have established the conditions (optimal ratio of $H_2$ to $CO_2$, pressure greater than 2 to 4 atm or greater) that shift the fermentation to produce the alkanes, and these conditions were used to isolate organisms that carry out the reactions. Using the process of Directed Equilibrium, alkane-producing organisms were used to produce alkanes from biomass or synthesis gases.

Example

Greater and Faster Fiber Digestion and Adaptation to Different Substrates

Production of fuels or other bioproducts from biomass may utilize the digestion of the biomass. In the case of some forms of plant fiber such as cellulose or hemicellulose, microorganisms that can rapidly degrade the plant fiber need to be selected and used that can degrade the biomass and convert it to the desired final product. In this case it is necessary to select for both high levels of fiber degradation as well as for the specific product that is necessary.

Measurement of the digestion of plant fiber (e.g cellulose, hemicellulose, etc.) is accomplished by measuring the change in plant fiber over time during the digestion. Plant fiber generally refers to neutral detergent fiber or NDF and pectin but can also refer to acid detergent fiber or ADF when indicated. These fiber fractions represent the dried residue after boiling in pH-7 or acidic detergents for one hour and filtering. Procedures were used in accordance with Goering and Van Soest (1970 as cited) as modified by the Mertens (2002, Gravimetric determination of amylase-treated neutral detergent fiber in feeds with refluxing in beakers or crucibles: Collaborative study. J. AOAC 85:1217-1240), which are incorporated herein by reference. The NDF fraction includes cellulose, hemicellulose and lignin, and sometimes insoluble or denatured proteins and ash. The ADF fraction includes cellulose and lignin, and some insoluble ash and heat-damaged protein. Lignin is measured by dissolving ADF in concentrated sulfuric acid for 3 hours.

For AVICEL® microcrystalline cellulose, which is pure cellulose, the ADF and NDF before digestion is nearly 100%. For the timothy hay that was used, the NDF was 60%, ADF was 32%, and lignin was 6.8% when each was determined sequentially. Neither sample comprised much protein or ash. Therefore, hemicellulose could be estimated from the difference between NDF and ADF, and the cellulose was the difference between ADF and sulfuric-acid lignin. The change in the NDF or components (e.g. cellulose, hemicellulose) was determined as the degradation. The extent of degradation refers to the amount of NDF or ADF residue degraded within 5 d, and the percentage not degraded is referred to as the indigestible residue. The rate of degradation refers to how fast the fraction disappears calculated as the slope of the line when regressing the natural logarithm of the residue vs. time until the residue is nearly degraded to the indigestible residue. The rate is best determined when the microorganisms are supplied at a high inoculation dose so that microbial growth does not limit digestion. In other words, adding more microorganisms of the same strain would not further increase the digestion rate. Better digestion can therefore refer to either faster or to a greater extent. In some cases, initial comparisons can be made among organisms because of a rapid disappearance by the first sampling at 24 hours. For example, some organisms digest all the digestible material within 24 hours.

One aspect of the invention is the method to enrich and select for microorganisms that rapidly and nearly completely digest sources of plant fiber to make desired products. In addition to the enrichment and selection protocols already described (U.S. Ser. No. 60/870,441; U.S. Ser. No. 12/000, 856; U.S. Ser. No. 61/113,337; U.S. Ser. No. 12/385,215) in which some alcohol-producing fiber-digesting microorganisms were isolated, improvements were made to isolate additional organisms that were very fast at digesting fiber. Although previous approaches produced fiber-digesting organisms that made alcohols, modifications to the procedure described below resulted in a higher percentage of the isolates being efficient at degrading sources of plant fiber such as the fiber component of grass (timothy hay) or cellulose.

Enrichments and isolations were conducted in which timothy hay or timothy hay NDF or timothy hay ADF were used as the only energy substrate. Alternative substrates included paper or AVICEL® microcrystalline cellulose. The concept was to select specifically for microorganisms that could digest the hemicelluose and ligno-cellulose in the hay or feedstock of interest. After the colonies were isolated on agar with ground filter paper, carboxymethyl cellulose, or AVICEL® microcrystalline cellulose, the isolates were screened by growing them in broth with a strip of filter paper. In this way, it was easy to see immediately which isolates could degrade the paper. Some isolates degraded all the paper within one day. Testing of isolates also used filter paper, AVICEL® microcrystalline cellulose, timothy hay, or timothy hay NDF or ADF. In the latter cases, the fiber was extracted before the digestion, and extracted again on the same sample after digestion to measure the disappearance. However, the disappearance of fiber from timothy hay was also measured by subjecting the residue of fermentation of the hay to fiber analysis and comparing to the original amount of fiber estimated from a different paired sample of the forage. Avicel, filter paper, or timothy hay were digested and the NDF, ADF, and lignin determined sequentially at each time point. The disappearance of cellulose and hemicellulose were determined as the disappearance over time. In other respects these enrichments and isolation procedures were as described previously.

Microorganisms were characterized for their ability to digest fiber quickly and to a large extent. The digestion of cellulose from a source such as filter paper or Avicel is accomplished by measuring the ADF at different time points in the digestion. For example, ADF may be measured at time=0, 1, 2, 3, or 5 days. If the starting material is Avicel or filter paper, at time=0 the ADF and NDF were both nearly 100%, and each decreased as a percentage of the initial material over the course of the digestion. The NDF of Avicel decreased to about 15 to 20% of the original dry matter for the better fiber digesters. The ADF of Avicel decreased to 10 to 15%. Some of the apparent residue after Avicel digestion may have been endogenous or produced by the microbes themselves. If the starting material is timothy hay, for example, the starting NDF depends on the maturity of the grass. In the case of these experiments, the NDF of the timothy was 60% (dry matter basis). The timothy NDF decreased to about 18% of original feed dry matter. The ADF decreased to about 14% of the original dry matter. The timothy hay was also comprised of 6.8% lignin, which did not seem to disappear during digestion. Most isolates digested these feedstocks within the first two days, some within the first day, and others were slower. Thus, the isolates could digest purified cellulose and lignocellulose, and hemicellulose. Mixed rumen contents and *Ruminococcus albus* (strain 7) were also compared to the new isolates. Some of the new isolates were surprisingly faster at digesting timothy cellulose (ADF minus lignin) and hemicellulose (NDF minus ADF) than *R. albus*, and even faster than mixed rumen fluid. Some isolates were more tolerant than others to reductions in pH. It was important to neutralize samples by NaOH in some cases to maintain pH near 6.8. Thus, it is clear that organisms isolated using the methods described are able to digest pure cellulose, hemicellulose, ligno-cellulose in pure or natural font's. Some of the isolates could produce ethanol, and one isolate that could digest all forms of cellulose and ligno-cellulose presented, produced greater than 10% ethanol by volume, converting most of the cellobiose in the solution to ethanol.

Enrichment. Some example enrichments for fiber digestion include the following. Timothy hay was the substrate with 1 atmosphere $H_2$ gas in the headspace. This enrichment selected for organisms that can digest components of timothy hay and which take up $H_2$ and produce products like propionate or propanol which use $H_2$, and to select against the more common fiber-digesters that release $H_2$. Initially, various concentrations of ethanol were used with each source of carbohydrate. For example, timothy hay under $H_2$ was incubated with 6% ethanol or 10% ethanol as well as no ethanol. The enrichment with ethanol selected for organisms that were tolerant to ethanol. However, some organisms can grow by utilizing the ethanol as an energy source. Therefore, other treatments alternated enrichments between having high ethanol concentration and not having ethanol added. In this way, the organisms that digest the fiber source were selected for but those intolerant to ethanol were subsequently selected against. The same could be done with other alcohols, specific acids, or alkanes or other compounds. The gas phase also included $CO_2$, $N_2$ or air. When combining these gases with ethanol, selection was for organisms that could metabolize the ethanol. In air, this ethanol might be aerobically oxidized to $CO_2$ and $H_2O$. However, the same organism would make ethanol under anaerobic conditions, and be tolerant to air and ethanol to facilitate its use. Some enrichments alternated air and hydrogen to select for organisms that could grow in either situation. One enrichment used timothy hay or Avicel with hydrogen and no ethanol alternating with the same carbohydrate under air with 6% ethanol. Alternating the enrichments this way selects for organisms that have alternative pathways for aerobic and anaerobic conditions. They need to degrade the substrate and may be aerobic, but they produce ethanol anaerobically. The same principle can be used for other alcohols, acids or for alkanes.

Isolation. In addition to the procedures described in U.S. Ser. No. 61/113,337 and U.S. Ser. No. 12/385,215 for isolation of microorganisms, several modifications were discovered to result in a higher percentage of the isolates being excellent fiber-digesting microbes. Isolation on complex source of fiber, rather than cellobiose, was used. Ground filter paper, AVICEL® microcrystalline cellulose, carboxymethyl cellulose or other source of fiber was used as the main carbohydrate in the roll tubes used for isolation. The other aspects of the isolation were as described previously. In the present case, only organisms that can grow on these substrates would be selected in the colonies that result. The contents from the previous enrichment were diluted to $10^{-10}$ to $10^{-14}$ and distributed to roll tubes with different gas composition. Independent colonies were selected from these. Although fiber-digesting microbes could be isolated using cellobiose as was frequently done previously. Many of these isolates were not good at digesting complex sources of fiber. The practice of using paper, grass NDF, AVICEL® microcrystalline cellulose or carboxymethyl cellulose provided a much higher percentage of the colonies that could digest cellulose.

Screening. To further improve the ability of the organisms to digest fiber, a simple screening step was used. The newly isolated colonies were grown on filter paper. A small strip of filter paper (e.g. Whatman #54) was added to the broth with the isolated microorganism. Within 1 to 3 days, fiber-digesting species would visibly degrade the filter paper, and be selected for further analysis. The products of the degradation could be measured using a gas chromatograph, and in some cases a single volatile fatty acid or alcohol predominated. The cultures were also used to digest other forms of biomass and the products were measured.

Mixed rumen fluid was inoculated to timothy hay or Avicel in the presence of 6% ethanol. After several dilutions, microbes were isolated from mixed rumen fluid enriched by digesting timothy hay or Avicel in the presence of 6% ethanol or greater. Six isolates readily digested filter paper in the presence of 6% ethanol. These results are important because they show that the organisms could digest plant fiber or paper in the presence of a high concentration of ethanol. Such organisms can be used with other organisms (e.g. yeast) to produce ethanol when they don't produce ethanol themselves. Although fiber-digesting microorganisms that produce ethanol in a high concentration were isolated, it is also recognized that a viable alternative to one organism that digests fiber and produces ethanol is an organism that digests fiber and makes sugars available to another organism that can make ethanol. Of course, it is helpful for the fiber-digester to be tolerant to ethanol, and that it be able to digest fiber in the presence of ethanol, so that the ethanol produced by the different organism will not prevent the digestion of fiber.

The previous isolations described in U.S. Ser. No. 61/113,337 and U.S. Ser. No. 12/385,215, focused on isolating fiber-digesting organisms that could produce alkyl alcohols. The present invention focused on improving the rate and extent of fiber digestion. However, the methods to obtain the desired product can still be applied. With the previous methods, for example, many of the organisms isolated on cellobiose were not well adapted to digest cellulose or other larger components of plant fiber. Organisms that digested plant fiber were enriched for, but many of the organisms in this consortium were cross feeders that consumed the mono- or di-saccharide released by the fiber digesters. These cross feeders could be useful in their own right, but also isolating excellent fiber digesters is important. By using cellulose or other complex carbohydrate in the media for isolation, we were assured to obtain mostly fiber digesters. Other isolations using cellobiose or sugars after the same enrichments could produce the cross feeding organisms.

In summary, the described process of Directed Equilibrium enabled selection for very effective fiber-digesting bacteria that digest plant fiber in the presence of high concentrations of ethanol, and that convert most cellulosic biomass presented to ethanol even when ethanol concentration was greater than 10% by volume. Some isolates produced ethanol and 1-propanol or 1-butanol directly from timothy hay or cellulose Example Increasing Tolerance to Alkyl Alcohols Previous disclosures (U.S. Ser. No. 61/113,337 and U.S. Ser. No. 12/385,215) by the inventor described methods to increase the tolerance of microorganisms to products such as alkyl alcohols. One aspect of tolerance of a microorganism to alkyl alcohols is the ability to grow readily in the presence of some concentration of the alcohol. Organisms were considered tolerant if they could continuously grow nearly as fast as without the alcohol in the media, where "nearly as fast" means at least half the rate of growth as without the added alcohol. Based on the amount of time that elapsed, the rate of growth would have meant doubling at least every one to two hours. Ability to grow in alcohol might be an indicator of tolerance, but some organisms might show other signs of tolerance even if they do not grow in that level of alcohol. For example they may digest fiber or produce more alcohols without continuing to grow.

In addition to being able to grow at the high alcohol concentration, the microorganisms could be made to convert a high percentage of the carbohydrate (e.g. 50%) to the alcohol while in the presence of a high concentration of alcohol. Usually, this requires production of the alcohol to be thermodynamically favorable over other pathways in the fermentation, but as other pathways can be eliminated in pure cultures of organisms it is not difficult to achieve these conditions.

Another aspect of tolerance to a high concentration of alcohol refers to the ability to digest and grow on a certain substrate such as plant fiber (e.g. paper, purified cellulose, grass, grass fiber) in the presence of a high concentration of alcohol. The inventor previously disclosed (U.S. Ser. No. 12/385,215) methods to manipulate microorganisms for all of these aspects of alcohol tolerance by considering the thermodynamics. Examples for production of lower alkyl alcohols are provided in U.S. Ser. No. 60/870,441; U.S. Ser. No. 12/000,856; U.S. Ser. No. 61/113,337; U.S. Ser. No. 12/385,215 which are incorporated herein by reference. Prior to Directed Equilibrium, only a few microorganisms have been found that could produce lower alkyl alcohols from components of plant fiber, and they only produced low concentrations of alcohols and were not alcohol tolerant. Some of the organisms such as *Clostridium thermocellum, Clostridium phytofermentans*, and *Ruminococcus albus* were compared. These other organisms were not isolated specifically to make ethanol from plant fiber, and they mostly make other products like acetic acid and they are not ethanol tolerant. Even if an organism is able to digest fiber readily, and it can convert glucose to a high concentration of ethanol, it needs to be able to digest the fiber to a high enough concentration of intermediate (e.g. glucose) so that the intermediate can be converted to a high concentration of ethanol. Again, the thermodynamics is important to this reaction. For example, the natural mechanisms for decreasing cellulose digestion in the presence of high glucose concentrations need to be overcome.

Although it may be assumed that organisms might be adapted to tolerate greater concentrations of alcohol by slowly increasing the alcohol concentration, the production of alcohol under these conditions may become thermodynamically infeasible. If the thermodynamics is not considered to manage the concentrations of products and reactants during the adjustment, the organisms may adapt by producing a different product. The concept of adapting microorganisms to higher concentrations of product is not new, but U.S. Ser. No. 61/113,337 and U.S. Ser. No. 12/385,215 introduced the means to adapt the microorganisms to this greater level of product while maintaining conditions (product and reactant concentrations) so that the organisms can obtain energy and grow under these high concentrations by producing the desired product. Failing to adjust the product and reactant concentrations accordingly could cause the microorganisms to lose their ability to produce the desired product. An aspect of directed evolution is the means to isolate and adapt organisms to high ethanol or butanol concentration by manipulating reactants and products to maintain production of ethanol or butanol by keeping those products thermodynamically favorable during the adaptation.

It has been discovered that mixed rumen cultures could degrade plant fiber (e.g. timothy hay fiber) or AVICEL® microcrystalline cellulose in the presence of 6% ethanol or 4% butanol by volume showing that at least some individual organisms were able to do so, and they isolated at least six strains that degraded filter paper (cellulose) with 6% ethanol in the media. Even if the microorganisms cannot produce ethanol themselves, they can be used to digest biomass and release sugars for other organisms to use (cross feeders). However, many microbial isolates were shown to produce more than 6% ethanol by volume, and one very effective fiber digester which was isolated on filter paper (KK395) was able to increase ethanol to 10.6% ethanol concentration by volume. Many other isolates including some that grew in 10% ethanol are likely to have also been able to increase ethanol concentration above 10% by volume but results were not measured. The production of even higher concentrations of ethanol from cellulosic biomass is contemplated by adapting existing organisms or isolating others to higher ethanol concentrations while maintaining conditions to favor greater ethanol production. Some microorganisms such as can be adapted to as much as 20% ethanol by volume, and understanding and using the Directed Equilibrium process while improving microorganisms will enable a person of ordinary skill in the art to approach that limit.

In addition to the methods previously disclosed (U.S. Ser. No. 12/385,215) to isolate or improve microorganisms to make them useful to consolidated bioprocessing for ethanol or other product production, producing a high concentration of product may require producing a high concentration of the intermediate. Microorganisms need to be isolated or adapted to produce a high concentration of the intermediate. An example isolation is to use a mixed culture of microorganisms and initial conditions with relatively high concentrations of all the known products in that mixed culture. For example, the enrichment or isolation media can have relatively high concentrations of major VFA and alcohols. In order to obtain energy, each species of microorganism needs to produce a higher concentration of the products, which will only be feasible with a higher concentration of the intermediate (e.g. glucose). If the intermediate is produced from the digestion of the source of biomass (e.g. cellulose), this digestion will need to continue until the higher concentration of the intermediate is produced. In this way, only the organisms that can digest the biomass to release a high concentration of intermediate will survive. Thus, incubating the microorganisms in the presence of high concentrations of the known products enriches, selects for, or develops microorganisms that produce higher concentrations of the intermediates. The inventor observed that some isolated organisms could produce higher concentrations of a certain product (e.g. ethanol) from added cellobiose than from added cellulose. These organisms are especially suited to adaptation to producing a higher concentration of ethanol from cellulose by adapting them slowly to higher concentrations of ethanol under conditions that favor conversion of carbohydrate to ethanol (e.g. CO or $H_2$ pressures).

Most natural feedstocks are not comprised of only cellulose. For example, grass is comprised of lignin, cellulose, hemicellulose, pectin, starch, fructan, sugar, protein, etc. Some microorganisms can digest the cellulose or hemicellulose to a moderately high concentration of ethanol, while the same organisms or others may be able to convert the starch or sugars to an even higher concentration of ethanol. Some of the organisms isolated could be used at a lower concentration of ethanol to digest the cellulose or hemicellulose, and then additional grass added to achieve the higher ethanol concentration from the more digestible components. After separation of the ethanol, the residual grass (cellulose, hemicellulose) could be digested again at the lower ethanol concentration. This process could be used to take advantage of the different capabilities of microorganisms for a number of different products including other alcohols or acids. The higher concentrations might even be achieved using synthesis gases. Thus, an aspect of the invention is to use the microorganisms at what they can do best. This is another example of why a mixed culture is particularly advantageous, but also an example of digesting mixed substrate and not focusing only on the cellulose.

Thus, it has been demonstrated the isolation and improvement of microorganisms under conditions that make it possible for those organisms to grow in the presence of 6% to 10% concentration of ethanol by volume, or 4% to 6% butanol by volume. Another aspect of the invention is the means to isolate and improve organisms that grow under these high concentrations of ethanol (e.g. 6 to 10%) while producing additional ethanol. Another aspect of the invention is the means to use microorganisms to digest different types of feedstock (e.g. paper, grass hay, sugars released by another organism, or other source) when incubated with high ethanol concentrations of the alcohol (6 to 10%). And finally, an aspect of the invention is the means to digest various types of feedstock and convert it directly to ethanol at a high concentration.

Example

Producing Specific Predominant Carboxylic Acids

Producing a certain volatile fatty acid may be advantageous over producing a mixture of acids because it may be more cost effective to separate the more homogenous acid or it might be converted to another product. For example, acetate might be converted to ethanol or butyrate to butanol either by fermentation or a chemical process. Or a certain volatile fatty acid might be converted to a certain alkane either by fermentation or a chemical process.

Most microbiologists accept that certain types of substrate favor certain volatile fatty acids. For example, acetic acid is associated with fiber and lactic acid and propionic acid are associated with starch digestion. This assumption would imply that it would be more expensive to produce lactic acid or propionic acid because the feedstock would be more expensive. The isolated microorganisms that are currently known for these processes confirm these assumptions.

It has been disclosed herein that using Directed Equilibrium process, they have been able to shatter this assumption.

Microbial isolates selected under conditions that favor acetate production (e.g. low $H_2$, low $CO_2$) produce mostly acetate irrespective of substrate. Microorganisms isolated under conditions of high $H_2$ can convert heterogeneous plant fiber sources, or cellulose, predominantly to propionate, or several very efficient fiber-digesting bacteria converted greater than 80% of the cellulose to butyric acid and $CO_2$. Mass spectrometry and $^{13}C$-labeled acetate were used to show that microorganisms in rumen fluid could convert two acetate molecules to butyric acid. Selecting for such organisms would employ incubation with acetate and $H_2$. Although rumen fluid is known to produce a mixture of volatile fatty acids, predominantly acetic acid, propionic acid and butyric acid from many different types of substrate, a way to produce any of these desired volatile fatty acids from many different substrates using bacteria that can digest biomass very efficiently and produce predominantly any one volatile fatty acid was discovered.

Typically other scientists use conditions of isolation and use thereafter to mimic the conditions of the natural environment. Therefore, the isolated organisms produce an array of products, similar to a mixed culture in the natural environment. Some existing isolates do produce specific VFA from certain forms of carbohydrate, but finding these particular isolates may have been a matter of luck. Using the Directed Equilibrium process, unusual isolates that are not typically found can be isolated as well. These include microorganisms that digest one or many forms of biomass and convert it to a similar narrow array of products.

The process for biomass digestion and enrichment or isolation for a particular VFA was as described in the section on fiber digestion except the conditions in the fermentation would also include addition of gases and other metabolites to make production of a certain VFA thermodynamically favored. For example, while the pH is maintained near 6.8, fiber digesters that produce propionate are enriched for by perfusing with $H_2$ gas and including acetic and butyric acid at physiological levels (e.g. 100 mM) without propionate. Other acids, and other gas composition could also be used for other VFA. In contrast, a microorganism to produce butyrate from acetate is grown with low butyrate concentration but higher concentrations of acetate and perfusion of $H_2$, but butyrate from glucose (or cellulose) employs lower $H_2$ perfusion and provision of VFA other than butyrate. The observation that whatever VFA is missing is likely to be produced in a mixed culture supports the concept of the method to obtain microbes that produce a certain VFA. Therefore, by using the appropriate mixture of metabolites and gases, it is possible to enrich and select for organisms that preferentially produce a certain VFA.

The novel aspects of this invention regarding commonly known volatile fatty acids are:

Individual strains of microorganisms from the rumen can digest biomass as rapidly and to the same extent as mixed rumen fluid.

Some of these strains also produced predominantly one volatile fatty acid (e.g. acetic acid and $H_2$ and $CO_2$, butyric acid and $CO_2$ and $H_2$, propionic acid while consuming $H_2$ from the plant fiber they digest (i.e. Avicel, Timothy ADF).

Strains have been isolated that produce specific volatile fatty acids from plant fiber, including fiber-digesting bacteria that predominantly make propionic acid from plant fiber.

Strains were adapted to produce higher concentrations of the volatile fatty acids from plant fiber than they originally produced.

Thus, using the process of Directed Equilibrium has enabled the enrichment and selection of microorganisms that produce certain favored volatile fatty acids. The use of such cultures to produce certain bioproducts is also contemplated. In particular, using diverse feedstock and converting it to a predominant acid is contemplated. For example, a microbe might be used to produce acetic acid, hydrogen and $CO_2$. Microorganisms that assimilate $CO_2$ and $H_2$ into additional acetic acid were also discovered, so a process to produce acetic acid could be more efficient by combining the different strains. The acetic acid could be precipitated by calcium hydroxide and separated for an industrial process or converted to ethanol or butyrate by either feinientation or a chemical reaction. Conversion of acetic acid to ethanol or butyric acid to butanol were noted as a means to produce ethanol from plant fiber (U.S. Ser. No. 60/870,441 and U.S. Ser. No. 12/000,856) but the isolated microbes in the present disclosure further improve this procedure.

Using methods previously disclosed (U.S. Ser. No. 60/870,441 and U.S. Ser. No. 12/000,856) to isolate microorganisms to produce specific volatile fatty acids produced results that might be considered surprising. The conditions of isolation favored organisms that used certain substrates to produce certain products, and therefore in accordance with the theory that fermentations are near equilibrium and using the process of Directed Equilibrium, we would expect to isolate organisms that were selected for. However, the surprising aspect of the results is that the isolated organisms differed from all previous isolates.

One microorganism isolated on AVICEL® microcrystalline cellulose under $H_2$ pressure was a fiber-digesting microorganism that produces propionate as its primary product. It would be necessary to continually add $H_2$ to maintain the organism in isolation. However, organisms that produce propionate from plant fiber were not previously known. It was thought that such organisms needed starch or sugar as substrate. It is contemplated that an organism like this could be used to produce a high concentration of propionate which can be used to make propanol or a bio-plastic or which can be converted to lactic acid for a different process. The organism might be added to silage or to cattle diets to shift fermentation toward the more efficient propionate production while decreasing methane emissions from the animals.

Several isolated microorganisms produced butyric acid as the main product of cellulose or cellobiose. Several of these strains were able to digest up to 80% of timothy hay in 5 days or nearly all cellulose in as much time. Cellulose was digested by isolated rumen microbes to produce butyrate concentrations exceeding 2% by volume, and these concentrations can be increased by adapting the organisms to higher concentrations. The organisms isolated could be used to produce an initial lower concentration of butyrate from cellulose or hemicellulose, and then new mixed substrate or other substrate could be added to produce a higher concentration if necessary. No previously known microorganisms that are highly efficient at digesting plant fiber predominantly produce butyric acid. Butyric acid may be converted to butanol either by fermentation under thermodynamically favorable conditions or a chemical process. Predominantly producing butyric acid from plant fiber may require removal of the excess hydrogen and carbon dioxide. Using the isolated organisms could also require sterilization of the substrate and media to prevent other organisms to grow in the culture. The butyric acid could be converted simultaneously or separately to butanol, a desired alcohol. Thus, the current invention shows the potential to produce butyric acid from any number of waste products using fiber-digesting bacteria. Butyric acid is known to be a favored acid in human and animal nutrition because is provides energy to maintain a healthy gut metabolism, and it is associated with lower cancer risk. Thus, organisms like this might be developed as probiotics to improve digestion. There are many medical, nutritional, and industrial uses of butyric acid, but it is currently produced from fossil fuel or from glucose using microorganisms.

One very surprising strain of bacteria enriched by digesting plant fiber under a high concentration of $H_2$ converted plant fiber to predominantly produce butyrate and valerate, an uncommon 5-carbon volatile fatty acid. It appeared to elongate shorter volatile fatty acids, and may also produce longer chain fatty acids that were not yet measured.

The inventor isolated organisms that could digest cellulose to produce predominantly acetic acid, $CO_2$ and $H_2$. Acetic acid-producing bacteria are frequently isolated from mixed cultures and acetic acid is known to be produced from plant fiber. However, the process of Directed Equilibrium produced organisms that mostly produced acetic acid and $CO_2$ and $H_2$. In this case, keeping the concentrations of acetic acid and $H_2$ low favors their isolation. The organisms could become particularly useful because they produce few other products, and because they could be adapted to produce a high concentration of acetic acid from substrate such as plant fiber. Again, increasing concentration of any product including acetic acid might inhibit digestion of plant fiber as it becomes important to adapt the enzymes and the genomics of the organisms to digesting fiber in the presence of higher concentrations of product or intermediate (e.g. glucose or cellobiose). The inventor also isolated organisms that produced acetic acid from $CO_2$ and $H_2$. Thus, a co-culture or sequential cultures could be used to produce 3 acetic acid molecules per glucose. Alternatively, the acetic acid bacteria could be used to produce acetic acid, $CO_2$ and $H_2$ and the $CO_2$ and $H_2$ used for another process. The $H_2$ could be used in a microbial fuel cell separately or together with the acetate-generating reaction. The $H_2$ could be removed and used as fuel itself. A high partial pressure of $H_2$ can be produced together with acetic acid, or a lower partial pressure of $H_2$ can be produced by removal of the $H_2$ through vacuum pressure or perfusion of other gas or through use of membranes. The lower $H_2$ pressure would shift fermentation to favor lower concentrations of acetic acid. Typically, rumen microorganisms can digest filter paper with greater than 1% acetate in the solution prior to being adapted to higher concentrations.

Other acids are also known to be produced in fermentation and have various uses. For example, succinic acid is passed from one organism to another in mixed cultures, and it can be produced predominantly through a process of Directed Equilibrium and management of the inputs and outflows from the process.

The process for using any microbial culture to produce a desired acid would be similar to the process for producing alkyl alcohols except different products and reactants would be manipulated to thermodynamically favor the desired products. In order to prevent wild organisms from taking over the digestion, a sterilization step may be needed. The feedstock would be sterilized by heat and pressure or chemicals for example. The microbial inocula would be added along with any co-substrates. For example, $H_2$ would be added to favor propionate. Products, especially gases may be removed to increase the rate of the reaction, the rate of growth of the desired microbes, and to help the reaction digest a greater amount of substrate and produce a higher concentration of product. The pH would be monitored and adjusted by adding buffers or bases during the digestion. The acids could be removed by addition of calcium hydroxide to precipitate out excess acid and deliver it to a subsequent process.

Example

Greater Growth Rate of Methane-Producing Organisms

Currently, anaerobic digesters are used to produce methane gas as a fuel from biomass such as manure. The methane gas is produced from conversion of acetic acid ($CH_3COOH$) to $CH_4$ and $CO_2$, or from conversion of $4H_2$ and $CO_2$ to $CH_4$ and $2H_2O$. Anaerobic digesters are known to be unstable and at times stop to producing desired gases. Usually the pH in the digester declines which prevents biomass digestion. Even if the pH is maintained, a high concentration of VFA including acetic acid can inhibit methane production and biomass degradation. A common factor leading to a crash in the digester is the loss of methane-producing organisms. If the organisms that degrade acetic acid decline, the acid builds up and causes the malfunction. If the organisms that convert $CO_2$ and $H_2$ to $CH_4$ decline, the accumulation of $H_2$ and $CO_2$ prevents the degradation of acetic acid, or results in its synthesis, also leading to the crash. Commonly, it is believed that methane producers grow very slowly. Therefore, in order to prevent digesters from crashing, the flow rate of biomass or liquids through the digester must be very slow or the methanogens must be retained in some other way.

The application of Directed Equilibrium was shown to rapidly increase the rate of methane production and degradation of acetic acid. In a previous disclosures (U.S. Ser. No. 60/870,441; U.S. Ser. No. 12/000,856), rate of methane production was accelerated by removing methane, perfusing with $H_2$ or $N_2$, or applying vacuum. In each case, the production of methane was increased by making the $\Delta G$ for methanogenesis more negative, either by removing products or adding reactants.

The application of the process of Directed Equilibrium empirically increased methane production rate as the $\Delta G$ was made more negative. The $-\Delta G$ represents the amount of free energy available for methanogens to make ATP. Under typical natural conditions, the $\Delta G$ for methane production only allows for about 0.2 ATP to be produced per mole of methane produced, and if conditions disturb the organisms (e.g. slightly low pH), even less ATP can be produced. The ATP is used for microbial growth. Therefore, the low capture of energy results in a low microbial growth rate for the organisms dependent on producing methane to capture energy. However, if the gas concentrations are manipulated to make the $\Delta G$ for methanogenesis more negative, the organisms can capture more ATP and grow faster and more quickly begin producing methane. In addition, due to the faster growth rate, the organisms do not wash out of the digester as easily. They will also degrade the acetic acid more quickly to $CH_4$ and $CO_2$. Thus, the use of Directed Equilibrium decreases VFA concentration, which in turn accelerates degradation of substrate such as ligno-cellulose or hemicellulose. It was found that cellulose degradation was inhibited once acetic acid exceeded 1% by volume of rumen fluid.

The previous disclosures (U.S. Ser. No. 60/870,441; U.S. Ser. No. 12/000,856) described the ways to increase methane production by directing the equilibrium. The increased rate of acid degradation also makes biomass digestion faster and the system more stable. Ultimately, consistently maintaining conditions to increase the energy methane producers can capture enriches for methane producers that grow faster and can tolerate the higher flow rates. Ultimately, methane-producing organisms that are ideal for a certain set of conditions or growth rates could be isolated and used to inoculate digesters.

Example

Improving Mixed Cultures for Product Production

It was observed from data in the literature that 90% of the microorganisms isolated from cattle fed low-quality high-fiber diets cannot digest cellulose themselves. This observation raises the question, "What do these microorganisms consume for energy?" Since plant fiber (e.g. cellulose, hemicellulose, pectin) is a comprised of interwoven strands of long chains of sugars, the microorganisms cannot ingest the fiber itself. The means of survival for fiber-digesting microbes is to secrete enzymes to digest the fiber to sugars and disaccharides, and the microorganisms then ingest the sugars and disaccharides. Since producing complex enzyme systems to digest recalcitrant substrate costs the microorganisms a great deal of energy, various strains of microorganisms develop strategies to minimize this cost relative to the benefit.

One strategy is to not produce the cellulases or hemicellulases but rather scavenge the free carbohydrate released by other microbes. These microbes are called cross feeders, and they would seem to represent 90% of the rumen microbes for high-fiber diets. The strategy for survival would be to use the free sugars very efficiently for growth so that the organisms could survive even on very low sugar concentration.

The organisms that do produce fiber-digesting enzymes also have strategies for survival. One strategy is to attach to the biomass so that the sugars will be released in close proximity to where they are digested so they can be immediately consumed. The rumen contains some organisms that attach and others that do not. The fiber-digesters may also produce anti-bacterial compounds to inhibit growth of the cross feeders. Such competition (cross feeding) and anti-competitive behavior explains why some microorganisms digest feedstock faster in pure culture than the mixed culture of microorganisms in the rumen. The growth of fiber-digesters is slower due to cross feeding, and the anti-bacterial action may inhibit growth of both.

Based on the environment in which fiber-digesting microorganisms grow, there is no advantage for a microorganism to produce more enzymes than it needs to digest as much fiber as it needs. Therefore, most cellulytic enzymes are inhibited by volatile fatty acids or sugars, and the gene expression leading to their secretion is also inhibited. Producing excessive amounts of sugars would only feed the cross feeders. Producing a high concentration of a product, when thermodynamically limited, requires a high concentration of substrate such as glucose. Therefore, the competition in the natural environment can be an impediment to producing a high concentration of product. However, when microbes are removed from the natural environment they can be grown under conditions to select for organisms that do produce a high concentration of sugar so as to make a high concentration of desired product. Growing the microbes in the presence of a high concentration of the product adapts those microbes to produce more sugar from the plant fiber. Only the mutants that are not as good at turning off their cellulases would survive.

One aspect of the present invention is to adapt microbes to produce a higher concentration of sugar by growing them with a higher concentration of products, while maintaining the gas composition and other products to prevent a shift to some other product. Another aspect of the invention is the idea of incubating organisms together in co-cultures that produce a high concentration of a desired product. If an organism is isolated that can produce a high concentration of the desired product from a relatively high concentration of sugar, it may be used with a fiber-digester that produces a high concentration of the sugar. If 90% of the glucose released is used by the cross feeder, most of the product will be the desired product regardless of what the fiber-digester produces. Although individual organisms that can produce many different desired products directly from plant fiber were isolated, a co-culture so defined would be another way to produce the desired product.

Understanding that a high concentration of product (acid, alcohol, or other) depends on thermodynamics and concentrations of reactants and products enables development of methods to achieve the highest possible concentrations of products for the least cost. This high concentration of a few products decreases the cost of separation. Since mono- or disaccharides are often the intermediate that must be in high concentration to produce a high concentration of alcohol or acid, these intermediates must be accumulated to a high concentration. Mechanisms have evolved to decrease digestion of cellulose or hemicellulose when free glucose or other intermediate concentration is high, but conditions can be created to force the evolution of organisms around these natural mechanisms. In addition, mixed substrates can be used to the advantage of the chemical producer. For example, a fresh substrate with free sugar or starch (or pectin or protein) can be added at the end of the fermentation to achieve the final highest concentrations of product. If some of the feedstock cannot be digested at the final concentration of product, it can be recycled to a new digestion process at an earlier stage.

Other Uses of Directed Equilibrium Process

It is possible to isolate and develop microorganisms to produce a desired product from natural mixed populations of microorganisms in which only trace amounts of the desired product are produced. Although production of any alkanes greater in length than one carbon by rumen microorganisms was entirely unexpected and previously undocumented, using Directed Equilibrium process=made it possible to produce alkanes from volatile fatty acids through fermentation. These results show that the process of Directed Equilibrium might even be used in the future to produce other products not known to be produced by microorganisms.

A wide range of examples have been provided to demonstrate the invention of Directed Equilibrium comprising vastly different organic compounds (e.g. ethanol, butane) and inorganic compounds (e.g. $H_2$), using different types of microbial populations (e.g. rumen fluid, feces), isolating different kingdoms of organisms (e.g. fungi, bacteria, archaea), using aerobic and anaerobic conditions, and using different temperatures (e.g. 25° C. to 55° C.). The invention has now been demonstrated under a wide range of conditions, making it likely to be useful for many other processes yet undiscovered. The basis of the invention rests in the laws of physics, particularly the laws of thermodynamics, and the most fundamental principle of biology, the theory of evolution. These scientific theories are principal discoveries to explain nature, wherein the process of Directed Equilibrium is a means to control natural and industrial fermentations. The process of directed evolution involves using the principles to determine how to manipulate a living ecosystem to control metabolism and evolution. The same general method may be applied to produce many other compounds through fermentation or other living system.

Additional Example

Microbes that Produce Alcohols and Carboxylic Acids from $CO_2$, and $H_2$

Microorganisms were isolated that could produce a high concentration of ethanol from $CO_2$ and $H_2$ or from CO and $H_2$. A high ratio of $H_2$ to $CO_2$ was shown to favor alcohols or longer chain volatile fatty acids over methane or acetate. Some isolates produced mostly butyric acid or a combination of butyric acid and valeric acid. Other isolates produced similar molarities of ethanol and acetate. Isolates were tolerant to high concentrations of ethanol (e.g. 6%) or acids. Evidence that some organisms produced valerate or butyrate from acetate and propionate suggests that longer-chain acids could also have been produced as a means to use $H_2$ to generate ATP in the absence of $CO_2$. Elongation of carboxylic acids would be favored under conditions with high H2 and low $CO_2$.

Some VFA profiles for organisms that produced VFA from synthesis gases are shown in Table 4. The organisms were isolated by the procedures described in this disclosure. The pH for enrichment and isolation was 7. The incubation temperature was 39° C. The gas phase during enrichment and isolation was 3:1 H2 to CO 2 at 2 atm. About 100 organisms were isolated and screened by transferring the colonies to broth (as described) and incubating for 5 days under gas pressure without shaking (in retrospect shaking or bubbling would have been preferred). The 15 colonies that produced the most interesting profile of products (as measured by gas chromatography) were sub-sampled and again incubated in duplicate under similar conditions. The results are for the mean of the duplicate samples.

TABLE 4

Product profile of selected isolated strains of microorganisms.

| Iso-late | Ace-tate | Propio-nate | Bu-tyrate | Iso-Butyrate | Valerate | Iso-Valerate | Ethanol |
|---|---|---|---|---|---|---|---|
| | | | | Molar % of Total VFA | | | |
| S3 | 56 | 10 | 34 | 0 | 1 | 0 | 3 |
| S13 | 36 | 6 | 48 | 2 | 2 | 6 | 1 |
| S90 | 95 | 2 | 0 | 0 | 2 | 1 | 3 |
| S99 | 46 | 4 | 2 | 18 | 4 | 27 | 7 |
| S120 | 42 | 2 | 1 | 20 | 1 | 34 | 20 |
| S121 | 45 | 5 | 4 | 18 | 1 | 27 | 15 |

Standard error = 0.07%, n = 30.

The results indicate a tremendous variation in which products the organisms could produce when incubated under similar conditions. Strain S90 is similar to stains that have been previously isolated to produce acetate and to attempt to produce increasing amounts of ethanol. However strains S120 and S121 produced far greater ethanol under the same conditions. Strains S3 and S13 produce a high percentage of butyrate, and stains S99, S120, and S121 produced large amounts of iso-butyrate and isovalerate. One strain produced about 12% molar percentage as valerate but the duplicate did not grow so results are not shown.

Wherein others have isolated organisms that could synthesize acetate or trace quantities of ethanol, the present results show that using the isolation techniques described in this disclosure, organisms could be isolated that preferentially produced VFA that are seldom observed from synthesis gases, such as isovalerate and iso-butyrate. These particular VFA are valuable as potential feedstock to produce alkanes, alcohols, or other products.

Animal nutritionists believed previously that branched chain VFA (iso-butyrate and iso-valerate) in the rumen were derived exclusively from amino acids in the feed, and adding them to the rations of ruminants increases growth and milk production, particularly for low-protein diets. The quantity of these VFA produced from synthesis gas by some of these isolates were orders of magnitude higher than the quantity of branched-chain amino acids in the media. These particular VFA are valuable as feeds for animals, including ruminants. The organisms themselves may be used to enhance digestion and metabolism.

Other microorganisms that produce even more specific profiles of carboxylic acids are contemplated. In addition, longer-chain carboxylic acids could also be produced by using the isolations suggested in this disclosure. For example, incubating with octanoic acid under conditions to degrade it (e.g. N2, air, or H2 gas) could enrich for organisms that can have the enzymes for octanoic acid degradation, and some of these organisms could be selected to produce octanoic acid under conditions of $H_2$ to $CO_2$ ratio of 3 and total pressure of 2 to 4 atm. Other conditions could also be used as long as the calculated conditions make it thermodynamically feasible and thermodynamically favorable to drive each reaction in the desired direction. The longer-chain carboxylic acids can easily be separated from the aqueous media because they are immiscible and les dense than water. Therefore, the carboxylic acids float to the surf ace. The process can be further facilitated by centrifuging or extracting in solvents or separating by heating or cooling to cause different phase changes compared to water.

The results presented show that individual microbes produce specific carboxylic acids in many cases. In other words, many microbes do not produce a large array of carboxylic acids of different sizes but they excrete certain end products, and published research shows they incorporate certain carboxylic acids into their membranes. Therefore, by isolating organisms that produce a certain product, specific carboxylic acids can be produced. These acids could be converted to specific alkanes or other chemicals or could be separated and used. Thus, it is possible to convert a high percentage of a product to a desired carboxylic acid and subsequently to a desired alkane or set of alkanes.

Synthesis gases include $CO_2$ and $H_2$ or CO and $H_2$ or a combination of $CO_2$ and CO and $H_2$. Wherein, $CO_2+H_2$ is in equilibrium with CO and $H_2O$, either $CO_2$ and/or CO with $H_2$ can be used. The optimal ratio of $H_2$ to CO is equal to one less than the optimal ratio of $H_2$ to $CO_2$. For example, if the optimal ratio of $H_2$ to $CO_2$ for carboxylic acid elongation is 3, the optimal ratio for $H_2$ to CO is 2 (3−1). Otherwise, the same principles apply to the in terms of the effects of pressure, pH and ratios. Organisms use a certain ratio of $H_2$ to $CO_2$ use the equivalent ratio (one unit less) of $H_2$ to CO in a similar manner in general, with a few exceptions.

Additional Example

Microbial Isolates that Produce Alkyl Alcohols from Synthesis Gases

A previous patent application (U.S. Ser. No. 61/165,654) disclosed the use of Directed Equilibrium to isolate microorganisms for converting synthesis gases ($CO_2$, CO, and $H_2$) to a predominant product such as a predominant alcohol or acid. The methods described therein (U.S. Ser. No. 61/165,654) were employed for isolation of several strains of synthesis gas users. The process of Directed Equilibrium has now been used to isolate microorganisms that convert a high percentage of $CO_2$ and $H_2$ to ethanol, or alternatively organisms that produce propanol or butanol. Different isolates produce a number of predominant volatile fatty acids or mixtures of volatile fatty acids as well. The isolates may also produce acetic acid or elongate the acids to longer-chain volatile fatty acids.

These microorganisms were isolated by first enriching for the desired product under conditions that would favor degradation of that product, and then they were selected under conditions that favored production of the desired product. For example, rumen contents prepared as described previously for isolation of microorganisms were incubated in media with no added energy substrate other than 6% by volume ethanol, 10% by volume ethanol, 4% by volume propanol, 6% by volume propanol, or 4% by volume butanol. The headspace gas for enrichment was either N2 or air. Other conditions included maintenance of pH above 6.8 using buffers and incubation at 39° C. Thus, the thermodynamic calculations indicate that organisms could obtain energy by degrading the alcohols to $CO_2$ and $H_2O$ or some other intermediate. After incubating for 2 to 4 days, the culture was sub-sampled and added to new media and the enrichment continued. The process was repeated for several cycles.

Once the microbial population was enriched for alkyl alcohol degraders, selection was made in roll tubes. The roll tubes also contained no energy substrate except an optimal ratio of gases for conversion of synthesis gases to alcohols. In other respects they were similar to the roll tubes used to select fiber-digesting microbes already described. For example, the ratio of H2 to CO 2 was 3 to 1, which was determined to yield the most energy for conversion to alcohols of any ratio based on the second law of thermodynamics (U.S. Ser. No. 61/165,654). The colonies that grew under these conditions were thought to be able to synthesize alcohols.

The initial screening demonstrated that in fact many of the isolates so obtained produced volatile fatty acids or alcohols from the $H_2$ and $CO_2$. Several isolates were selected because they converted a higher percentage of the biomass to ethanol, propanol or butanol than others. These were incubated another time in $H_2:CO_2$ of 3:1. In general acetate was the predominant product and ethanol second, but other alcohols and acids were formed to different extents depending on the isolate. One isolate converted about 20% of the gas used to ethanol and 80% to acetate. Whereas, these organisms were selected from conditions of high ethanol, propanol, or butanol concentration, and the thermodynamic calculations show that such organisms would be able to obtain energy from making the alcohol if the ratio of the gases is optimal and especially if pressurized, the production of high concentrations of the alcohols are expected. Another advantage of the isolates is that they were enriched in air, and although they may not produce the desired products in the presence of oxygen, the tolerance to oxygen would be advantageous. Continued incubation of the isolates in the presence of VFA would make it thermodynamically favorable to produce the alcohols and further improve conversion of gases to alcohols. Additional isolations can be conducted with VFA in the media to further shift fermentation toward the alcohols.

The process of making the organisms tolerate higher concentrations of desired alcohols, or convert a higher portion of the gases to desired alcohols instead of acids will follow the same procedures as described for making organisms tolerate more alcohol or convert a higher portion of product for biomass digestion and conversion.

Further Discussion of Embodiments

The approach of Directed Equilibrium can apply to many different types of biomass and many different organic compounds. The process of Directed Equilibrium provided herein provides digestion of different types of biomass including cellulose (or ligno-cellulose), hemicellulose and others to desired products at a faster rate and to a greater extent. The examples provided herein demonstrate additional results of conversion of biomass to desired products including additional observations of producing ethanol at very high concentrations (e.g. >10%). Microorganisms can be isolated that convert a high proportion of carbon dioxide and hydrogen to ethanol as opposed to other products, or that produce 1-propanol from these gases. Microorganisms can also be isolated that produced predominantly a single volatile fatty acid such as acetic acid, propionic acid, butyric acid, or valeric acid from cellulose, carboxymethyl cellulose, ligno-cellulose, or timothy hay. The following are exemplary uses of Directed Equilibrium:

Enriching and selecting for microorganisms that grow rapidly while producing methane, and use of such microbes in bioreactors producing methane in which the methanogens do not wash out of the reactor.

Providing for a greater rate and extent of biomass degradation for different types of biomass.

Using isolated microorganisms and digestion process to better define the meaning of tolerance of isolated organisms to products such as alcohols.

Isolating microorganisms and testing conditions that produce single predominant volatile fatty acids including acetic acid, propionic acid, butyric acid, and valeric acid from cellulosic biomass such as paper, carboxymethyl cellulose, or timothy hay.

Isolating and testing microorganisms that convert a high percentage of carbon dioxide and hydrogen to ethanol or propanol, and which are tolerant to high concentrations of the respective alcohol.

Discovering microorganisms that can produce alkanes with greater than one carbon in length such as ethane, propane, butane and others from volatile fatty acids. The volatile fatty acids can be produced in turn by digestion of biomass or assimilation of synthesis gases.

The present disclosure also provides a method for predominantly producing specific organic compounds using microbial cultures, or producing higher concentrations of specific compounds than would be produced by natural cultures of microorganisms. Means are described to select for organisms that are more likely to digest plant fiber well, produce a higher concentration of alcohol, produce an alcohol or acid from synthesis gases.

The present disclosure also provides a means to enrich or select for microorganisms that degrade various types of biomass comprising: cellulose, hemicellulose, lignin, pectin, starch or others wherein the microorganisms rapidly digest the cellulose and hemicellulose in the biomass even when it is bound to lignin to produce desired products.

The present disclosure also provides methods to produce a high concentration of lower alkyl alcohol directly from plant fiber. Moreover, it is contemplated that lactic acid may be produced from plant fiber using isolates obtained using hydrogenase inhibitors. Hydrogenase inhibitors such as carbon monoxide prevent transfer of H2 into and out of bacterial cells. If microorganisms produce acetic acid they need to export H2 or use it internally. If they produce propionate from glucose or butyrate from acetate they need to import H2. The only major metabolites that can be produced individually without hydrogenases are ethanol, butanol, and lactate. Many of the bacterial isolates from high $H_2$ or CO concentration were identified as lactic acid bacteria using 16-S r-DNA. Thus, probably lactic acid bacteria that can digest plant fiber were already isolated although the presence of lactic acid in the fermentation broth was not measured. Isolation of lactic acid bacteria that can digest plant fiber could enable production of bio-plastics from lower cost sources of biomass than the current standard of using starch or sugars.

The use of Directed Equilibrium facilitates the design and operation of industrial-scale bio-product fermentation. Several methods of industrial scale fermentation have been described in previous patent applications (e.g. U.S. Ser. No. 12/385,215).

Industrial Processes

The use of fossil fuels has created global climate change problems and fossil resources of many types are dwindling. There are many products currently produced from fossil fuels that could be produced from biomass instead. These products include biofuels and other products. The value of the products will depend upon supply and demand which in turn will depend on what sources of biomass can be used. The proposed invention can be used to produce microorganisms that can produce many different bioproducts from many different sources of feedstock. The array of organisms will enable digestion of many different forms of biomass, so that biomass shortages can be averted.

The invention of Directed Equilibrium as described in this disclosure will make it possible to isolate microorganisms to produce many different products. Some products may be valuable but only needed in small quantity. Other products may need to be produced from the least expensive biomass source feasible to be cost effective. The types of biomass that might be used could include grass, wood waste, waste paper, card board, algae, food waste, animal and human manure, leaves, and biofuel crops. All sources of biomass identified previously (U.S. Ser. No. 12/000,856) for alcohol production could be used for any of the bioproducts that can be produce using this invention. Additional products could include fertilizer, microbial protein that could be used as a feed supplement, or carbon or nitrogen trading credits.

When using a pure culture of microorganisms, the biomass may need to be sterilized by heat and pressure or with chemicals to prevent competition with other microorganisms. When heat is used, the same source of heat may be captured with a heat exchanger and shared with heat for distillation of products if necessary. Distillation may also be by using vacuum or purging with gases. It would make sense to have a mixer that can be filed with biomass intermittently, and which feeds the feedstock into the system continuously from there. The residual biomass could include lignin and other indigestible residues, which could be used as a fertilizer or burned. One of the surprising aspects of the process is the rapid speed at which the process can occur. In experiments conducted already, the volatile fatty acids were converted to alkanes in a matter of hours or days, at neutral pH and 39° C. The use of extreme conditions and long periods of time thought to bring about the production fossil fuels were not necessary. An industrial process may involve use of one set of microorganisms to produce the acids and a second set, simultaneously or in separate batches, to produce the alkanes from the acids. The alkanes can then be removed. Any of the process steps for other products described in this disclosure or in a previous disclosure (U.S. Ser. No. 12/000,856) for alcohol production can be used.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for converting a substrate to a $C_2$-$C_8$ alkane, comprising the steps:
    a) adding the substrate to a fermentation vessel;
    b) supplying a source of hydrogen gas to the fermentation vessel to increase the partial pressure of hydrogengas in the fermentation vessel to at least 0.001 atmospheres;
    c) fermenting the substrate in the fermentation vessel with a microbial culture that converts the substrate to the $C_2$-$C_8$ alkane; and
    d) removing the alkane.

2. The method of claim 1, wherein the $C_2$-$C_8$ alkane is selected from a group consisting of ethane, propane, n-butane, and iso-butane.

3. The method of claim 1, wherein the $C_2$-$C_8$ alkane is selected from a group consisting of pentane, hexane, heptane, and octane.

4. The method of claim 1, wherein gases in the fermentation vessel are at a total pressure of about 1 to about 4 atmospheres.

5. A method for converting a substrate to a $C_2$-$C_8$ alkane, comprising the steps:
    a) adding the substrate to a fermentation vessel;
    b) supplying a source of hydrogen gas to the fermentation vessel, wherein ratio of $H_2$:$CO_2$ by volume is about or at least 3:1, or ratio of $H_2$:CO by volume is about or at least 2:1;
    c) fermenting the substrate in the fermentation vessel with a microbial culture that converts the substrate to the $C_2$-$C_8$ alkane; and
    d) removing the alkane.

6. The method of claim 1, wherein the substrate comprises gases $H_2$ and $CO_2$ or CO, which are converted to the alkane and $H_2O$ by the microbial culture.

7. The method of claim 1, wherein the substrate comprises a carboxylic acid, and the microbial culture hydrogenates the carboxylic acid to produce the alkane and $H_2O$.

8. The method of claim 1, wherein the substrate comprises biomass.

9. The method of claim 8, wherein the biomass comprises cellulose.

10. The method of claim 1, wherein temperature of broth in the vessel is greater than 20° C. and less than 60° C.

11. The method of claim 6, further comprising mathematically determining the reaction conditions needed to produce the alkane at a desired concentration from the gases by calculating $\Delta G$ values for a plurality of alternative reaction conditions for converting the gases to the alkane and $\Delta G$ values for converting the gases to acetate, and selecting a set of reaction conditions that make it thermodynamically favorable to produce the alkane at a desired concentration over producing the acetate; and adding the gases or the acetate or removing the alkane to establish the reaction conditions needed to produce the alkane at the desired concentration.

12. The method of claim 11, wherein the alternative reaction conditions include different partial pressures of gases comprising $H_2$, $CO_2$, or CO.

13. A method for isolating microorganisms that convert a substrate to a $C_2$-$C_8$ alkane comprising: collecting a sample from a source containing microorganisms that produce the alkane; growing the microorganisms in a culture in a fermentation vessel;

supplying a source of hydrogen gas to the fermentation vessel to increase partial pressure of hydrogen gas in the fermentation vessel to at least 0.001 atmospheres; and isolating one or more microorganisms from the culture.

14. A process to ferment a substrate to a $C_2$-$C_8$ alkane comprising;

adding the substrate and an isolated microorganism to a fermentation vessel;

infusing a source of hydrogen gas into the fermentation vessel to increase the partial pressure of hydrogen gas in the fermentation vessel to at least 0.001 atmospheres; wherein the isolated microorganism produces the $C_2$-$C_8$ alkane; and removing the $C_2$-$C_8$ alkane.

15. The process of claim 14, wherein the substrate comprises $CO_2$, or CO.

16. The process of claim 14, wherein the substrate comprises a carboxylic acid.

17. The process of claim 14, wherein the isolated microorganism is anaerobic.

18. The process of claim 14, wherein the isolated microorganism contains 16S rRNA that is at least 97% homologous with that of a member of a taxonomic genus from among *Actinomyces, Enterococcus, Eschericia, Clostridium, Proteus,* or *Tissierella*.

19. The process of claim 1, wherein partial pressure of hydrogen gas in the fermentation vessel is at least 0.05 atmospheres.

* * * * *